United States Patent
Bamdad et al.

(10) Patent No.: US 12,104,170 B2
(45) Date of Patent: Oct. 1, 2024

(54) METHODS FOR DERIVING DOPAMINERGIC NEURONS FROM PLURIPOTENT STEM CELLS

(71) Applicant: MINERVA BIOTECHNOLOGIES CORPORATION, Waltham, MA (US)

(72) Inventors: Cynthia Bamdad, Waltham, MA (US); Kevin R. Yi, Waltham, MA (US); Scott T. Moe, Waltham, MA (US); Thomas Jeon, Waltham, MA (US)

(*) Notice: Subject to any disclaimer, the term of this patent is extended or adjusted under 35 U.S.C. 154(b) by 0 days.

(21) Appl. No.: 18/002,828

(22) PCT Filed: Jun. 28, 2021

(86) PCT No.: PCT/US2021/039431
§ 371 (c)(1),
(2) Date: Dec. 21, 2022

(87) PCT Pub. No.: WO2021/263241
PCT Pub. Date: Dec. 30, 2021

(65) Prior Publication Data
US 2023/0242874 A1 Aug. 3, 2023

Related U.S. Application Data

(60) Provisional application No. 63/051,455, filed on Jul. 14, 2020, provisional application No. 63/045,432, filed on Jun. 29, 2020, provisional application No. 63/044,683, filed on Jun. 26, 2020.

(51) Int. Cl.
*C12N 5/0793* (2010.01)
*A61K 35/30* (2015.01)

(52) U.S. Cl.
CPC ............ *C12N 5/0619* (2013.01); *A61K 35/30* (2013.01); *C12N 2500/38* (2013.01); *C12N 2501/10* (2013.01); *C12N 2501/415* (2013.01); *C12N 2501/999* (2013.01); *C12N 2506/02* (2013.01); *C12N 2506/45* (2013.01)

(58) Field of Classification Search
CPC .............. C12N 5/0619; C12N 2500/38; C12N 2501/10; C12N 2501/415; C12N 2506/45; A61K 35/30
See application file for complete search history.

(56) References Cited

U.S. PATENT DOCUMENTS

| | | |
|---|---|---|
| 5,631,271 A | 5/1997 | Serfontein |
| 10,017,734 B2 | 7/2018 | Shoji |
| 2008/0268019 A1 | 10/2008 | Badylak et al. |
| 2009/0123433 A1 | 5/2009 | Shroff |
| 2011/0296542 A1 | 12/2011 | Wang et al. |
| 2013/0040390 A1 | 2/2013 | Pei et al. |
| 2015/0159135 A1 | 6/2015 | Davis et al. |
| 2015/0301067 A1 | 10/2015 | Miller et al. |
| 2017/0159014 A1 | 6/2017 | Lee et al. |
| 2018/0094242 A1* | 4/2018 | Studer .................. A61K 35/30 |
| 2018/0263964 A1 | 9/2018 | Bamdad et al. |
| 2020/0172862 A1 | 6/2020 | McMahon et al. |

FOREIGN PATENT DOCUMENTS

| | | |
|---|---|---|
| CN | 110872576 A | 3/2020 |
| WO | WO-2016162747 A2 | 10/2016 |
| WO | WO-2017137255 A1 | 8/2017 |
| WO | WO-2019212691 A1 | 11/2019 |
| WO | WO-2021263241 A1 | 12/2021 |

OTHER PUBLICATIONS

Bagga et al. Ascorbic acid increases the number of dopamine neurons in vitro and in transplants to the 6-OHDA-lesioned rat brain. Cell Transplant 17(7):763-773 (2008).
Bremner et al. The neurobiology of retinoic acid in affective disorders. Prog Neuropsychopharmacol Biol Psychiatry 32(2):315-31 (2008).
Calderon-Ospina et al. B Vitamins in the nervous system: Current knowledge of the biochemical modes of action and synergies of thiamine, pyridoxine, and cobalamin. CNS Neurosci Ther 26(1):5-13 (2020).
Cooper et al. Differentiation of human ES and Parkinson's disease iPS cells into ventral midbrain dopaminergic neurons requires a high activity form of SHH, FGF8a and specific regionalization by retinoic acid. Mol Cell Neurosci 45(3):258-266 (2010).
Engberg et al. Retinoic acid synthesis promotes development of neural progenitors from mouse embryonic stem cells by suppressing endogenous, Wnt-dependent nodal signaling. Stem Cells 28:1498-1509 (2010).
Gudas et al. Retinoids regulate stem cell differentiation. J. Cell Physiol 226:322-330 (2011).
Guilarte et al. Effects of Perinatal Vitamin B6 Deficiency on Dopaminergic Neurochemistry. J Neurochem 48(2):432-439 (1987).
He et al. Vitamin C facilitates dopamine neuron differentiation in fetal midbrain through TET1- and JMJD3-dependent epigenetic control manner. Stem Cells 33(4):1320-1332 (2015).
Khillan. Vitamin A/retinol and maintenance of pluripotency of stem cells. Nutrients 6(3):1209-1222 (2014).
Luan et al. Developmental Vitamin D (DVD) Deficiency Reduces Nurr1 and TH Expression in Post-mitotic Dopamine Neurons in Rat Mesencephalon. Mol Neurobiol 55(3):2443-2453 (2018).
Mu et al. RIP140/PGC-1α axis involved in vitamin A-induced neural differentiation by increasing mitochondrial function. Artif Cells Nanomed Biotechnol 46(sup1):806-816 (2018).
PCT/US2021/039431 International Search Report and Written Opinion dated Oct. 21, 2021.

(Continued)

*Primary Examiner* — Kara D Johnson
(74) *Attorney, Agent, or Firm* — WILSON SONSINI GOODRICH & ROSATI

(57) ABSTRACT

The present application discloses a method of producing dopaminergic neurons from human stem cells by adding or increasing concentration of vitamin into neuro basal media at approximately Day 20+/−3 of a protocol for differentiating pluripotent stem cells into dopaminergic neurons.

37 Claims, 43 Drawing Sheets

(34 of 43 Drawing Sheet(s) Filed in Color)

(56) References Cited

OTHER PUBLICATIONS

Peraza et al., Riboflavin and pyridoxine restore dopamine levels and reduce oxidative stress in brain of rats. BMC Neuroscience 19(1):71 (2018).

Samata et al. Purification of functional human ES and iPSC-derived midbrain dopaminergic progenitors using LRTM1. Nat Commun 7:13097 (2016).

Takahashi et al. Induction of pluripotent stem cells from mouse embryonic and adult fibroblast cultures by defined factors. Cell 126(4):663-676 (2006).

Wang, Mengmeng et al. Development and Differentiation of Midbrain Dopaminergic Neuron: From Bench to Bedside. Cells 9(6):1489 (2020).

* cited by examiner

Protocol A

D0
Plate on Geltrex
Neurobasal +N2 +B27 +GlutaMAX
+LDN193189 +SB431542 +SHH
+CHIR99021

D1-D6
Neurobasal +N2 +B27 +GlutaMAX
+LDN193189 +SB431542 +SHH
+CHIR99021

D7-D9
Neurobasal +N2 +B27 +GlutaMAX
+CHIR99021

D10
Neurobasal +B27 +GlutaMAX
+CHIR99021 +BDNF +GDNF
+AA +TGFβ3 +cAMP

D11
Plate on Polyornithine 1μg/ml Laminin
Fibronectin coated surface in Day 10
media

D12-D20
Neurobasal +B27 +GlutaMAX +BDNF
+GDNF +AA +TGFβ3 +cAMP +DAPT

D21 →
Neurobasal +B27 +GlutaMAX +BDNF
+GDNF +AA +TGFβ3 +cAMP +DAPT

Fig. 1A

Protocol B

β-catenin pre-treatment (optional)

D0
Plate on Geltrex
Neurobasal +N2 +B27 +GlutaMAX
+LDN193189 +SB431542 +SHH
+CHIR99021

D1-D6
Neurobasal +N2 +B27 +GlutaMAX
+LDN193189 +SB431542 +SHH
+CHIR99021

D7-D9
Neurobasal +N2 +B27 +GlutaMAX
+CHIR99021

D10
Neurobasal +B27 +GlutaMAX
+CHIR99021 +BDNF +GDNF
+AA +TGFβ3 +cAMP

D11
Plate on Polyornithine 10μg/ml Laminin
Fibronectin coated surface in Day 10
media

D12-D20
Neurobasal +B27 +GlutaMAX +BDNF
+GDNF +AA +TGFβ3 +cAMP +DAPT

D21 →
Neurobasal +B27 +Pyridoxal +GlutaMAX
+BDNF + GDNF +AA +TGFβ3
+cAMP +DAPT

Fig. 1B

| Cell line | Day 0 Seeding Density (cells/cm²) | Protocol | Day | Biogenically & Metabolically Secreted (ng/ml) | Biogenically & Metabolically Secreted (ng/ml) Normalized to 800K/cm² |
|---|---|---|---|---|---|
| hES_E8-HES3 | 800K | A | 40 | 2.22 | 2.22 |
| hES_E8-HES3 | 400K | C | 40 | 3.44 | 6.88 |
| hES_E8-HES3 +WNT3A | 400K | A | 40 | 1.22 | 2.44 |
| iPS_E8-A6 | 800K | B | 50 | 2.89 | 2.89 |
| iPS_E8-A6 | 800K | C | 40 | 33.51 | 33.51 |
| iPS_E8-A6 +WNT3A | 400K | A | 50 | 0.58 | 1.16 |
| iPS_NME7-6E | 800K | A | 50 | 1.49 | 1.49 |
| iPS_NME7-6E | 800K | C | 40 | 43.01 | 43.01 |
| iPS_NME7-6E | 800K | C | 60 | 54.1 | 54.1 |
| iPS_NME7-6E +WNT3A | 400K | A | 60 | 3.04 | 6.08 |
| iPS_NME7-6E +WNT3A | 400K | C | 60 | 12.54 | 25.08 |
| iPS_NME7-N7B | 400K | A | 60 | 0.43 | 0.86 |
| iPS_NME7-N7B | 400K | C | 40 | 20.59 | 41.18 |
| iPS_NME7-N7B | 400K | C | 60 | 17 | 34 |
| iPS_NME7-N7B +WNT3A | 200K | A | 60 | 0.55 | 2.2 |
| iPS_NME7-N7B +WNT3A | 200K | C | 60 | 2.46 | 9.84 |

Figure 8

| Cell line | Day 14 Replating Density (cells/cm²) | protocol | Day | Bombesin & Metabolites Secreted (ng/ml) | Somatostatin & Metabolites Secreted (ng/ml) normalized to 400K cells |
|---|---|---|---|---|---|
| iPS$_{NME7-6E}$ | 800K | A | 30 | 1.33 | 1.33 |
| iPS$_{NME7-6E}$ +WNT3A | 400K | A | 30 | 1.39 | 2.78 |
| iPS$_{NME7-6E}$ | 800K | C | 30 | 10.23 | 10.23 |
| iPS$_{NME7-6E}$ | 400K | C | 30 | 6.75 | 13.5 |
| iPS$_{NME7-6E}$ +WNT3A | 400K | C | 30 | 6.52 | 13.04 |
| iPS$_{NME7-6E}$ | 800K | A | 40 | 1.30 | 1.3 |
| iPS$_{NME7-6E}$ +WNT3A | 400K | A | 40 | 1.12 | 2.24 |
| iPS$_{NME7-6E}$ | 800K | C | 40 | 16.58 | 16.58 |
| iPS$_{NME7-6E}$ | 400K | C | 40 | 12.14 | 24.28 |
| iPS$_{NME7-6E}$ +WNT3A | 400K | C | 40 | 12.66 | 25.32 |
| iPS$_{NME7-6E}$ | 800K | A | 50 | 1.49 | 1.49 |
| iPS$_{NME7-6E}$ +WNT3A | 400K | A | 50 | 0 | 0 |
| iPS$_{NME7-6E}$ | 800K | C | 50 | 18.62 | 18.62 |
| iPS$_{NME7-6E}$ | 400K | C | 50 | 13.88 | 27.76 |
| iPS$_{NME7-6E}$ +WNT3A | 400K | C | 50 | 11.86 | 23.72 |
| iPS$_{NME7-6E}$ | 800K | A | 60 | 5.85 | 5.85 |
| iPS$_{NME7-6E}$ +WNT3A | 400K | A | 60 | 3.04 | 6.08 |
| iPS$_{NME7-6E}$ | 800K | C | 60 | 9.58 | 9.58 |
| iPS$_{NME7-6E}$ | 400K | C | 60 | 6.92 | 13.84 |
| iPS$_{NME7-6E}$ +WNT3A | 400K | C | 60 | 12.54 | 25.08 |

Figure 10

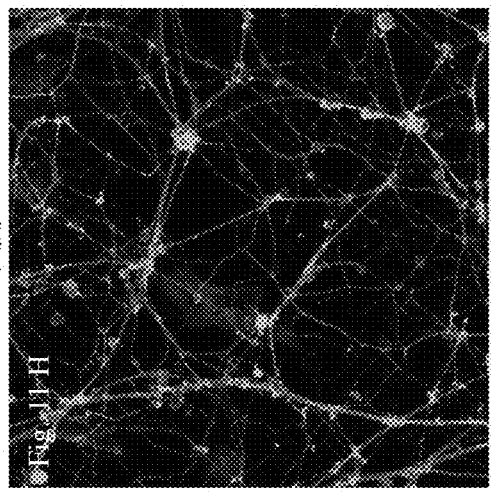
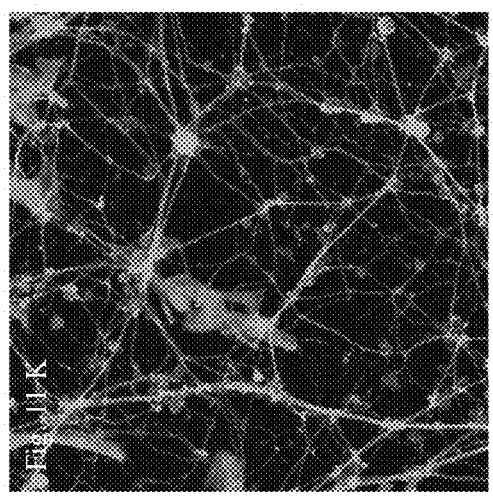
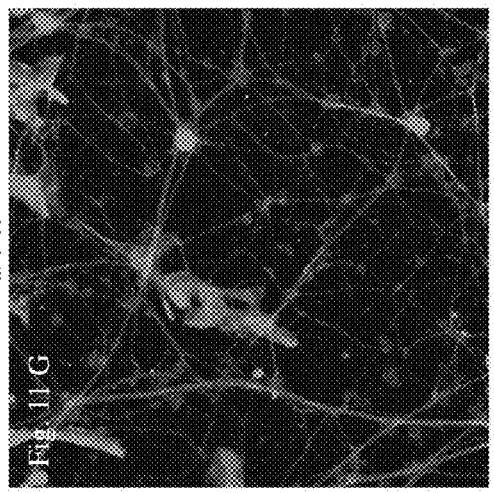
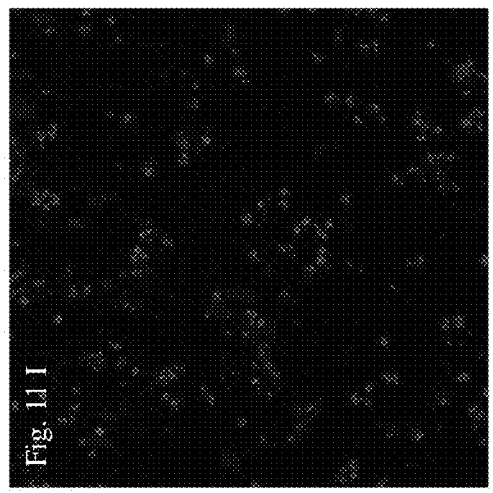
Control for addition of B6 vitamins: Protocol A, but with retinol and retinyl acetate added at about Day 20
Figure 11G – 11K

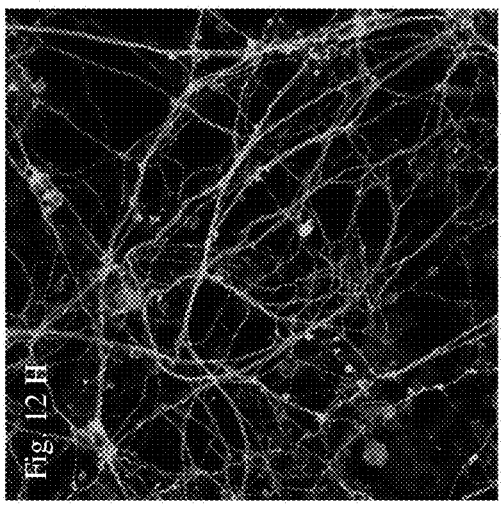
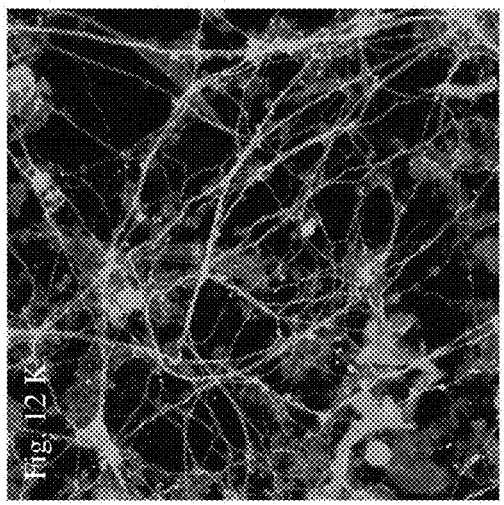
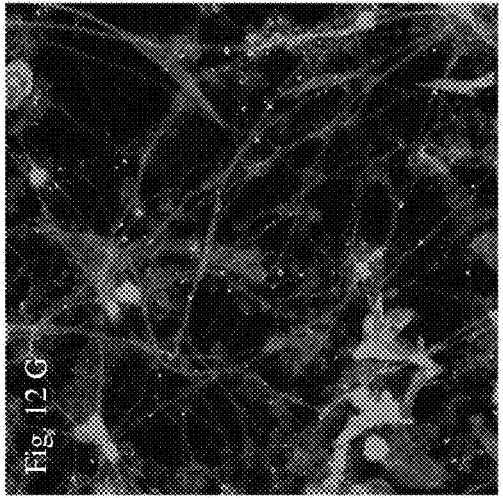
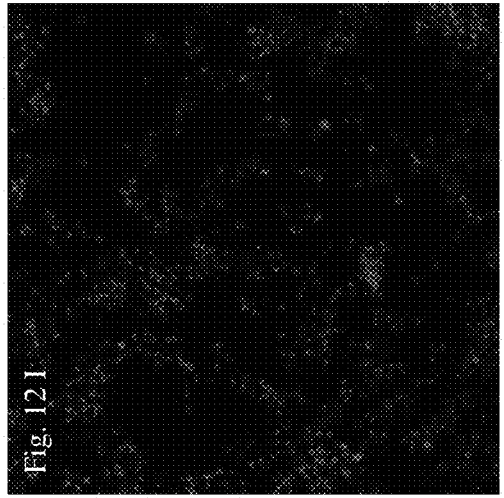
Figure 12G – 12K

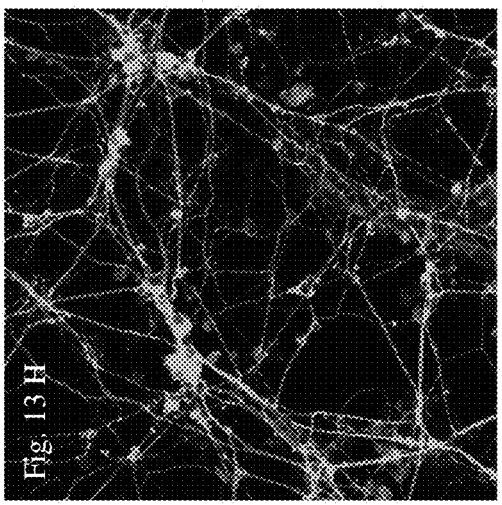
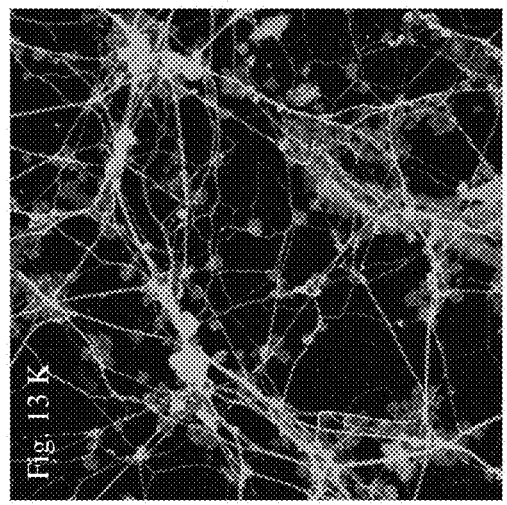
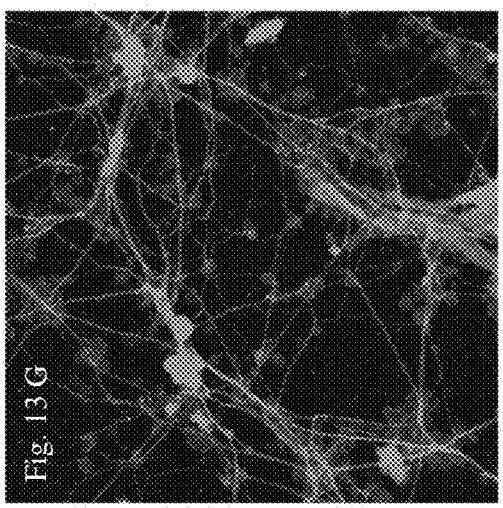
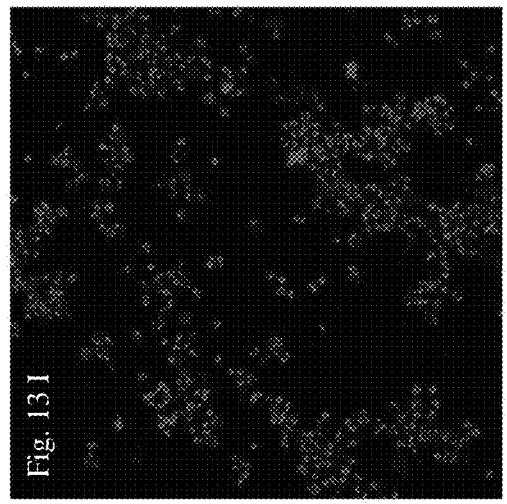
Protocol C, with retinol and retinyl acetate added at about Day 20, plus pyridoxal
Figure 13G – 13K

Fig. 14H TUJ

Fig. 14K merge

Fig. 14J phase

Protocol C, with retinol and retinyl acetate added at about Day 20, plus pyridoxal-5'-phosphate

Fig. 14G DAT

Fig. 14I Hoechst

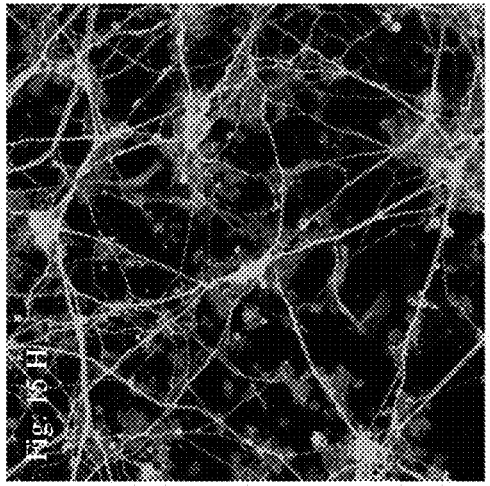
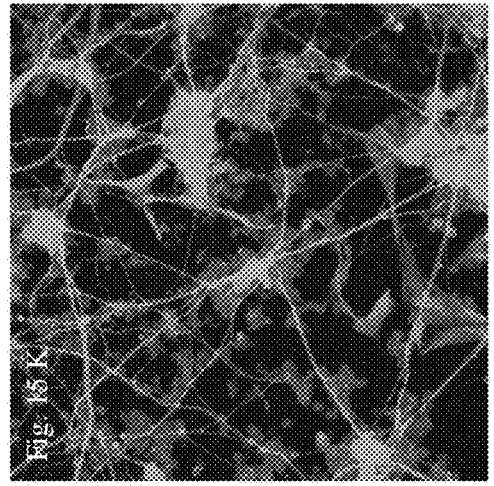
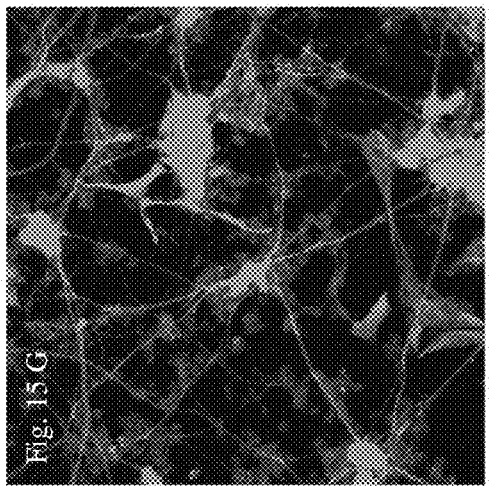
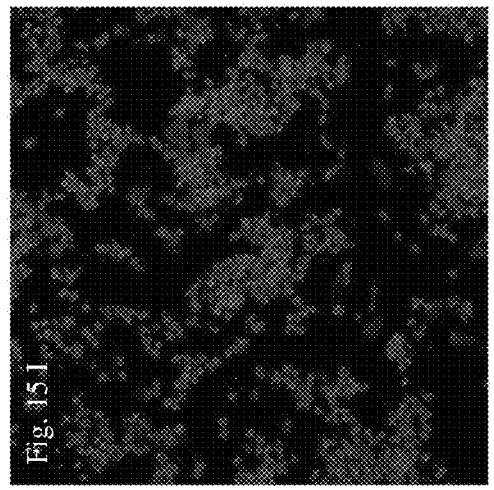
Protocol C, with retinol and retinyl acetate added at about Day 20, plus all 3 vitamin Bs: pyridoxine, pyridoxal and pyridoxal-5'-phosphate
Figure 15G – 15K Control 1: Protocol A, no additional vitamin B added from about Day 20 onward Control 1: Protocol A, no additional vitamin B added from about Day 20 onward Control 2: Protocol B, with additional pyridoxal added from about Day 20 onward Protocol C, with additional pyridoxal added from about Day 20 onward, plus retinol and retinyl acetate

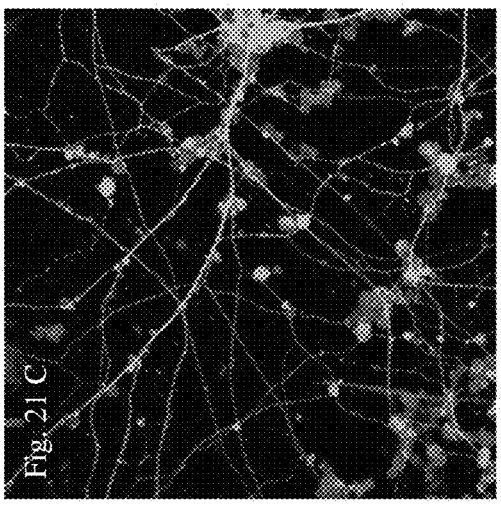
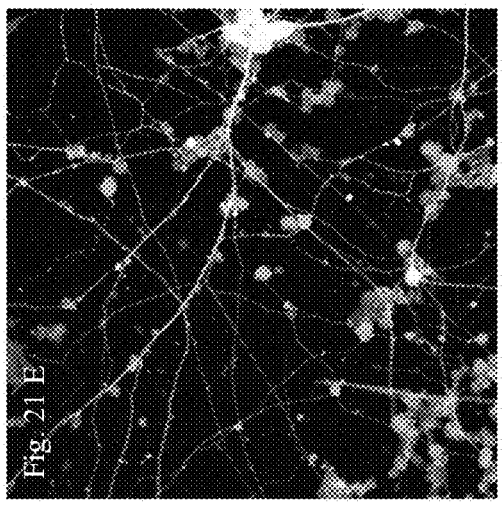
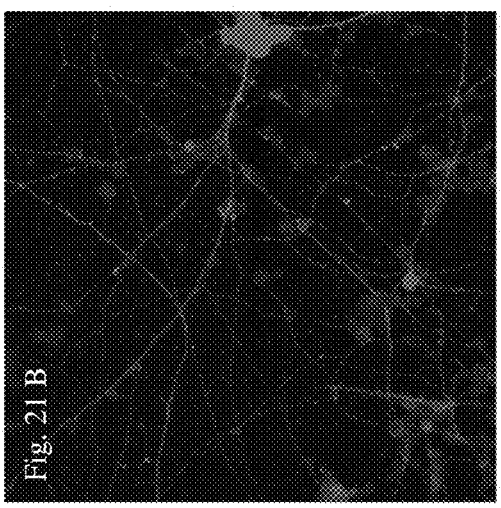
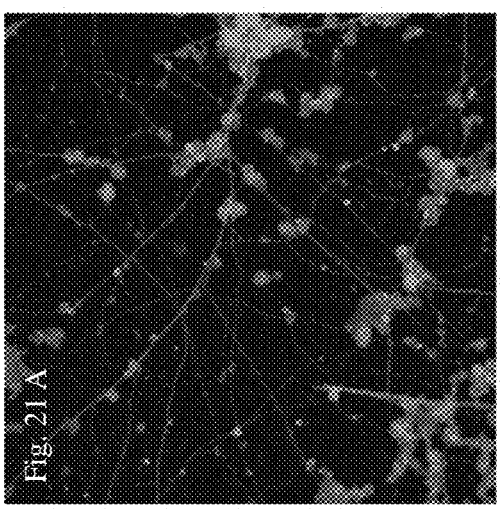
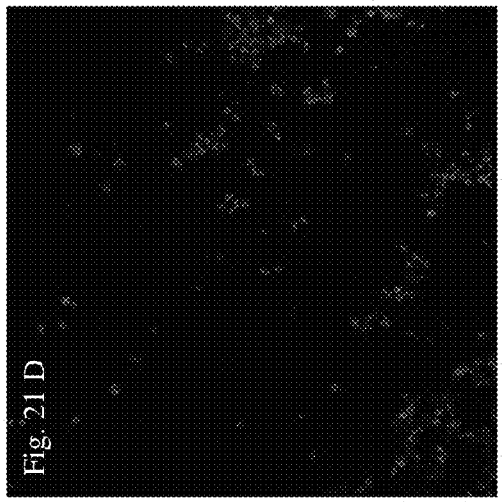
Figure 21A – 21E Protocol C, with additional pyridoxal added from about Day 20 onward, plus 9-cis, 13-cis, and all-trans retinoic acid Protocol C, with additional pyridoxal added from about Day 20 onward, plus 9-cis, 13-cis, and all-trans retinoic acid

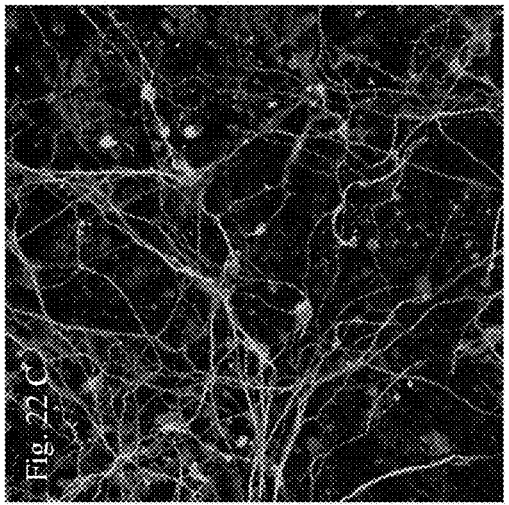
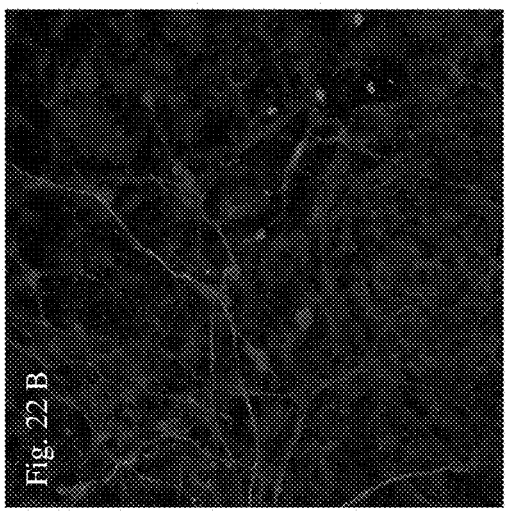
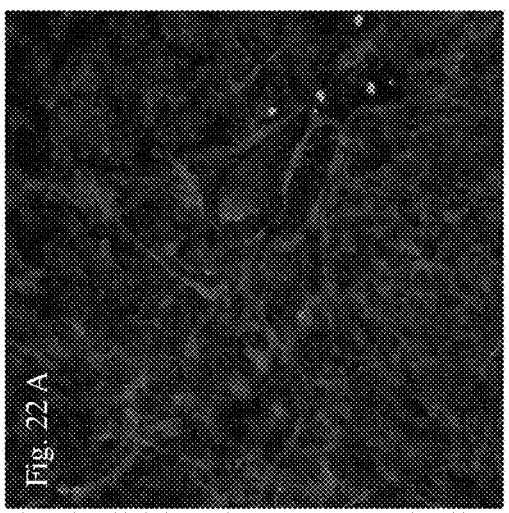
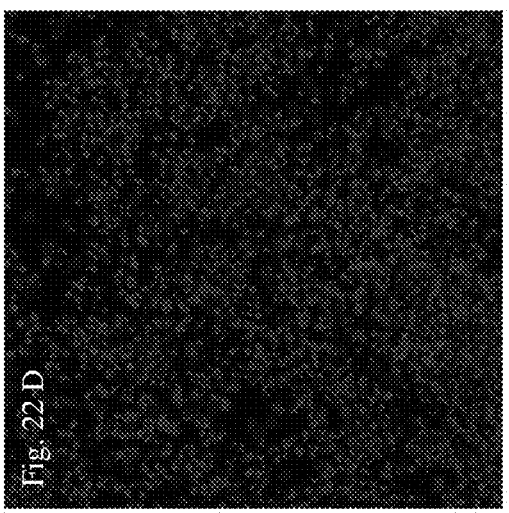
Figure 22A – 22E
Protocol C, with additional pyridoxal added from about Day 20 onward, plus all-trans retinoic acid Protocol C, with additional pyridoxal added from about Day 20 onward, plus all-trans retinoic acid Protocol B, with increased retinol and retinyl acetate concentrations and solubilized in Albumax Protocol B, with retinol and retinyl acetate, solubilized in Albumax, plus 2-phospho-ascorbic acid and L-ascorbic acid Protocol B, with retinol and retinyl acetate, solubilized in Albumax, plus 2-phospho-ascorbic acid and L-ascorbic acid

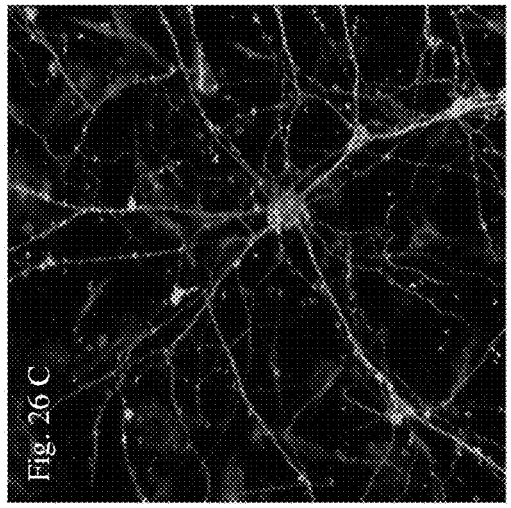
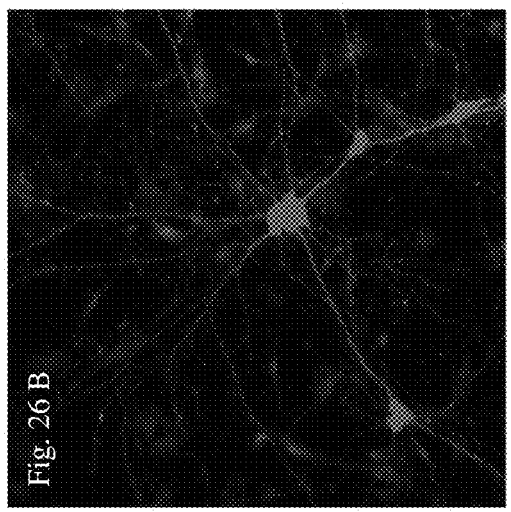
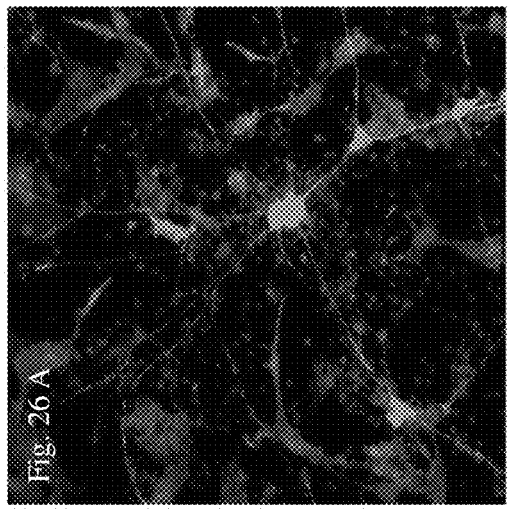
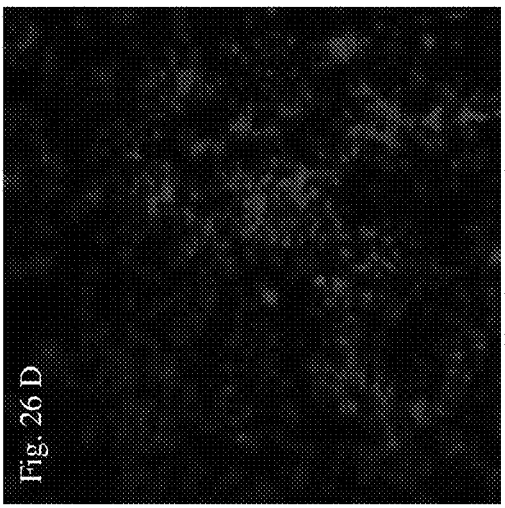
Figure 26A – 26E

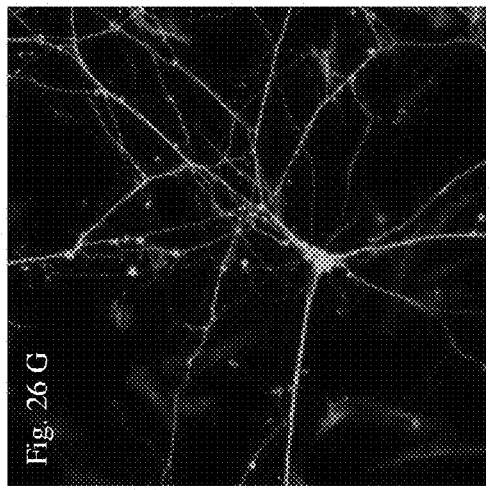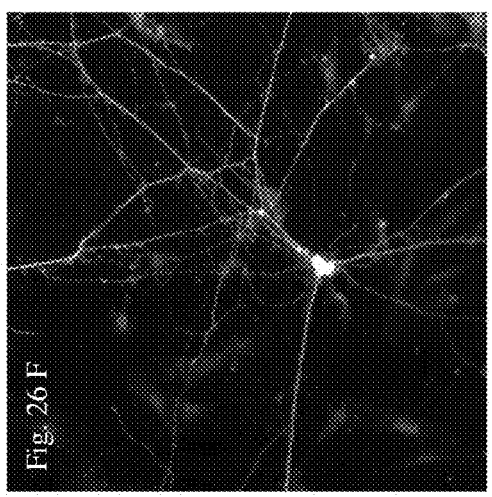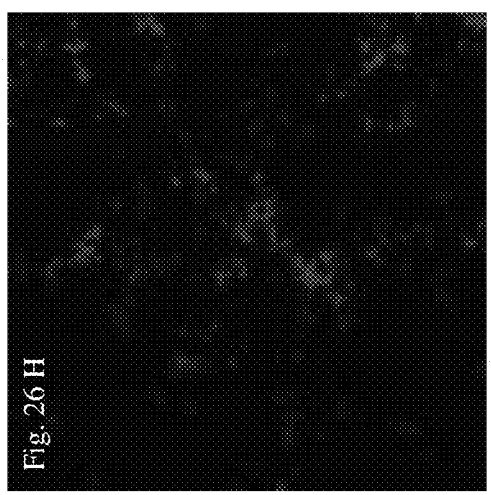
Figure 26F – 26I

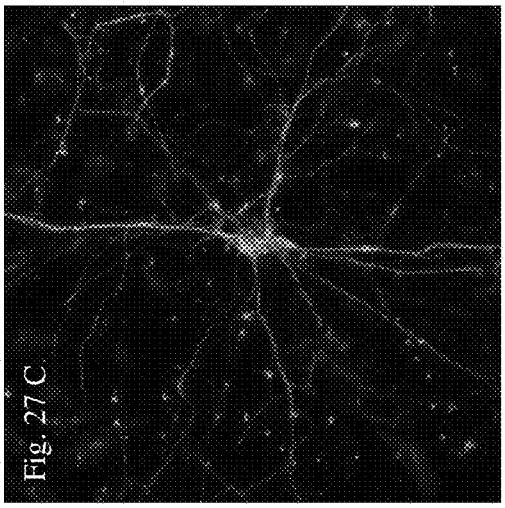
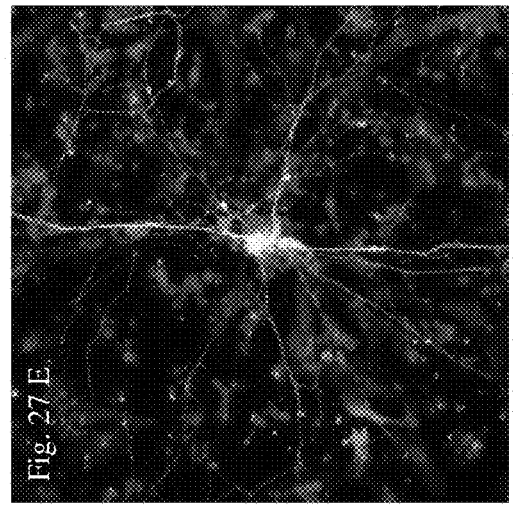
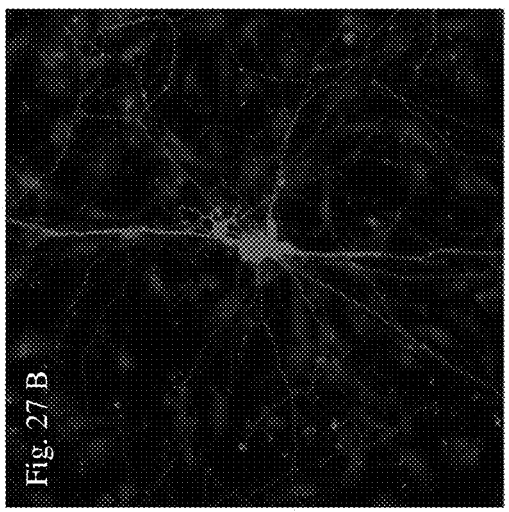
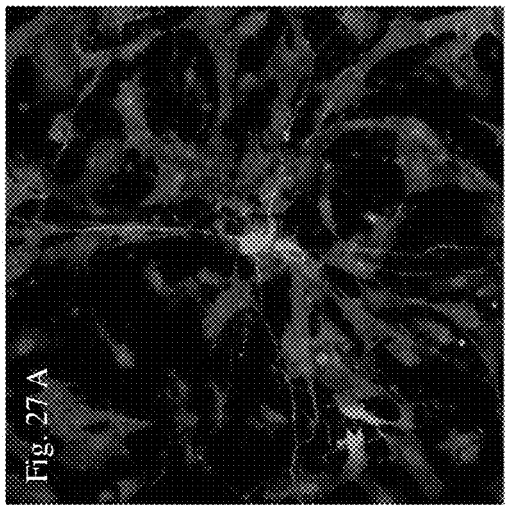
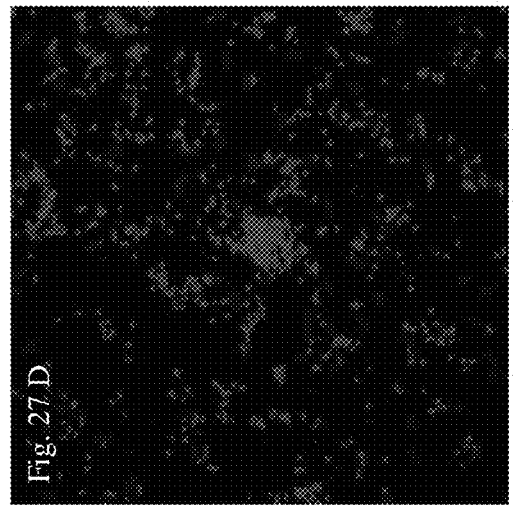
Figure 27A – 27E. Protocol B, with all-trans retinoic acid, solubilized in Albumax, plus 2-phospho-ascorbic acid and L-ascorbic acid Protocol B, with all-trans retinoic acid, solubilized in Albumax, plus 2-phospho-ascorbic acid and L-ascorbic acid

METHODS FOR DERIVING DOPAMINERGIC NEURONS FROM PLURIPOTENT STEM CELLS

BACKGROUND OF THE INVENTION

1. Field of the Invention

The present application relates to method of differentiating pluripotent stem cells to dopaminergic neurons. The present application also relates to treating or preventing diseases associated with grafting the dopaminergic neuronal cells obtained thereby to a patient.

2. General Background and State of the Art

The development of stem cell-derived dopaminergic neurons for the treatment of Parkinson's disease has been a major area of focus for regenerative medicine. Although there has been one clinical trial (Jun Takahashi, Japan), there remain serious technical challenges that have thus far prevented FDA approval of human trials in the US. These technical challenges could render treatment of Parkinson's disease with stem cell derived dopaminergic neurons impractical.

One issue is that embryonic stem cells (ESCs) more readily differentiate into the desired cell type than induced pluripotent stem cells (iPSCs). Embryonic stem cells often produce terminally differentiated cells that are more functional than cells derived from iPSCs. However, regulatory approval requires generating a large stock of the same ESCs, a master cell bank, that is used to generate all Investigational New Drug enabling experimental data and then used to treat the patients. Past efforts show that ESCs acquire karyotype abnormalities and become unstable after the many passages that are required to generate a source cell bank, perform all required experiments and then use for clinical testing in humans. In addition, many countries have now banned the use of embryonic stem cells for research or treatment.

iPSCs are more practical from the standpoint of regulatory approval because each treatment is patient specific and typically generated form his or her own cells. Therefore, there is no master cell bank. However, iPSCs to date have not differentiated into functional cells as well as embryonic stem cells. Clonal restriction is a major problem for differentiating iPSCs into a desired cell type. That is to say that one iPSC clone may be able to form neurons, while another clone cannot. More subtly, one clone may form really good neurons or hepatocytes, while other clones may express characteristic molecular markers but do not function as well as others or as well as naturally occurring cells. Often many clones must be tested to determine which clone is able to differentiate into a specific cell type. There is significant scientific evidence supporting the idea that clonal restriction is due to cell fate decisions that primed state stem cells have already made. Cells that have been induced to become pluripotent still retain some molecular marks, such as methylation or acetylation, that restrict what that cell clone can mature into.

These basic challenges of developing stem cell derived therapeutics become more problematic when developing dopaminergic neurons for the treatment of Parkinson's disease.

Parkinson's patients are on average 65 years old when they first need treatment. If the dopaminergic neurons are derived from donor embryonic stem cells, then patient needs to be on immune-suppressives for some period of time to prevent rejection of donor cells. This is not a good age for patient to be put on immune-suppressives.

In addition, current methods for generating dopaminergic neurons from stem cells produce neurons with very low engraftment rates. For Parkinson's disease, it is thought that 100,000 cells need to engraft to get a therapeutic benefit. Because of low engraftment rates, 10X-100X more cells neurons need to be transplanted to achieve a therapeutic benefit. That means that 1,000,000-10,000,000 cells need to be transplanted, which is a technical challenge using existing methods for differentiating stem cells into dopaminergic neurons. It has been reported that when generating dopaminergic neurons from human iPS cells, only about 3% of the yield are truly dopaminergic neurons. In order to get a pure population of dopaminergic neurons from iPSCs, researchers have needed to sort cells for specific molecular markers, such as Corin and LRTM1, early on in the differentiation process. These researchers showed that dopaminergic neurons or their precursors, that had been sorted for Corin+ and LRTM1+, had a higher percentage of cells that were TH positive and also showed about 10-times greater potential for engraftment than non-sorted cells a more pure population (Samata and Takahashi 2016, DOI: 10.1038/ncomms13097). Still the dopaminergic neurons or their precursors had to be transplanted at an early timepoint, Day 28, and even then only about 10% of the transplanted cells were present 3 months after transplantation.

To overcome the problem of low engraftment of stem cell derived dopaminergic neurons, dopaminergic neurons are being transplanted early, between Day 15 and 32 of differentiation, when they are in a precursor stage. Experiments have shown that engraftment of the immature neurons greatly increases engraftment, probably because the host brain provides unknown factors that are required for efficient engraftment. However, transplantation of early progenitor cells raises concerns with regulatory agencies, such as the USFDA.

The USFDA, as well as regulatory agencies in other countries, require characterization of the cells destined for implantation. For example, characterization of dopaminergic neurons for the treatment of Parkinson's disease would be expected to include demonstration that the cells produce dopamine. However, the early cells (~day 15-20) that are implanted to ensure adequate engraftment and expansion, do not yet secrete dopamine or even the final molecular markers that identify them as dopaminergic neurons. In addition, the early cell population may contain pluripotent stem cells that could give rise to a teratoma tumor in the recipient's brain.

If the USFDA applies the same acceptance criteria to cells for the treatment Parkinson's disease that they impose on other cellular therapies, it is hard to see how the early implantation of dopaminergic neurons or their precursors would be acceptable. FDA could be expected to require that cells for therapeutic use meet certain release criteria. That is to say that the manufactured cells would need to reproducibly express specific molecular markers and demonstrate potency, for example secrete a specific range of dopamine. Current methods for generating stem cell derived dopaminergic neurons plus early implantation make it impossible to fully characterize the cellular product and to show potency before implantation.

Thus, it would be an improvement to the state of the art to develop methods, including formulations, that efficiently and reproducibly induce stem cells to differentiate into dopaminergic neurons, or their precursors, that have improved survival, improved engraftment potential, improved yields and that also secrete increased amounts of dopamine. It would be a significant improvement over the state of the art if methods were developed that increased the efficiency, purity, yield and/or dopamine secreted from human iPS cells. Dopaminergic neurons derived from iPSCs would eliminate the need for treating patient with immunosuppressives and would negate the need for a master cell bank of embryonic donor cells.

The current strategy for cellular therapy for Parkinson's Disease is to differentiate stem cells into precursors of dopaminergic neurons and transplant into the appropriate region of the brain before final maturation into dopamine producing neurons. The reason for early transplantation of dopaminergic neurons, or their precursors, is that the local environment within the brain provides unknown factors that are required for the final maturation steps of precursors into functional dopaminergic neurons that have neuro-transport capability, engraft, and that produce and secrete dopamine.

Currently, stem cell derived dopaminergic neurons, or more specifically their precursors, need to be engrafted into the brain before they are completely developed. Experiments indicate that early transplantation results in higher engraftment rates and more benefit, presumably because of increased dopamine production. The dopaminergic neurons or precursors are transplanted at a pre-dopamine production stage so that unknown factors in the local environment of the brain induce proper maturation to the dopamine producing stage.

A drawback of the method of early engraftment of dopaminergic neurons or progenitors is that the cells cannot be fully characterized. For the treatment of humans with cellular therapies, the US FDA requires that cells are characterized and can only be "released" for administration to humans if certain pre-determined criteria are met. Based on FDA release criteria requirements for other cellular therapies, criteria such as a defined percent of the cells expressing certain molecular markers and a specific amount of dopamine produced by 1M cells are expected.

Thus, it would be a significant improvement to the state of the art if stem cell derived dopaminergic neurons could be cultured in vitro reliably and reproducibly to a stage when high percentages of the cells for transplant express definitive molecular markers and when significant amounts of dopamine are being produced. Lastly, these cells should demonstrate in vitro a capacity for engraftment into the brain.

Thus, it would be a significant improvement to the state of the art to identity the factors that are provided by the brain that induce the steps of maturation of dopaminergic neurons as well as the timeframe in which dopaminergic neuron precursors should be contacted with those factors.

SUMMARY OF THE INVENTION

The present invention is directed to a method of producing dopaminergic neurons from human stem cells comprising a step of adding or increasing concentration of vitamin into neuro basal media at approximately Day 20+/−3 of a protocol for differentiating pluripotent stem cells into dopaminergic neurons. The protocol may be Protocol A. The vitamin may be vitamin A, such as retinol, retinyl acetate, 9-cis retinoic acid, 13-cis retinoic acid or all-trans retinoic acid. Vitamin A may be solubilized in a lipid rich formulation such as human serum albumin, Albumax, non-human serum albumin. In one embodiment, vitamin A may be in a final concentration of from 1 uM to 3 uM.

Alternatively in accordance with above, the vitamin may be vitamin B6. Vitamin B6 may be in the form of pyridoxine, pyridoxal, or pyridoxal-5'-phosphate, also known as PLP. In one embodiment, vitamin B6 may be in a final concentration of from 10 uM to 30 uM.

Alternatively in accordance with the above, the vitamin may be vitamin C. Vitamin C may be in the form of 2-phospho-ascorbic acid or L-ascorbic acid. In one embodiment, vitamin C may be in a final concentration of from 200 nM to 110 uM.

In any of the methods above, the pluripotent stem cells to be differentiated may have been cultured in NME7-AB, or WNT3A. In another aspect, the pluripotent stem cells to be differentiated may be in a naïve state.

In accordance with the above, the produced dopaminergic neuron may be characterized by expressing greater than 30%, 100%, 500% or 1000% more dopamine than dopaminergic neurons produced by a differentiation protocol without added or increased vitamin.

In accordance with the above, the produced dopaminergic neuron is characterized by forming greater than 30%, 100%, 500% or 1000% more neurites than dopaminergic neurons produced by a differentiation protocol without added or increased vitamin.

The present invention is also directed to a method of increasing likelihood of successful grafting of dopaminergic neurons to a subject in need thereof comprising administering to the subject the dopaminergic neurons obtained in the method described above.

The present invention is also directed to a method of treating a central nervous system disease in a patient for which engraftment of dopamine producing neural cells is desired, comprising engrafting dopaminergic neurons obtained in the method described above to a person in need thereof. The central nervous system disease is Parkinson's Disease, Huntington's Disease, multiple sclerosis or Alzheimer's Disease. Injuries to the central nervous system and peripheral nervous system may be treated as well by engrafting neurons to the injured site, dopaminergic neurons for central nervous system condition and other types for neurons to treat peripheral nerve injury.

BRIEF DESCRIPTION OF THE DRAWINGS

The patent or application file contains at least one drawing executed in color. Copies of this patent or patent application publication with color drawings will be provided by the Office upon request and payment of the necessary fee.

The present invention will become more fully understood from the detailed description given herein below, and the accompanying drawings which are given by way of illustration only, and thus are not limitative of the present invention, and wherein;

FIG. 1A-1E shows schematics of four different protocols that were used to differentiate pluripotent stem cells into dopaminergic neurons. FIG. 1A is a schematic of a protocol published in a patent application US2018/0094242A1 (the contents of which are incorporated by reference herein regarding the disclosure of media to differentiate pluripotent stem cells into dopaminergic neurons) and referred to herein as Protocol A. FIG. 1B is a schematic of a new and improved protocol developed by the inventors, referred to here as Protocol B, in which from Day 21 and onward, pyridoxal is added at a final concentration of 11 uM bringing the total concentration in the media to about 21 uM pyridoxal. FIG. 1C is a schematic of a new and improved protocol developed by the inventors, referred to here as Protocol C, in which from Day 21 and onward, to a base neural media are added various forms of vitamin A, vitamin B and in some cases vitamin C; FIG. 1D shows a schematic of Protocol C.2, in which at Day 21 and onward, the base neural media is exchanged with one that does not contain pyridoxal but instead contains pyridoxine at a final concentration of 16 uM plus retinol at a final concentration of 1.2 uM and retinyl acetate at a final concentration of 0.17 uM. FIG. 1E is a schematic of an optimized protocol, Protocol D, in which at Day 21 and onward, the base media that contains about 10 uM pyridoxal is supplemented with an additional 11 uM pyridoxal, retinol at 1.2 uM, retinyl acetate at 0.17 uM, 2-phospho-ascorbic acid at 61 uM and L-ascorbic acid at 11 uM. SHH: sonic hedgehog; FGF: fibroblast growth factor; BDNF: brain-derived neurotrophic factor; GDNF: glial cell-derived neurotrophic factor; AA: ascorbic acid; TGFβ: transforming growth factor beta; cAMP: cyclic adenosine monophosphate.

FIG. 2A-2D show fluorescent photographs of human embryonic stem cells, HES3 commercially available cells, referred to here as $hES_{E8-HES3}$, which before differentiation had been cultured in E8 media. FIG. 2E-2H show fluorescent photographs of human induced pluripotent stem cells, referred to here as $iPS_{E8-A6}$, which before differentiation had been cultured in E8 media. FIG. 2I-2L show fluorescent photographs of human induced pluripotent stem cells, referred to here as $iPS_{NME7-6E}$, which before differentiation had been cultured in $NME7_{AB}$ naïve media. FIGS. 2A, 2E, and 2I show cells that were stained for the presence of GIRK2 (G-protein-regulated inward-rectifier potassium channel 2) which is expressed in dopaminergic neurons. FIGS. 2B, 2F, and 2J show cells that were stained for the presence of TH (tyrosine hydroxylase) which is considered a gold standard in the identification of dopaminergic neurons. FIGS. 2C, 2G, and 2K show cells that were stained for the presence of show cells that were stained for the presence of Tuj1 (neuron-specific class Ill B-tubulin) which is a pan-neural marker. FIGS. 2D, 2H, and 2L show overlays of all three markers.

FIG. 3A-3D show fluorescent photographs of human embryonic stem cells, HES3 commercially available cells, referred to here as $hES_{E8-HES3}$, which before differentiation had been cultured in E8 media. FIG. 3E-3H show fluorescent photographs of human induced pluripotent stem cells, referred to here as $iPS_{E8-A6}$, which before differentiation had been cultured in E8 media. FIG. 3I-3L show fluorescent photographs of human induced pluripotent stem cells, referred to here as $iPS_{NME7-6E}$, which before differentiation had been cultured in NME7AB naïve media. FIGS. 3A, 3E, and 3I show cells that were stained for the presence of GIRK2 (G-protein-regulated inward-rectifier potassium channel 2) which is expressed in dopaminergic neurons. FIGS. 3B, 3F, and 3J show cells that were stained for the presence of TH (tyrosine hydroxylase) which is considered a gold standard in the identification of dopaminergic neurons. FIGS. 3C, 3G, and 3K show cells that were stained for the presence of show cells that were stained for the presence of Tuj1 (neuron-specific class Ill B-tubulin) which is a pan-neural marker. FIGS. 3D, 3H, and 3L show overlays of all three markers.

FIGS. 4A, 4B, 4E, 4F, 4G and 4H show images of cells differentiated from $iPS_{NME7-N7B}$ naïve stem cells that were reprogrammed using the episomal method. FIGS. 4C and 4D show images of cells differentiated from $iPS_{E8-A6}$ stem cells. FIG. 4A-4B were differentiated according to Protocol A. FIG. 4E-4F were differentiated according to Protocol C.2. FIGS. 4C-4D and 4G-4H were differentiated according to Protocol C.2, except that for 48 hours before starting differentiation protocol, WNT3A was added to the respective pluripotency media, at 100 ng/mL. FIGS. 4A, 4E, 4C, and 4G show cells stained for the presence of DAT (dopamine active transporter) and Tuj1. FIGS. 4B, 4F, 4D, and 4H show cells stained for the presence of GIRK2, TH, and Tuj1.

FIG. 5A-5C shows photographs of $iPS_{NME7-6E}$ derived neurons. FIG. 5D-5F shows photographs of $iPS_{E8-A6}$ derived neurons.

FIG. 6A-6B show dopamine secreted from cells differentiated to dopaminergic neurons according to Protocol A. FIG. 6C-6D show dopamine secreted from cells differentiated to dopaminergic neurons according to Protocol C.2. FIG. 6A, 6C shows dopaminergic neurons derived from $iPS_{E8-A6}$ primed state stem cells. FIG. 6B, 6D shows dopaminergic neurons derived from $iPS_{NME7-6E}$ naïve state stem cells.

FIG. 8 is a table that shows the amount of dopamine and its metabolites that is secreted by a varying number of human stem cell derived dopaminergic neurons. The table is organized according to the starting stem cell type. Stem cells were either primed state embryonic "HES3" cells, primed state induced pluripotent stem cells $iPS_{E8-A6}$ cells, naïve state induced pluripotent stem cells generated with Sendai virus "$iPS_{NME7-6E}$", or naïve state induced pluripotent stem cells generated with episomal technology "$iPS_{NME7-N7B}$". In some cases, as indicated in the table, stem cells were cultured in their respective media to which was added WNT3A, at 100 ng/mL, for 48 hours before initiation of differentiation.

FIG. 10 is a table that shows the amount of dopamine and its metabolites that is secreted by episomal naïve clone iPS$_{NME7-6E}$. Day 11 number of cells plated is varied, as well as the Day number when dopamine secretion is measured. Additionally, in some cases, where indicated, WNT3A was added to culture media at 100 ng/mL for 48 hours before initiation of differentiation.

FIG. 11A-11K shows fluorescent photographs taken at 20× magnification on a confocal microscope of human iPS cells at Day 24 of differentiation to dopaminergic neurons according to the protocol described here as Protocol A, albeit with the modification that around Day 20 of the protocol, vitamin A in the form of retinol and retinyl acetate have been introduced into the media until cell harvest. These cells served as a control for investigating the effect of adding various forms of vitamin B6 at about Day 20 of the protocol. FIG. 11A shows fluorescent photograph of cells stained for GIRK2. FIG. 11B shows fluorescent photograph of cells stained for TH, tyrosine hydroxylase. FIG. 11C shows fluorescent photograph of cells stained for Tuj1.

FIG. 11D shows fluorescent photograph of cells stained with Hoechst dye to show nuclei. FIG. 11E shows the bright field image. FIG. 11F shows the fluorescent photograph of the overlay of GIRK2, TH, Tuj1, and Hoechst. FIG. 11G shows fluorescent photograph of the cells stained for DAT, dopamine transporter protein. FIG. 11H shows fluorescent photograph of cells stained for Tuj1. FIG. 11I shows fluorescent photograph of cells stained with Hoechst dye to show nuclei. FIG. 11J shows the bright field image. FIG. 11K shows the fluorescent photograph of the overlay of DAT, Tuj1, and Hoechst.

FIG. 12A-12K shows fluorescent photographs taken at 20× magnification on a confocal microscope of human iPS cells at Day 24 of differentiation to dopaminergic neurons according to the protocol described here as Protocol A, except that around Day 20, vitamin A in the form of retinol and retinyl acetate have been introduced into the media until cell harvest. In this experiment, vitamin B6 in the form of pyridoxine was added to a final concentration of 16 uM. FIG. 12A shows fluorescent photograph of cells stained for GIRK2. FIG. 12B shows fluorescent photograph of cells stained for TH, tyrosine hydroxylase. FIG. 12C shows fluorescent photograph of cells stained for Tuj1. FIG. 12D shows fluorescent photograph of cells stained with Hoechst dye to show nuclei. FIG. 12E shows the bright field image. FIG. 12F shows the fluorescent photograph of the overlay of GIRK2, TH, Tuj1, and Hoechst. FIG. 12G shows fluorescent photograph of the cells stained for DAT, dopamine transporter protein. FIG. 12H shows fluorescent photograph of cells stained for Tuj1. FIG. 12I shows fluorescent photograph of cells stained with Hoechst dye to show nuclei. FIG. 12J shows the bright field image. FIG. 12K shows the fluorescent photograph of the overlay of DAT, Tuj1, and Hoechst.

FIG. 13A-13K shows fluorescent photographs taken at 20× magnification on a confocal microscope of human iPS cells at Day 24 of differentiation to dopaminergic neurons according to the protocol described here as Protocol A, except that around Day 20, vitamin A in the form of retinol and retinyl acetate have been introduced into the media until cell harvest. In this experiment, vitamin B6 in the form of pyridoxal was added to a final concentration of 11 uM. FIG. 13A shows fluorescent photograph of cells stained for GIRK2. FIG. 13B shows fluorescent photograph of cells stained for TH, tyrosine hydroxylase. FIG. 13C shows fluorescent photograph of cells stained for Tuj1. FIG. 13D shows fluorescent photograph of cells stained with Hoechst dye to show nuclei. FIG. 13E shows the bright field image. FIG. 13F shows the fluorescent photograph of the overlay of GIRK2, TH, Tuj1, and Hoechst. FIG. 13G shows fluorescent photograph of the cells stained for DAT, dopamine transporter protein. FIG. 13H shows fluorescent photograph of cells stained for Tuj1. FIG. 13I shows fluorescent photograph of cells stained with Hoechst dye to show nuclei. FIG. 13J shows the bright field image. FIG. 13K shows the fluorescent photograph of the overlay of DAT, Tuj1, and Hoechst.

FIG. 14A shows fluorescent photograph of cells stained for GIRK2. FIG. 14B shows fluorescent photograph of cells stained for TH, tyrosine hydroxylase. FIG. 14C shows fluorescent photograph of cells stained for Tuj1. FIG. 14D shows fluorescent photograph of cells stained with Hoechst dye to show nuclei. FIG. 14E shows the bright field image. FIG. 14F shows the fluorescent photograph of the overlay of GIRK2, TH, Tuj1, and Hoechst. FIG. 14G shows fluorescent photograph of the cells stained for DAT, dopamine transporter protein. FIG. 14H shows fluorescent photograph of cells stained for Tuj1. FIG. 14I shows fluorescent photograph of cells stained with Hoechst dye to show nuclei. FIG. 14J shows the bright field image. FIG. 14K shows the fluorescent photograph of the overlay of DAT, Tuj1, and Hoechst.

FIG. 15A-15K shows fluorescent photographs taken at 20× magnification on a confocal microscope of human iPS cells at Day 24 of differentiation to dopaminergic neurons according to the protocol described here as Protocol A, except that around Day 20, vitamin A in the form of retinol and retinyl acetate have been introduced into the media until cell harvest. In this experiment, all three forms of vitamin B6 were added as pyridoxine-HCL, pyridoxal, and pyridoxal-5'-phosphate, also known as PLP. FIG. 15A shows fluorescent photograph of cells stained for GIRK2. FIG. 15B shows fluorescent photograph of cells stained for TH, tyrosine hydroxylase. FIG. 15C shows fluorescent photograph of cells stained for Tuj1. FIG. 15D shows fluorescent photograph of cells stained with Hoechst dye to show nuclei. FIG. 15E shows the bright field image. FIG. 15F shows the fluorescent photograph of the overlay of GIRK2, TH, Tuj1, and Hoechst. FIG. 15G shows fluorescent photograph of the cells stained for DAT, dopamine transporter protein. FIG. 15H shows fluorescent photograph of cells stained for Tuj1. FIG. 15I shows fluorescent photograph of cells stained with Hoechst dye to show nuclei. FIG. 15J shows the bright field image. FIG. 15K shows the fluorescent photograph of the overlay of DAT, Tuj1, and Hoechst.

FIG. 16A shows fluorescent photograph of cells when pyridoxine-HCL was added to a final concentration of 16 uM beginning on Day 20. FIG. 16B shows fluorescent photograph of cells when pyridoxal was added to a final concentration of 11 uM beginning on Day 20. FIG. 16C shows fluorescent photograph of cells when pyridoxal-5'-phosphate was added to a final concentration of 20 uM beginning on Day 20. FIG. 16D shows fluorescent photograph of cells when all three B6 vitamins are added together, including pyridoxine, pyridoxal and pyridoxal-5'-phosphate. FIG. 16E shows the control experiment according to Protocol A, except that vitamins A in the form of retinol and retinyl acetate were added at Day 20.

FIG. 18A shows fluorescent photograph of cells stained for GIRK2. FIG. 18B shows fluorescent photograph of cells stained for TH, tyrosine hydroxylase. FIG. 18C shows fluorescent photograph of cells stained for Tuj1. FIG. 18D shows fluorescent photograph of cells stained with Hoechst dye to show nuclei. FIG. 18E shows the fluorescent photograph of the overlay of GIRK2, TH, Tuj1, and Hoechst. FIG. 18F shows fluorescent photograph of the cells stained for DAT, dopamine transporter protein. FIG. 18G shows fluorescent photograph of cells stained for Tuj1. FIG. 18H shows fluorescent photograph of cells stained with Hoechst dye to show nuclei. FIG. 18I shows fluorescent photograph of the overlay of DAT, Tuj1, and Hoechst.

FIG. 19A shows fluorescent photograph of cells stained for GIRK2. FIG. 19B shows fluorescent photograph of cells stained for TH, tyrosine hydroxylase. FIG. 19C shows fluorescent photograph of cells stained for Tuj1. FIG. 19D shows fluorescent photograph of cells stained with Hoechst dye to show nuclei. FIG. 19E shows the fluorescent photograph of the overlay of GIRK2, TH, Tuj1, and Hoechst. FIG. 19F shows fluorescent photograph of the cells stained for DAT, dopamine transporter protein. FIG. 19G shows fluorescent photograph of cells stained for Tuj1. FIG. 19H shows fluorescent photograph of cells stained with Hoechst dye to show nuclei. FIG. 19I shows fluorescent photograph of the overlay of DAT, Tuj1, and Hoechst.

FIG. 20A shows fluorescent photograph of cells stained for GIRK2. FIG. 20B shows fluorescent photograph of cells stained for TH, tyrosine hydroxylase. FIG. 20C shows fluorescent photograph of cells stained for Tuj1. FIG. 20D shows fluorescent photograph of cells stained with Hoechst dye to show nuclei. FIG. 20E shows the fluorescent photograph of the overlay of GIRK2, TH, Tuj1, and Hoechst. FIG. 20F shows fluorescent photograph of the cells stained for DAT, dopamine transporter protein. FIG. 20G shows fluorescent photograph of cells stained for Tuj1. FIG. 20H shows fluorescent photograph of cells stained with Hoechst dye to show nuclei. FIG. 20I shows fluorescent photograph of the overlay of DAT, Tuj1, and Hoechst.

FIG. 21A-21I shows fluorescent photographs taken at 20× magnification on a confocal microscope of human iPS cells at Day 24 of differentiation to dopaminergic neurons, according to Protocol B. In this experiment, in addition to pyridoxal being added to the media from Day 20 onward, the following forms of vitamin A were added: 9-cis retinoic acid to a final concentration of 0.446 uM; 13-cis retinoic acid to a final concentration of 0.446 uM; and all-trans retinoic acid to a final concentration of 0.446 uM. FIG. 21A shows fluorescent photograph of cells stained for GIRK2. FIG. 21B shows fluorescent photograph of cells stained for TH, tyrosine hydroxylase. FIG. 21C shows fluorescent photograph of cells stained for Tuj1. FIG. 21D shows fluorescent photograph of cells stained with Hoechst dye to show nuclei. FIG. 21E shows the fluorescent photograph of the overlay of GIRK2, TH, Tuj1, and Hoechst. FIG. 21F shows fluorescent photograph of the cells stained for DAT, dopamine transporter protein. FIG. 21G shows fluorescent photograph of cells stained for Tuj1. FIG. 21H shows fluorescent photograph of cells stained with Hoechst dye to show nuclei. FIG. 21I shows fluorescent photograph of the overlay of DAT, Tuj1, and Hoechst.

FIG. 22A-22I shows fluorescent photographs taken at 20× magnification on a confocal microscope of human iPS cells at Day 24 of differentiation to dopaminergic neurons, according to Protocol B. In this experiment, in addition to pyridoxal being added to the media from Day 20 onward, all-trans retinoic acid to a final concentration of 1.33 uM. FIG. 22A shows fluorescent photograph of cells stained for GIRK2. FIG. 22B shows fluorescent photograph of cells stained for TH, tyrosine hydroxylase. FIG. 22C shows fluorescent photograph of cells stained for Tuj1. FIG. 22D shows fluorescent photograph of cells stained with Hoechst dye to show nuclei. FIG. 22E shows the fluorescent photograph of the overlay of GIRK2, TH, Tuj1, and Hoechst. FIG. 22F shows fluorescent photograph of the cells stained for DAT, dopamine transporter protein. FIG. 22G shows fluorescent photograph of cells stained for Tuj1. FIG. 22H shows fluorescent photograph of cells stained with Hoechst dye to show nuclei. FIG. 22I shows fluorescent photograph of the overlay of DAT, Tuj1, and Hoechst.

FIG. 23A shows fluorescent photograph of cells that were differentiated according to Protocol A. FIG. 23B shows fluorescent photograph of cells differentiated according to Protocol B, but at Day 20, in addition to the pyridoxal being added, vitamin A in the form of retinol (0.7 uM) and retinyl acetate (0.6 uM) were added. FIG. 23C shows fluorescent photograph of cells differentiated according to Protocol B, but at Day 20, in addition to the pyridoxal being added, vitamin A in the form of 9-cis retinoic acid, 13-cis retinoic acid and all-trans retinoic acid, each at a final concentration of 0.446 uM, were added. FIG. 23D shows fluorescent photograph of cells differentiated according to Protocol B, but at Day 20, in addition to the pyridoxal being added, vitamin A in the form of all-trans retinoic acid was added to a final concentration of 1.33 uM. FIG. 23E shows the control experiment where cells were differentiated according to Protocol B, which differs from Protocol A in that at Day 20 and onward, pyridoxal was added to a final concentration of 11 uM.

FIG. 24A shows fluorescent photograph of cells stained for GIRK2. FIG. 24B shows fluorescent photograph of cells stained for TH, tyrosine hydroxylase. FIG. 24C shows fluorescent photograph of cells stained for Tuj1. FIG. 24D shows fluorescent photograph of cells stained with Hoechst dye to show nuclei. FIG. 24E shows the fluorescent photograph of the overlay of GIRK2, TH, Tuj1, and Hoechst. FIG. 24F shows fluorescent photograph of the cells stained for DAT, dopamine transporter protein. FIG. 24G shows fluorescent photograph of cells stained for Tuj1. FIG. 24H shows fluorescent photograph of cells stained with Hoechst dye to show nuclei. FIG. 24I shows fluorescent photograph of the overlay of DAT, Tuj1, and Hoechst.

FIG. 25A shows fluorescent photograph of cells stained for GIRK2. FIG. 25B shows fluorescent photograph of cells stained for TH, tyrosine hydroxylase. FIG. 25C shows fluorescent photograph of cells stained for Tuj1. FIG. 25D shows fluorescent photograph of cells stained with Hoechst dye to show nuclei. FIG. 25E shows the fluorescent photograph of the overlay of GIRK2, TH, Tuj1, and Hoechst. FIG. 25F shows fluorescent photograph of the cells stained for DAT, dopamine transporter protein. FIG. 25G shows fluorescent photograph of cells stained for Tuj1. FIG. 25H shows fluorescent photograph of cells stained with Hoechst dye to show nuclei. FIG. 25I shows fluorescent photograph of the overlay of DAT, Tuj1, and Hoechst.

FIG. 26A-26I shows fluorescent photographs taken at 20× magnification on a confocal microscope of human iPS cells at Day 24 of differentiation to dopaminergic neurons, according to Protocol B. In this experiment, in addition to pyridoxal being added to the media from Day 20 onward, vitamin A was added as all-trans retinoic acid to a final concentration of 1.33 uM, wherein it had been solubilized in Albumax at 2 mg/mL. FIG. 26A shows fluorescent photograph of cells stained for GIRK2. FIG. 26B shows fluorescent photograph of cells stained for TH, tyrosine hydroxylase. FIG. 26C shows fluorescent photograph of cells stained for Tuj1. FIG. 26D shows fluorescent photograph of cells stained with Hoechst dye to show nuclei. FIG. 26E shows the fluorescent photograph of the overlay of GIRK2, TH, Tuj1, and Hoechst. FIG. 26F shows fluorescent photograph of the cells stained for DAT, dopamine transporter protein. FIG. 26G shows fluorescent photograph of cells stained for Tuj1. FIG. 26H shows fluorescent photograph of cells stained with Hoechst dye to show nuclei. FIG. 26I shows fluorescent photograph of the overlay of DAT, Tuj1, and Hoechst.

FIG. 27A-27I shows fluorescent photographs taken at 20× magnification on a confocal microscope of human iPS cells at Day 24 of differentiation to dopaminergic neurons, according to Protocol B. In this experiment, in addition to pyridoxal being added to the media from Day 20 onward, vitamin A was added as all-trans retinoic acid to a final concentration of 1.33 uM, wherein it had been solubilized in Albumax at 2 mg/mL. Vitamin C was added as 2-phospho-ascorbic acid at 61 uM and L-ascorbic acid at 110 uM. FIG. 27A shows fluorescent photograph of cells stained for GIRK2. FIG. 27B shows fluorescent photograph of cells stained for TH, tyrosine hydroxylase. FIG. 27C shows fluorescent photograph of cells stained for Tuj1. FIG. 27D shows fluorescent photograph of cells stained with Hoechst dye to show nuclei. FIG. 27E shows the fluorescent photograph of the overlay of GIRK2, TH, Tuj1, and Hoechst. FIG. 27F shows fluorescent photograph of the cells stained for DAT, dopamine transporter protein. FIG. 27G shows fluorescent photograph of cells stained for Tuj1. FIG. 27H shows fluorescent photograph of cells stained with Hoechst dye to show nuclei. FIG. 27I shows fluorescent photograph of the overlay of DAT, Tuj1, and Hoechst.

DETAILED DESCRIPTION OF THE PREFERRED EMBODIMENTS

Definitions

Figures 1C, 1D:
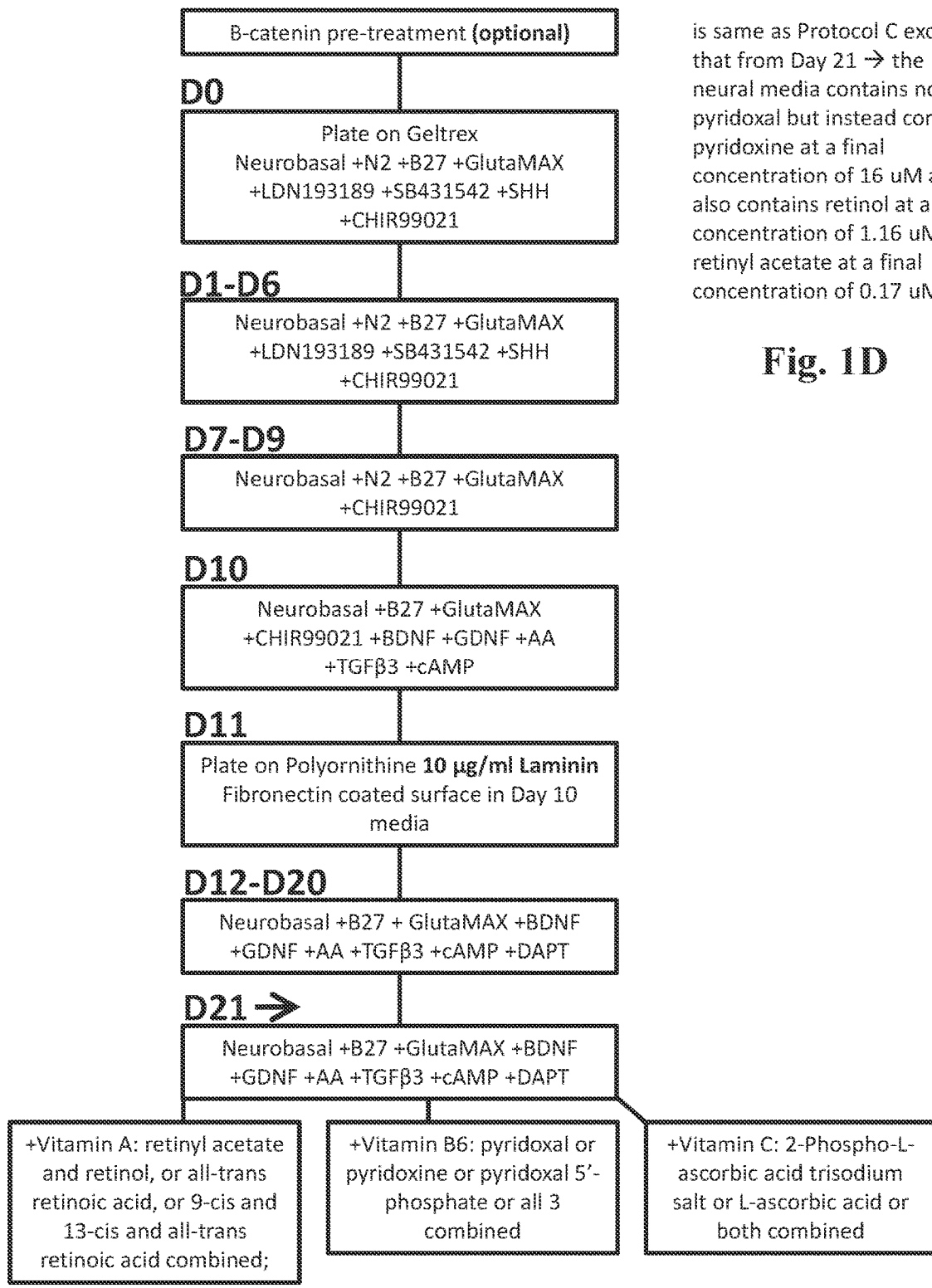
Figure 1E:
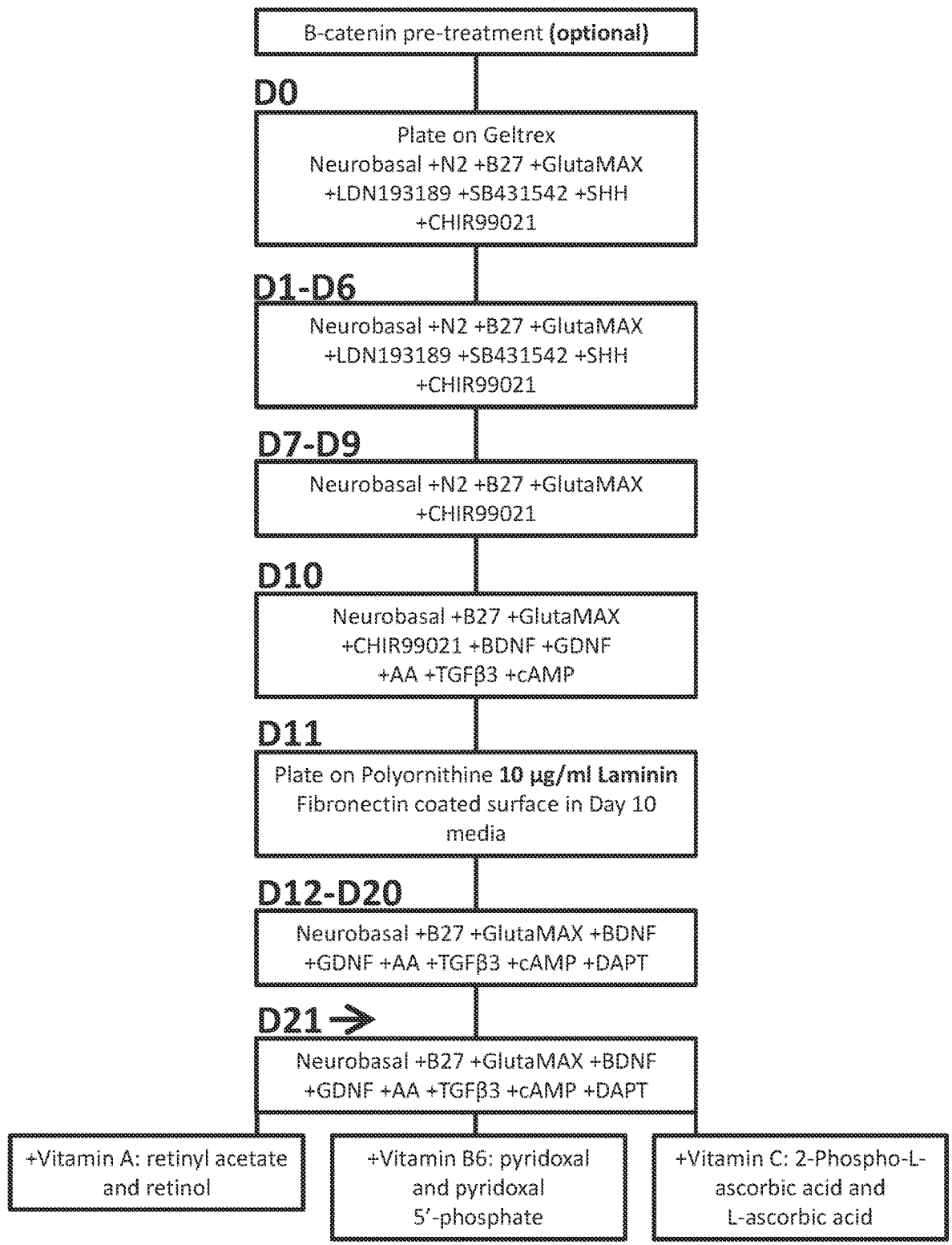
Figures 2A, 2B, 2C, 2D, 2E, 2F, 2G, 2H, 2I, 2J, 2K, 2L:
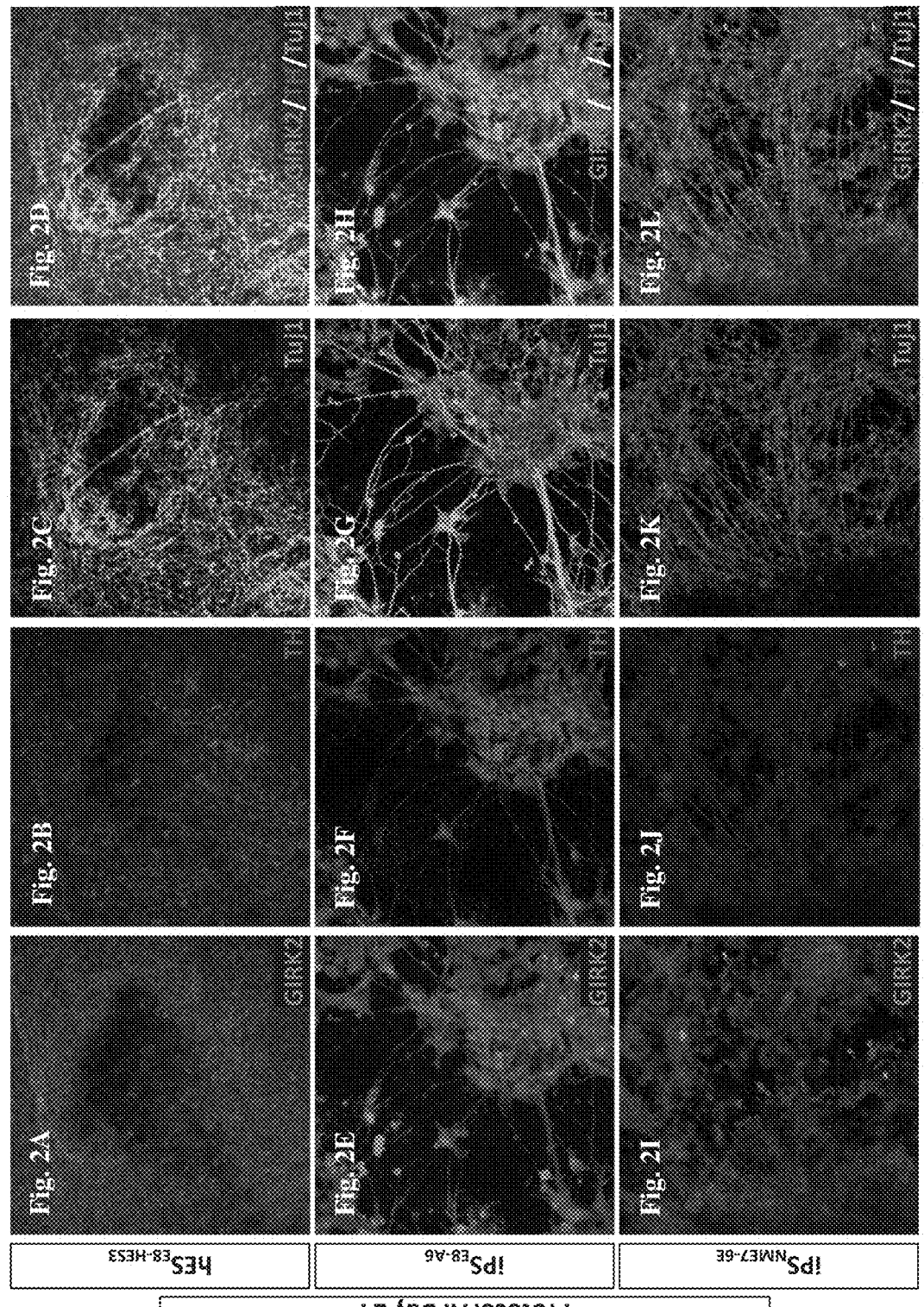
FIG. 2A-2L show fluorescent photographs taken on Day 24 of Protocol A of three different types of pluripotent stem cells that were cultured in different media, then differentiated to try to generate dopaminergic neurons.
Figures 3A, 3B, 3C, 3D, 3E, 3F, 3G, 3H, 3I, 3J, 3K, 3L:
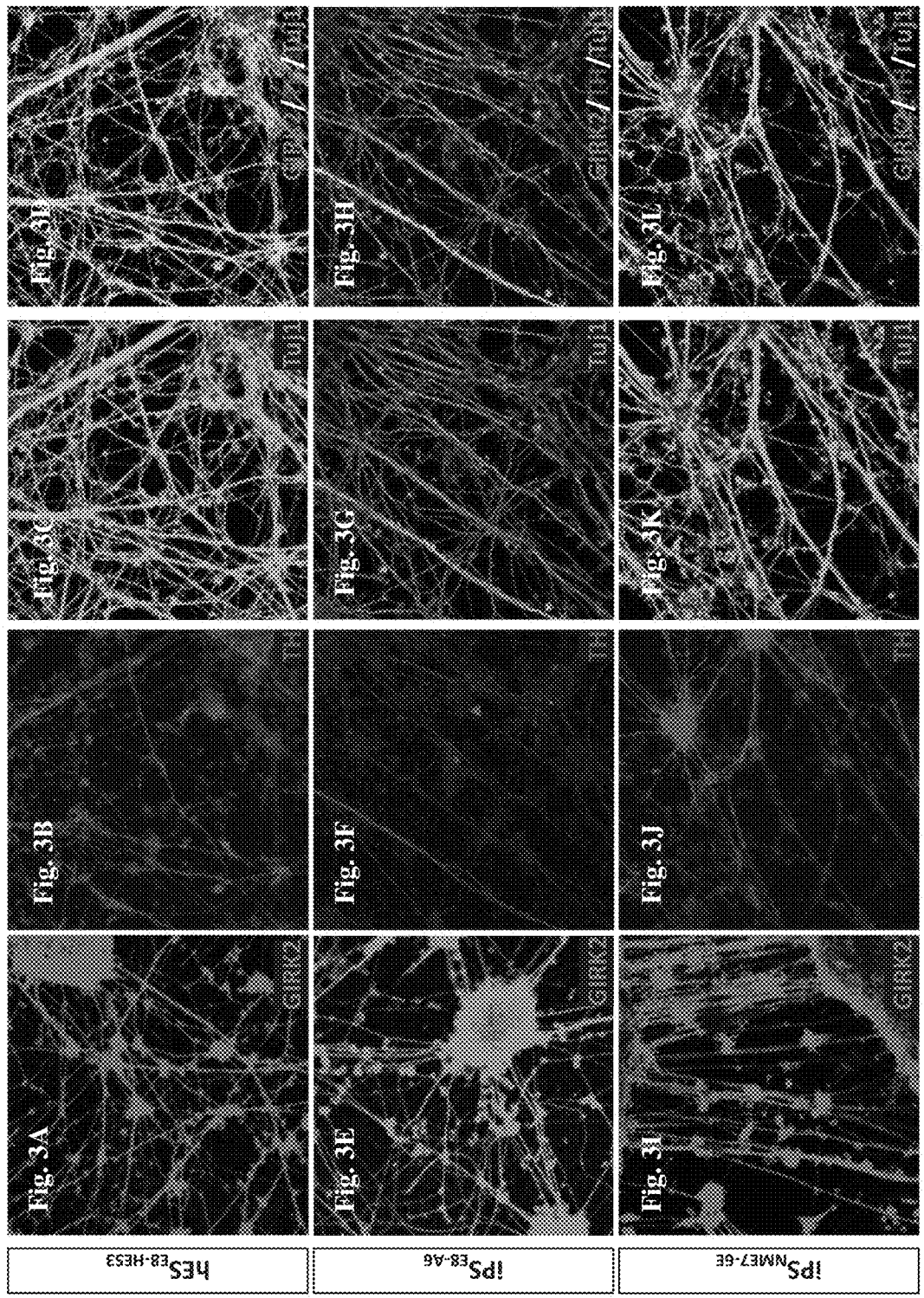
FIG. 3A-3L show fluorescent photographs taken on Day 24 of Protocol C.2 of three different types of pluripotent stem cells that were cultured in different media, then differentiated to try to generate dopaminergic neurons.

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present. The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, the term "a population of cells" or "a cell population" refers to a group of at least two cells. In non-limiting examples, a cell population can include at least about 10, at least about 100, at least about 200, at least about 300, at least about 400, at least about 500, at least about 600, at least about 700, at least about 800, at least about 900, at least about 1000 cells. The population may be a pure population comprising one cell type, such as a population of dopaminergic neurons, or a population of undifferentiated stem cells. Alternatively, the population may comprise more than one cell type, for example a mixed cell population.

As used herein, "amino acid" and "amino acids" refer to all naturally occurring L-α-amino acids. This definition is meant to include norleucine, ornithine, and homocysteine.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, the term "contacting" a cell or cells with a compound (e.g., one or more inhibitor, activator, and/or inducer) refers to providing the compound in a location that permits the cell or cells access to the compound. The contacting may be accomplished using any suitable method. For example, contacting can be accomplished by adding the compound, in concentrated form, to a cell or population of cells, for example in the context of a cell culture, to achieve the desired concentration. Contacting may also be accomplished by including the compound as a component of a formulated culture medium.

As used herein, the term "culture medium" refers to a liquid that covers cells in a culture vessel, such as a Petri plate, a multi-well plate, and the like, and contains nutrients to nourish and support the cells. Culture medium may also include growth factors added to produce desired changes in the cells.

As used herein, an "effective amount of an agent to inhibit an NME family member protein" refers to the effective amount of the agent in hindering the activating interaction between the NME family member protein and its cognate receptor such as As used herein, administration "in combination with" one or more further therapeutic agents includes simultaneous (concurrent) and consecutive administration in any order.

As used herein, the term "induced pluripotent stem cell" or "iPSC" refers to a type of pluripotent stem cell formed by the introduction of certain embryonic genes (such as but not limited to OCT4, SOX2, and KLF4 transgenes) (see, for example, Takahashi and Yamanaka Cell 126, 663-676 (2006), herein incorporated by reference) into a somatic cell.

As used herein, "multipotent" stem cells refer to stem cells that can differentiate into other cell types wherein the number of different cell types is limited.

As used herein, "Naïve stem cells" are those that resemble and share quantifiable characteristics with cells of the inner mass of a blastocyst. Naïve stem cells have quantifiable differences in expression of certain genes compared to primed stem cells, which resemble and share traits and characteristics of cells from the epiblast portion of a blastocyst. Notably, naïve stem cells of a female source have two active X chromosomes, referred to as XaXa, whereas the later primed stem cells of a female source have one of the X chromosomes inactivated.

As used herein, "neurobasal media" means medium that allows for long-term maintenance of the normal phenotype and growth of neuronal cells, and maintains pure populations of neuronal cells without the need for an astrocyte feeder layer.

As used herein, "NME family proteins" or "NME family member proteins", numbered 1-10, are proteins grouped together because they all have at least one NDPK (nucleotide diphosphate kinase) domain. In some cases, the NDPK domain is not functional in terms of being able to catalyze the conversion of ATP to ADP. NME proteins were formerly known as NM23 proteins, numbered H1 and H2. Recently, as many as ten (10) NME family members have been identified. Herein, the terms NM23 and NME are interchangeable. Herein, terms NME1, NME2, NME5, NME6, NME7, NME8 and NME9 are used to refer to the native protein as well as NME variants. In some cases, these variants are more soluble, express better in *E. coli* or are more soluble than the native sequence protein. For example, NME7 as used in the specification can mean the native protein or a variant, such as NME7AB that has superior commercial applicability because variations allow high yield expression of the soluble, properly folded protein in *E. coli*. NME7AB consists primarily of the NME7 A and B domains but is devoid of most of the DM10 domain, which is at the N-terminus of the native protein. "NME1" as referred to herein is interchangeable with "NM23-H1". It is also intended that the invention not be limited by the exact sequence of the NME proteins. NME7 as referred to herein is intended to mean native NME7 having a molecular weight of about 42 kDa. NME7$_{AB}$ as referred to herein is intended to mean either native or recombinant NME7 that is devoid of the DM-10 domain, having a molecular weight of about 33 kDa or an alternative native variant NME7-X1 that is also devoid of the DM-10 domain, having a molecular weight of about 31 kDa.

As used herein, the terms "NME7$_{AB}$", "NME7AB" and "NME-AB" are used interchangeably.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

As used herein, "pluripotency markers" are those genes and proteins whose expression is increased when cells revert to a less mature state than the starting cells. Pluripotency markers include OCT4, SOX2, NANOG, KLF4, KLF2, Tra 1-60, Tra 1-81, SSEA4, and REX-1 as well as others previously described and those currently being discovered. For example, fibroblast cells express no detectable or low levels of these pluripotency markers, but express a fibroblast differentiation marker called CD13. To determine if a cell is becoming less mature than the starting cells, one could measure a difference in the expression levels of the pluripotency markers between the starting cells and the resultant cells.

As used herein, "pluripotent" stem cell refers to stem cells that can differentiate to all three germlines, endoderm, ectoderm and mesoderm, to differentiate into any cell type in the body, but cannot give rise to a complete organism. A totipotent stem cell is one that can differentiate or mature into a complete organism such as a human being. With reference to embryonic pluripotent stem cells, they are cells derived from the inner cell mass of a blastocyst. Typical markers of pluripotency are OCT4, KLF4, NANOG, Tra 1-60, Tra 1-81 and SSEA4.

As used herein, "primed stem cells" are cells that resemble and share traits and characteristics of cells from the epiblast portion of a blastocyst.

As used herein, "semi-dopaminergic neuronal state" or "pre-dopaminergic neuronal state" of a population of cells or "dopaminergic neuron precursors" refers to a population of cells in which some or all of the cells have morphological characteristics and dopamine expression levels of a dopaminergic neuron, however the population of cells contains at least some cells that are not fully mature dopaminergic neurons.

As used herein, the term "stem cell" refers to a cell with the ability to divide for indefinite periods in culture and to give rise to specialized cells.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

Differentiating Pluripotent Stem Cells to
Dopaminergic Neurons

In this body of work the inventors explored two major lines of research: 1) comparison of the potential of naïve stem cells versus primed state stem cells to differentiate into functional dopaminergic neurons; and 2) the effect of the time-dependent addition of various factors, including vitamins produced in the brain of developing embryo, on the differentiation of functional dopaminergic neurons.

We first directed human iPS cells to differentiate into dopaminergic neurons using a protocol derived from US2018/0094242A1, referred to herein as Protocol A (FIG. 1A and Example 1). In these experiments, the starting iPSCs were either in the earliest naïve state, having been grown in NME7-AB naïve media (Carter et al 2016), or in the later primed state, having been grown in FGF2-containing E8 media. Using Protocol A and starting with either hESCs or hiPSCs that were in the primed state, having been cultured in FGF2 containing E8 media, the resultant dopaminergic neurons secreted only about 2-3 ng/mL of dopamine or its metabolites per 800,000 cells per $cm^2$ at Day 60 of the protocol. In contrast, using Protocol A but starting with naïve state hiPSCs, at Day 60, in one case they secreted 8.45 ng/mL dopamine and metabolites from 400,000 cells per cm2 and in another case they secreted 5.85 ng/mL of dopamine and metabolites per 800,000 cells per $cm^2$. These results are consistent with the idea that naïve state, NME7-AB grown cells differentiate into dopaminergic neurons better than primed state stem cells.

Previous work showed that dopaminergic neuron precursors, implanted into the brain at approximately Day 16 to Day 28 post onset of differentiation, engrafted better and had a more of a therapeutic benefit than implanting cells after full maturation to ~Day 40-60. These results imply that, in the environment of the brain, the progenitor cells were able to mature into functional dopaminergic neurons. These results are also consistent with the idea that the maturation factors supplied by the brain are not required for the early stages of differentiation into neurons or dopaminergic neuron precursors. We therefore aimed to determine which factors produced in the brain could be important for the development of dopaminergic neurons and also determined the timeframe for contacting dopaminergic neuron precursors with those factors. We added candidate factors at about the same time that researchers empirically found that the dopaminergic neuron progenitors had to be implanted into the brain, which was between Day 16 and Day 28 of the differentiation protocol (Samata and Takahashi 2016, DOI: 10.1038/ncomms13097). The effect of candidate factors, added separately or in combinations, on expression of molecular markers, engraftment and dopamine secretion was assessed.

Several factors produced in the brain have been suggested as being important for neural differentiation. Some of the candidate factors supplied by the brain which could induce the final steps of maturation to dopaminergic neurons are vitamins A [Qing mu et al 2018, DOI: 10.1080/21691401.2018.1436552; Engberg et al, Stem Cells 2010; 28:1498-1509; JD Bremner, 2007, doi: 10.1016/j.pnpbp.2007.07.001], B [Carlos Alberto Calderón-Ospina, Mauricio Orlando Nava-Mesa, doi: 10.1111/cns.13207, Guilarte, 2006 Journal of Neurochemistry, DOI:10.1111/j.1471-4159.1987.tb04111.x, Peraza et al, 2018, BMC Neuroscience], C [V. Bagga et al 2008, Cell Transplantation; Xi-Biao He et al, 2015, Stem Cells, doi: 10.1002/stem.1932] and D [Luan et al 2018, Mol Neurobiol, doi: 10.1007/s12035-017-0497-3]. There are various forms of these vitamins and several are reported to be at elevated levels in the brain during neural development. However, study results are often conflicting. Several scientific studies conclude that vitamin A, or its derivative retinoic acid, block neural differentiation while other studies imply that they could be required for neural differentiation. Similarly, various types of vitamin B have been reported as being beneficial for neural differentiation, while others report that they suppress neural differentiation.

We assessed the effects of various forms of B vitamins, especially the neurotropic B vitamins, B1, B6 and B12, forms of vitamin A, and vitamin C on the development of hiPS cell-derived dopaminergic neurons. In addition to vitamin A, which is fairly insoluble, we assessed the effect of various high lipid density additives for solubilizing vitamin A, such as serum albumin and serum albumin replacements including commercially available Albumax.

We performed a series of experiments that compare the state of the art to the methods and compositions of the invention. On the one hand, we compared standard primed state stem cells to NME7-AB grown naïve stem cells differentiating to dopaminergic neurons. On the other hand, we compared Protocol A to our improved protocols, Protocol B, C, C.2 and D (FIG. 1A-FIG. 1E), in which various vitamins and other components are added starting at about Day 20+/−3 of the protocol. The resultant cells were analyzed at various timepoints for the presence of appropriate molecular markers, characteristic morphology, length of neurite outgrowth as an indicator of engraftment potential and most importantly, the amount of dopamine produced and secreted.

In Protocol C.2, around Day 20, the neural base media was exchanged for one that did not contain pyridoxal but instead contained pyridoxine and two forms of vitamin A. The following experiments compare stem cells differentiated to become dopaminergic neurons according to Protocol A or Protocol C.2. On Day 24, immunofluorescent staining was performed to detect the presence of molecular markers of dopaminergic neuron progenitors generated using Protocol A (FIG. 2A-FIG. 2L) or Protocol C.2 (FIG. 3A-FIG. 3L). GIRK2 (G-protein-regulated inward-rectifier potassium channel 2) is expressed in dopaminergic neurons while Tuj1 (neuron-specific class Ill B-tubulin) is a pan-neural marker. TH (tyrosine hydroxylase) is considered a gold standard in the identification of dopaminergic neurons because it is an enzyme that catalyzes the conversion of L-tyrosine to L-3,4-dihydroxyphenylalanine, which is the rate limiting step in dopamine synthesis. DAT (dopamine active transporter) is equally important as it is the transmembrane protein that pumps dopamine from the synapse back into the cytosol. Both differentiation protocols produced cells that were positive for all appropriate molecular markers. However, the cells produced using Protocol C.2 formed interconnected networks of neurons with longer projections and more connectivity than the cells produced from Protocol A.

The difference in morphology is also apparent in the immunofluorescent studies performed on Day 60. iPSCs that had previously been grown in $NME7_{AB}$, then differentiated according to Protocol A lack axonal projections and the inter-connected network characteristic of functional neurons, whereas the same cells differentiated according to Protocol C.2 have the desired morphology (FIGS. 4A-4B and FIGS. 4E-4F). Note that in this experiment, a second naïve clone, $iPSC_{NME7-N7B}$, was used. This second naïve state clone was generated by episomal reprogramming using the core pluripotency factors, OCT4/SOX2/KLF4/c-Myc in NME7-AB media. The other clone used in these experiments, $iPSC_{NME7-6E}$, was generated using Sendai virus (Carter et al 2016) and had previously been demonstrated to be able to differentiate into functional cardiomyocytes and hepatocytes. Using Protocol A for differentiation of primed state stem cells, such as $iPS_{E8-A6}$, cells repeatedly failed before reaching Day 60. However, we found that if iPSCs that had been grown in E8 were cultured in E8 plus beta-catenin, agonist such as WNT3A, for 48 hours before initiating differentiation, they exhibited increased survival at Day 60 and may have improved morphology. However, the morphology and expression pattern of DAT, TH, and GIRK2 are still inferior to iPSCs grown in NME7AB plus WNT3A for 48 hours then differentiated according to Protocol C.2 (FIGS. 4C-4D and FIGS. 4G-4H). The naïve stem cells, differentiated according to Protocol C.2 formed networks with the desired morphology. The complexity of the morphology of neurons, such as branch density and grouping patterns, are highly correlated to the function of the neuron.

One impediment to therapeutic use of stem cell derived dopaminergic neurons is the current low engraftment rate. It has been estimated that for therapeutic benefit, at least 100,000 functional dopaminergic neurons need to engraft into the patient brain. A first order in vitro method to assess engraftment might be a wound healing assay, also known as a scratch test. iPSCs previously grown in either $NME7_{AB}$ or E8 were differentiated using Protocol C.2 until cells were confluent then a scratch, or scar, was made. The dopaminergic neurons derived from iPSCs that had been previously grown in $NME7_{AB}$ media generated neural, axonal projections that bridged the gap within 6 days, wherein the cells that had been grown in E8 media had fewer and shorter projections (FIG. 5A-FIG. 5F). The green fluorescence is a measure of dopamine uptake, from a labeled dopamine mimic.

Figures 6A, 6B, 6C, 6D:
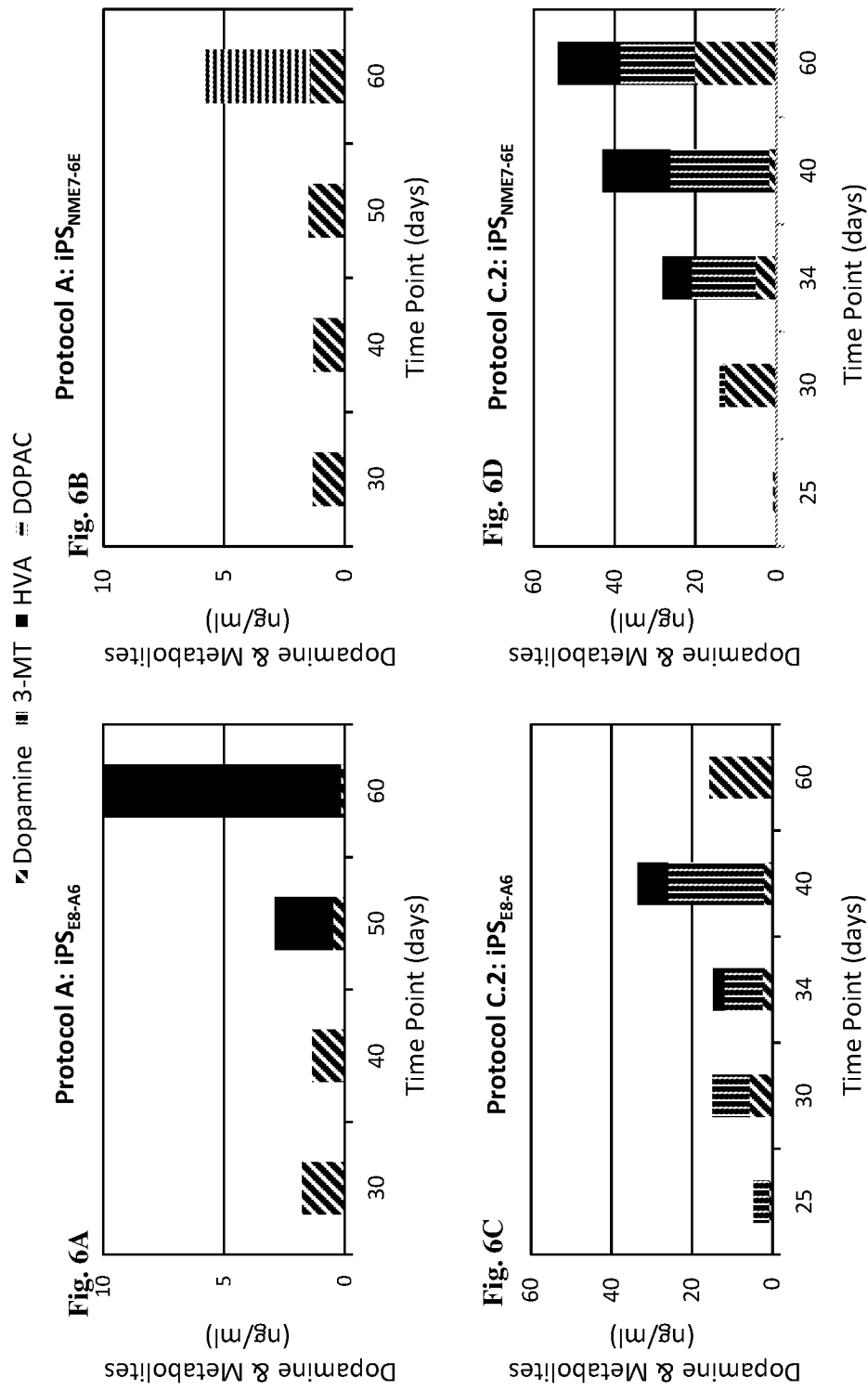
FIG. 6A-6D show graphs of secretion of dopamine and its metabolites, from 800,000 cells/cm$^2$ that were plated on Day 11 of the protocol, over a time period from Day 30 to Day 60, post initiation of differentiation.
Figure 7:
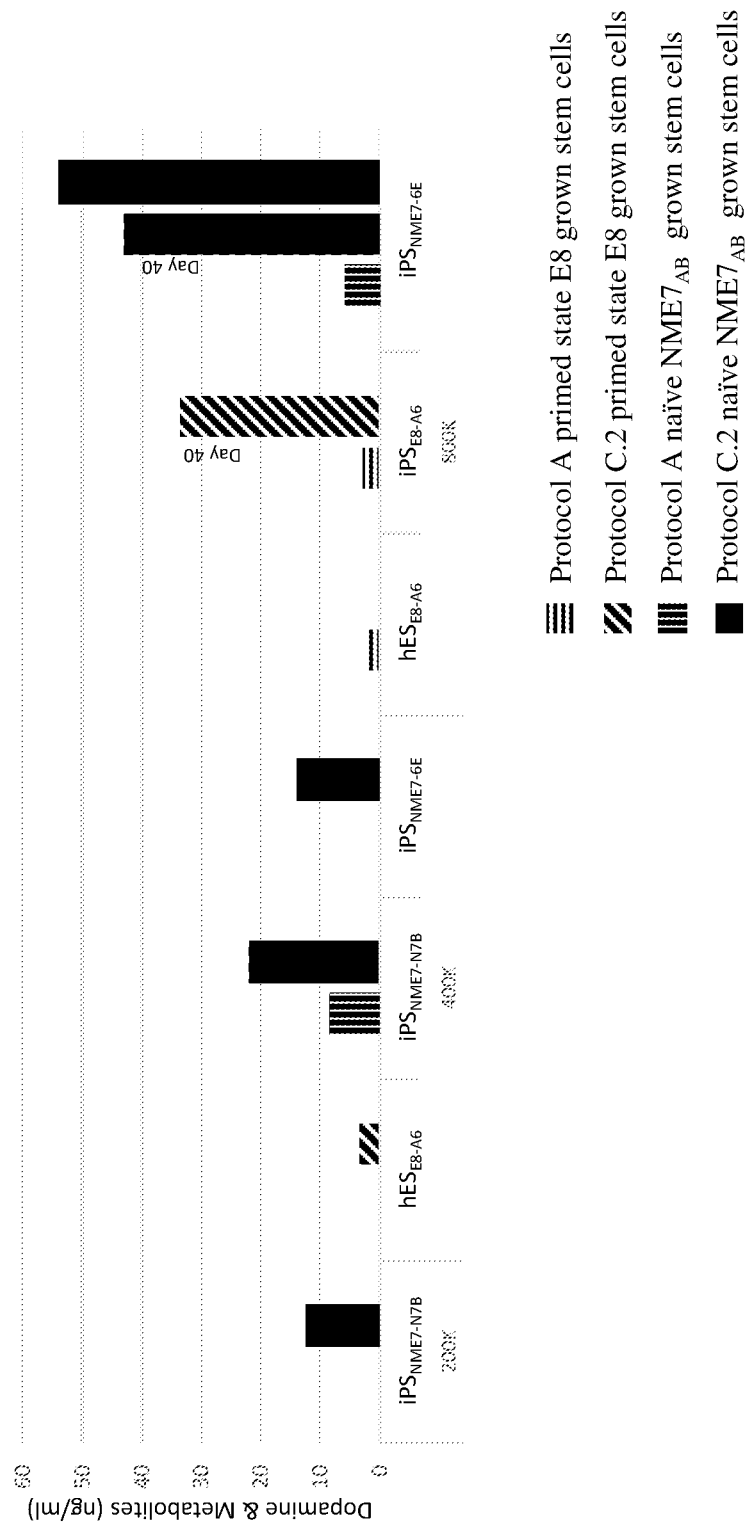
FIG. 7 shows a graph of the amount of dopamine and its metabolites secreted by a variable number of cells and measured at Day 60, or Day 40, where indicated, where the horizontal stripe bars indicate primed state stem cells differentiated according to Protocol A, the cross hatch bars indicate primed state stem cells differentiated according to Protocol C.2, the vertical stripe bars indicate naïve stem cells differentiated according to Protocol A, and the solid black bars indicate naïve stem cells differentiated according to Protocol C.2. Note that the number of cells refers to the number of cells plated on Day 11 of the protocol per cm$^2$.
Figure 9:
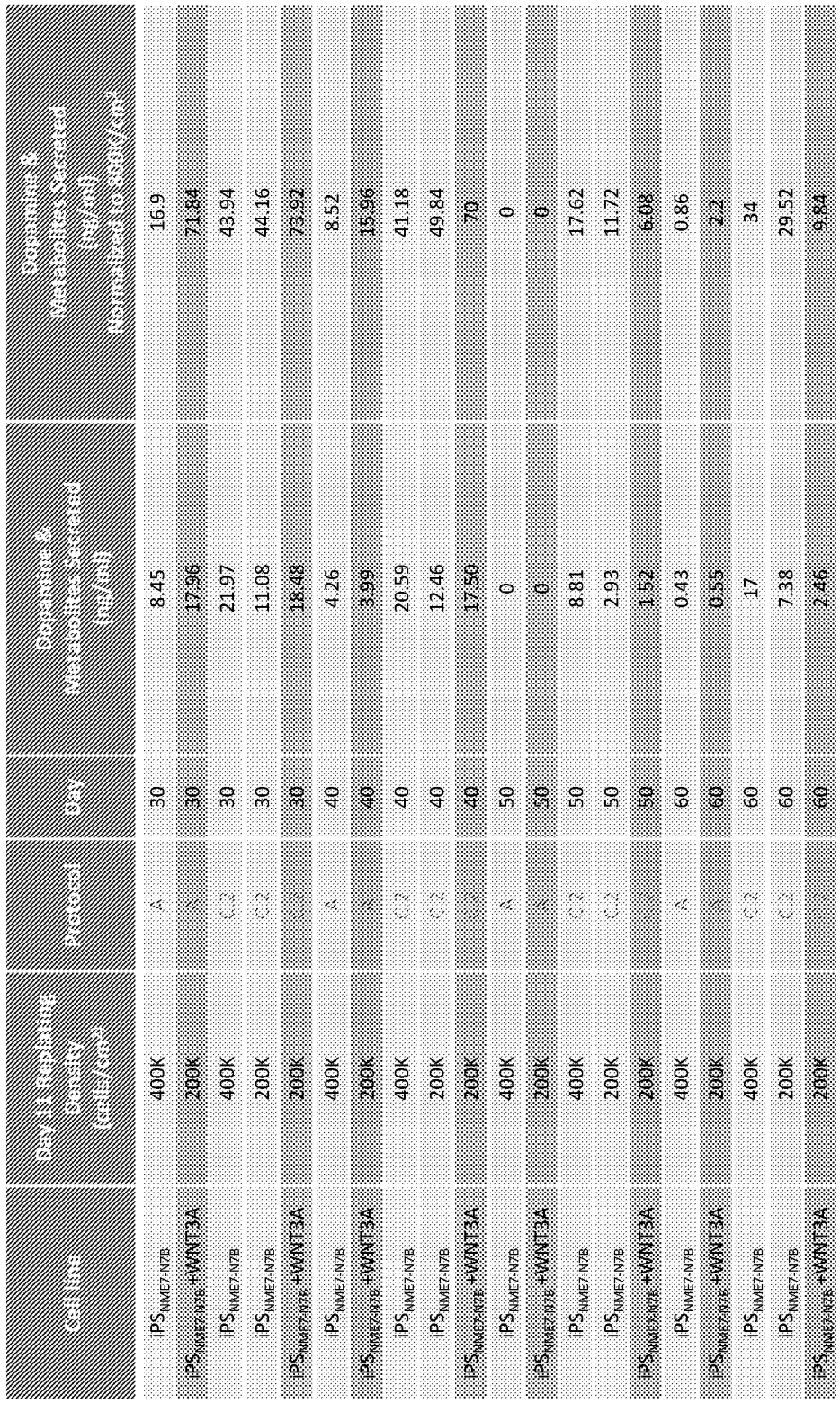
FIG. 9 is a table that shows the amount of dopamine and its metabolites that is secreted by episomal naïve clone iPS$_{NME7-N7B}$. Day 11 number of cells plated is varied, as well as the Day number when dopamine secretion is measured. Additionally, in some cases, where indicated, WNT3A was added to culture media at 100 ng/mL for 48 hours before initiation of differentiation.
Figures 11A, 11B, 11C, 11D, 11E, 11F:
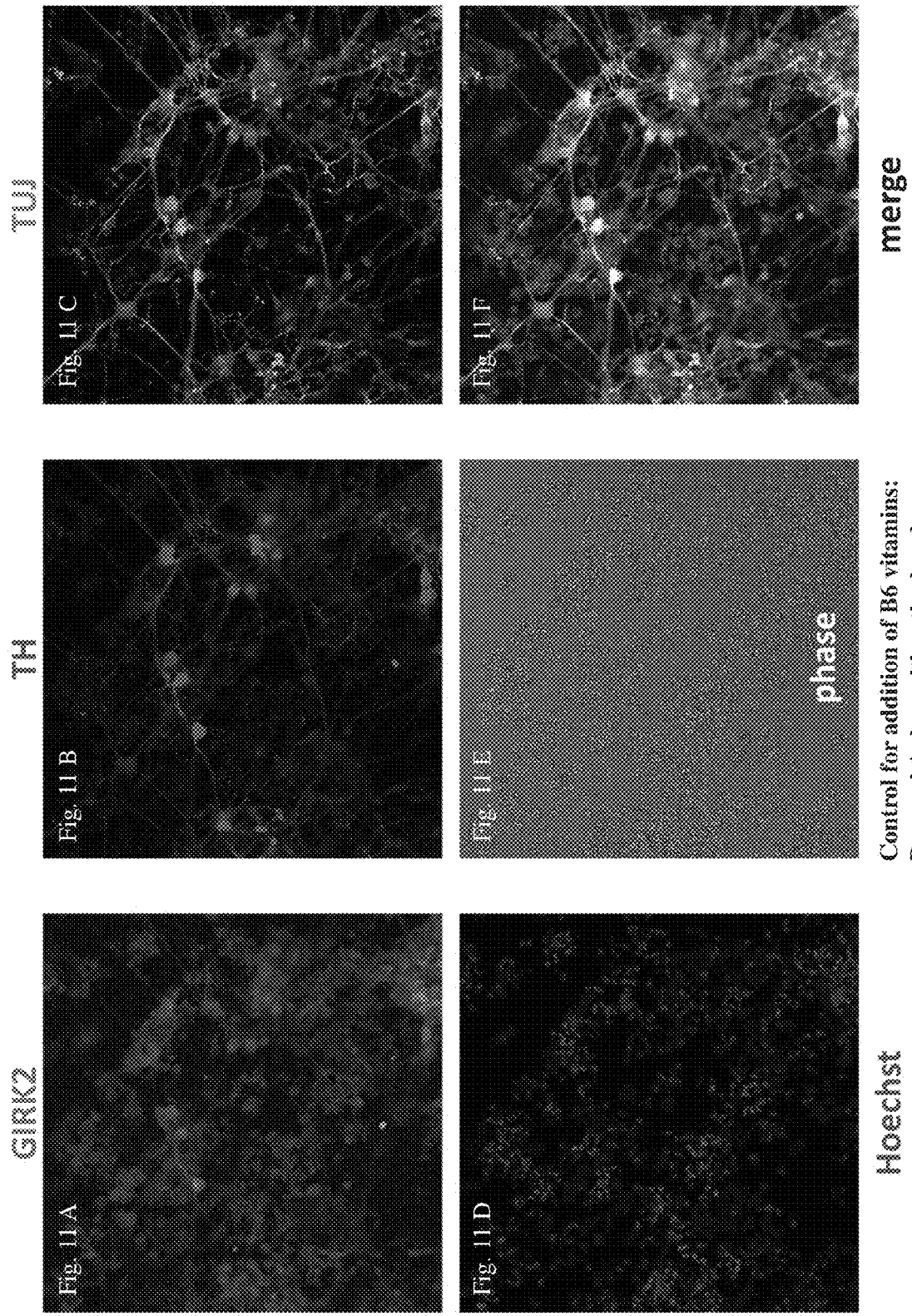
Figures 12A, 12B, 12C, 12D, 12E, 12F:
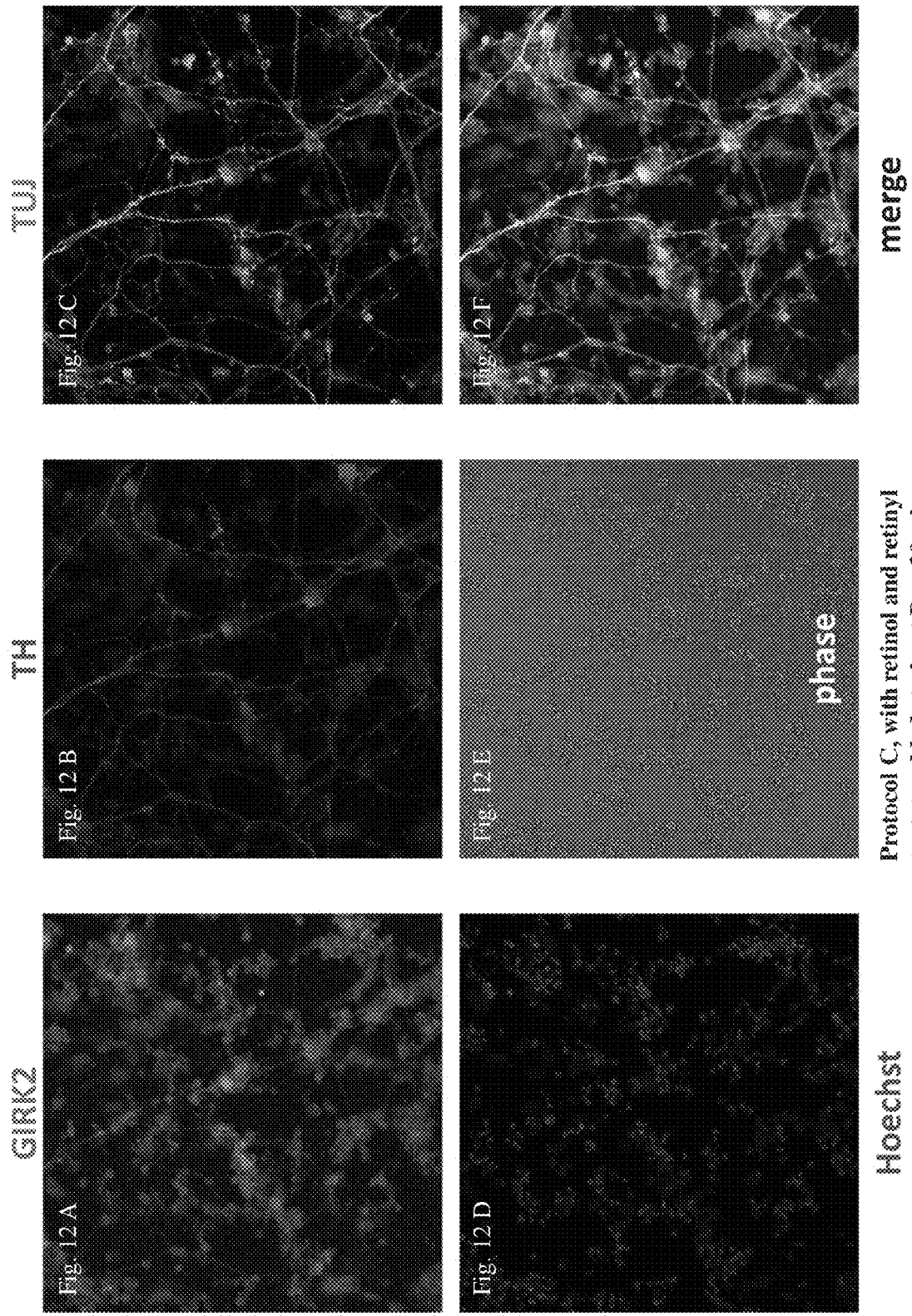
Figures 13A, 13B, 13C, 13D, 13E, 13F:
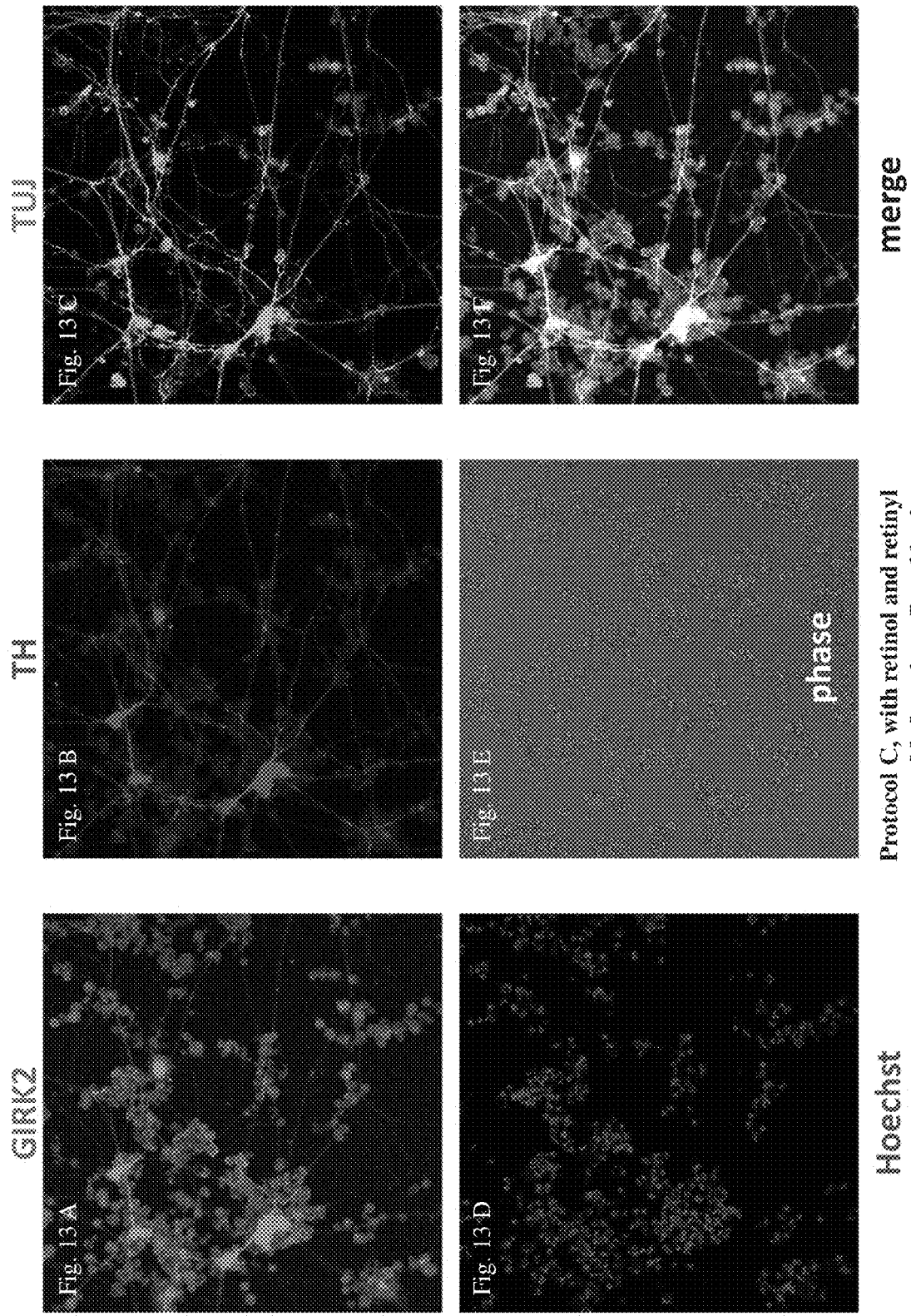
Figures 14A, 14B, 14C, 14D, 14E, 14F:
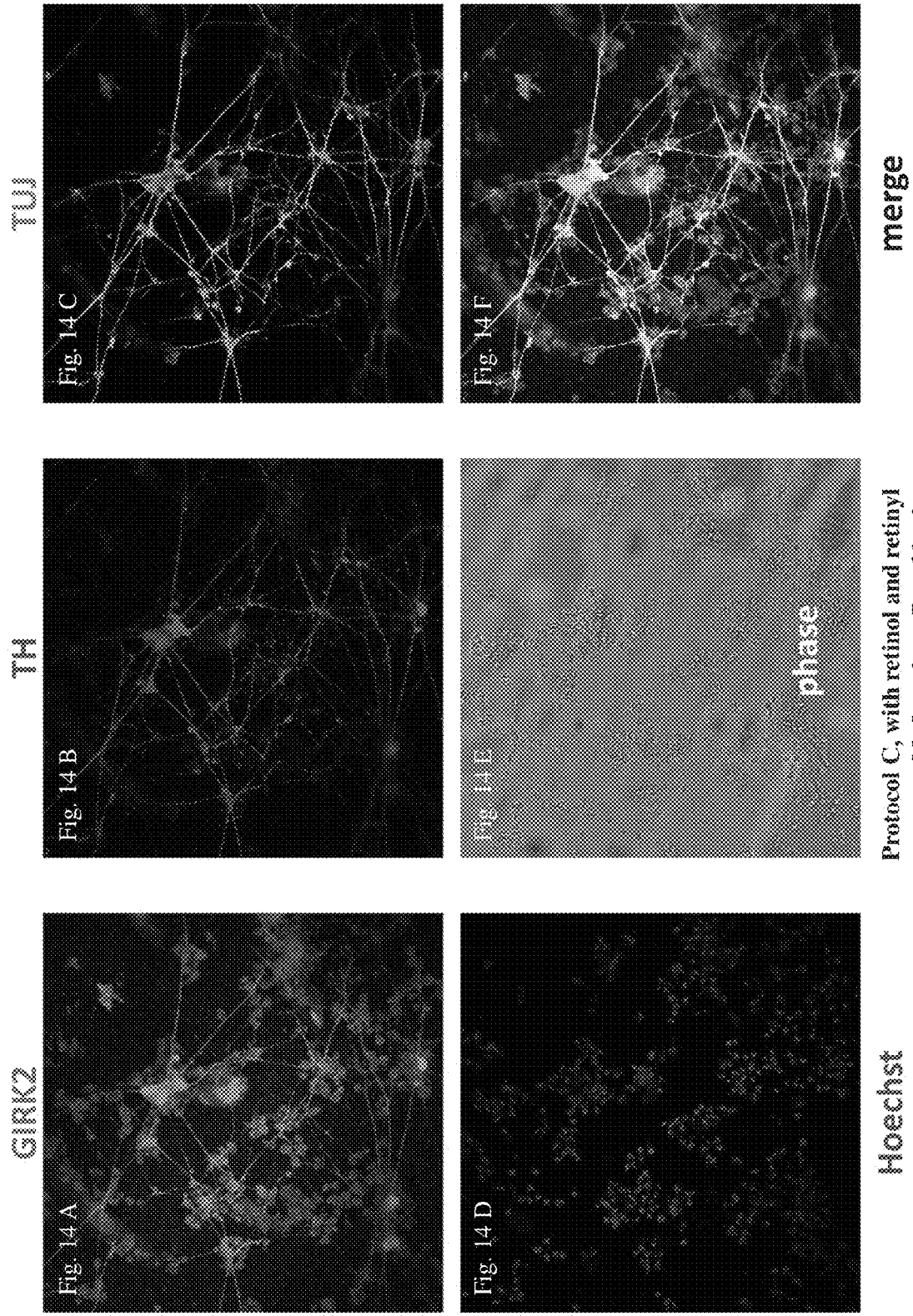
FIG. 14A-14K shows fluorescent photographs taken at 20× magnification on a confocal microscope of human iPS cells at Day 24 of differentiation to dopaminergic neurons according to the protocol described here as Protocol A, except that around Day 20, vitamin A in the form of retinol and retinyl acetate have been introduced into the media until cell harvest. In this experiment, vitamin B6 in the form of pyridoxal-5'-phosphate, also known as PLP, was added to a final concentration of 20 uM.
Figure 14G:
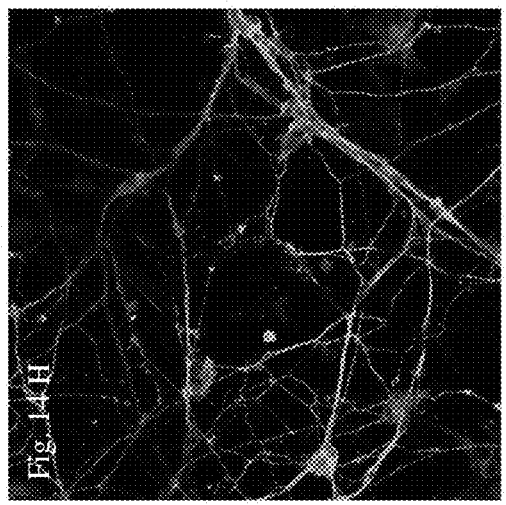
Figure 14H:
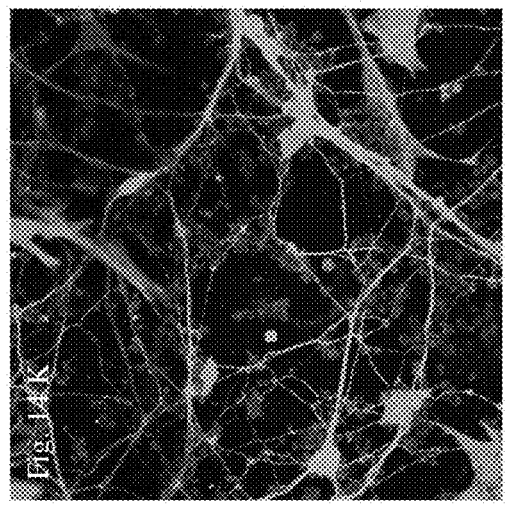
Figure 14I:
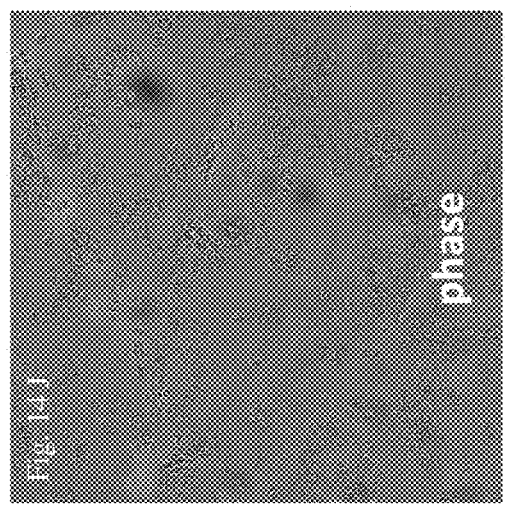
Figure 14J:
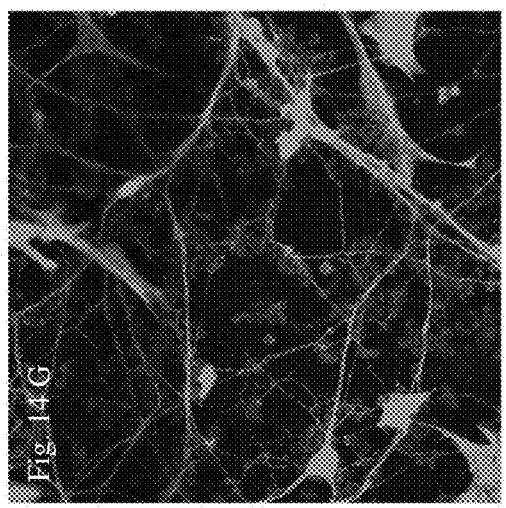
Figure 14K:
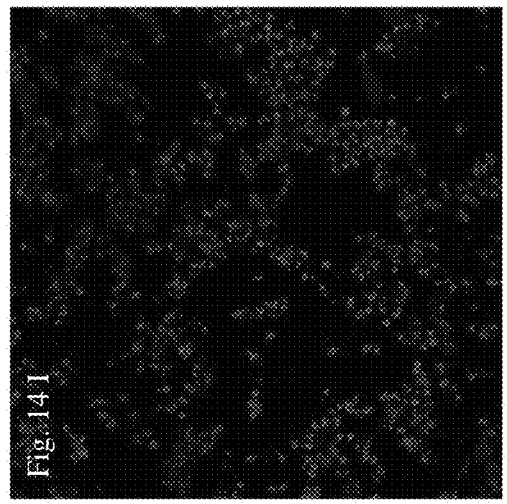
Figures 15A, 15B, 15C, 15D, 15E, 15F:
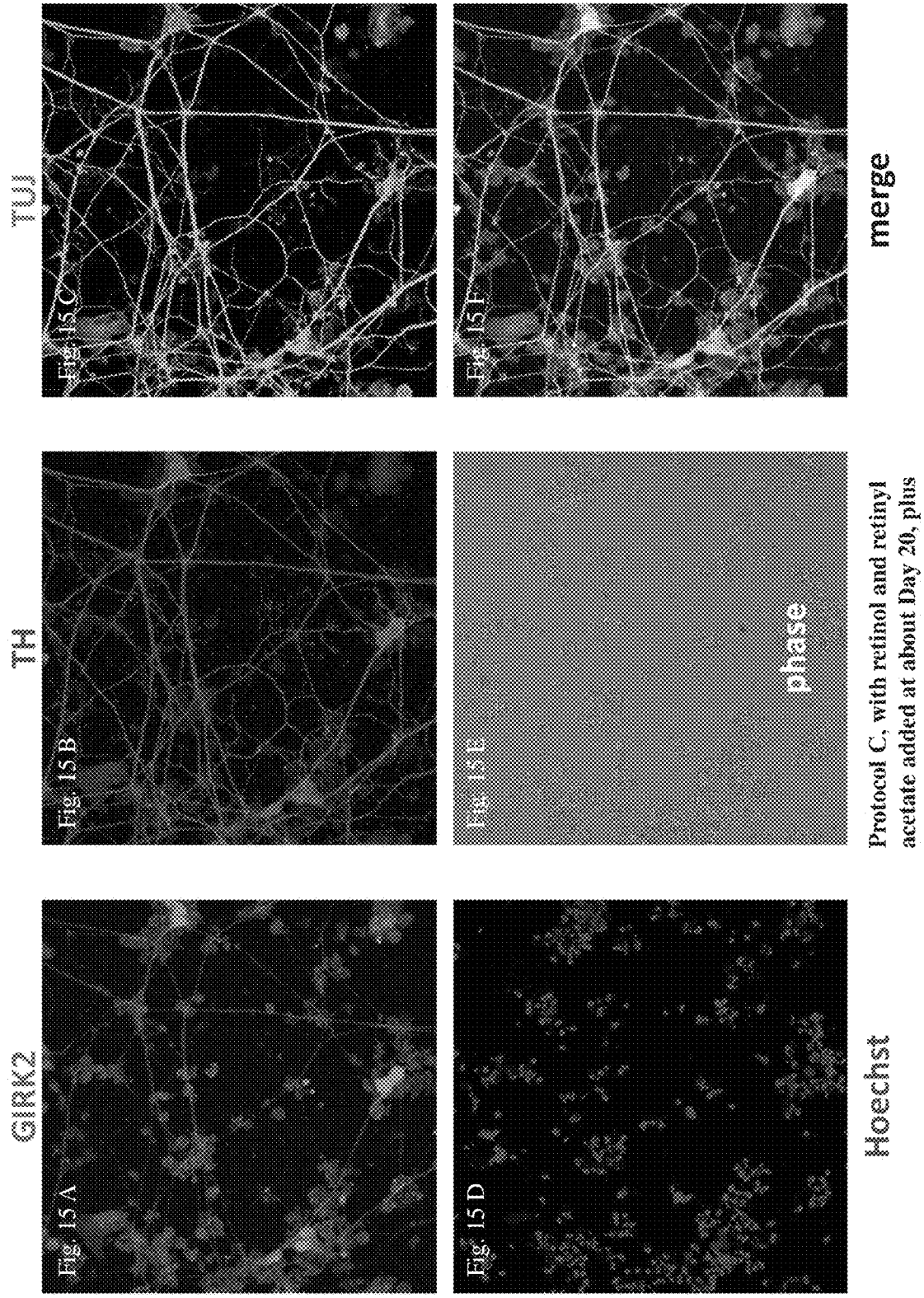
Figures 16A, 16B, 16C, 16D, 16E:
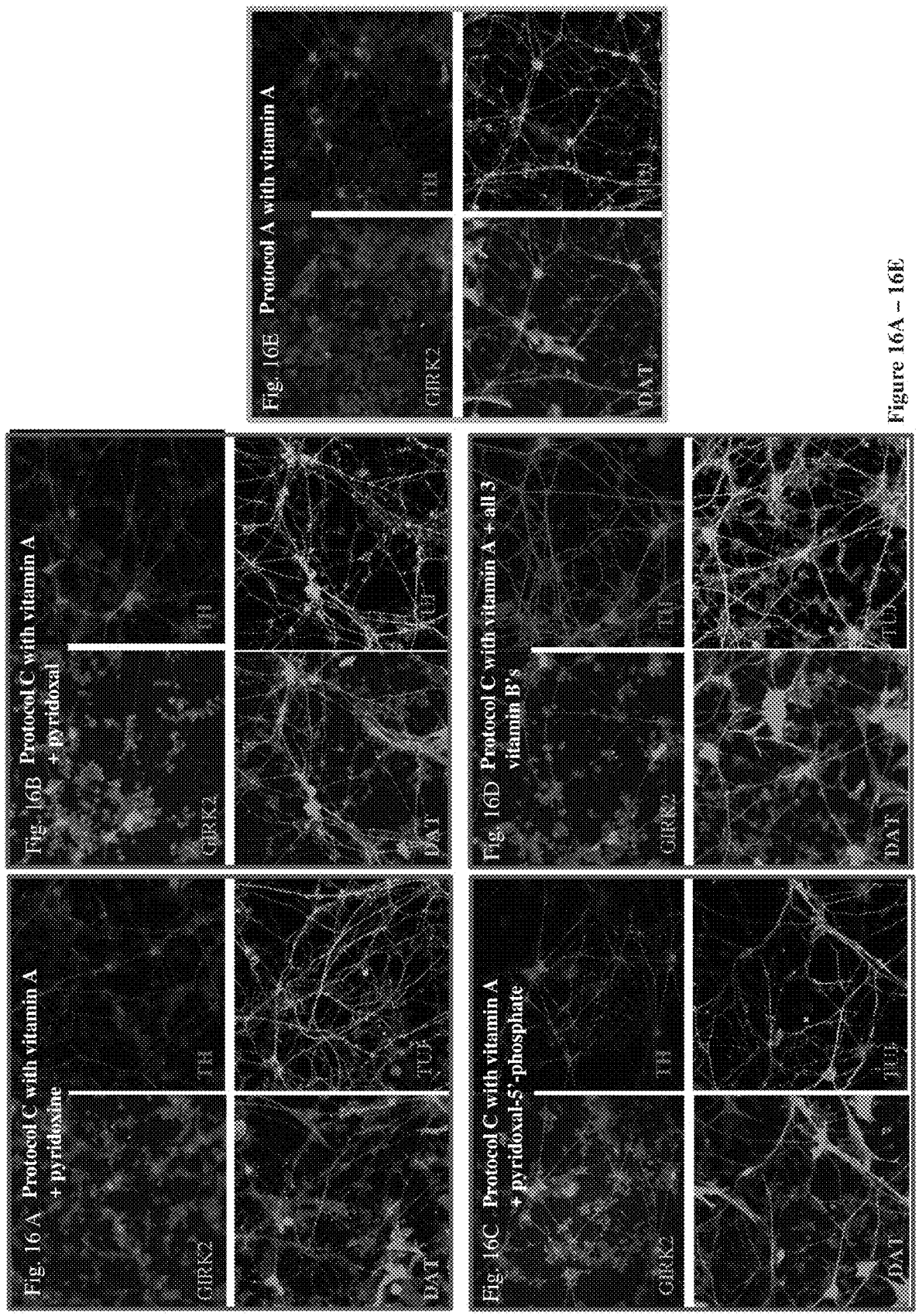
FIG. 16A-16E shows fluorescent photographs taken at 20× magnification on a confocal microscope of human iPS cells at Day 24 of differentiation to dopaminergic neurons according to the protocol described here as Protocol A, except that retinol and retinyl acetate have been added to the differentiation media around Day 20, so that the effect of adding various forms of vitamin B6 can be seen.

One of the most important measures of dopaminergic neuron function is their ability to make and secrete dopamine. HPLC analysis to quantify secreted dopamine and its metabolites was performed over a range of cell densities and at various stages of the differentiation protocols. Primed state human iPS cells differentiated into dopaminergic neurons according to Protocol A, secrete as much as 10 ng/mL dopamine and its metabolites by Day 60 (FIG. 6A), whereas naïve state stem cells differentiated using Protocol A secreted about 7 ng/mL at that timepoint (FIG. 6B). In sharp contrast, primed state stem cells differentiated using Protocol C.2 secreted almost 40 ng/mL at Day 60 (FIG. 6C) and naïve state stem cells secreted almost 60 ng/mL of dopamine and its metabolites (FIG. 6D). In the experiment shown in FIG. 6, the amount of dopamine and its metabolites that was measured was secreted by 400,000 cells per cm$^2$ and measured at Day 60 post initiation of differentiation. FIG. 7 shows a graph of the amount of dopamine and its metabolites secreted by a variable number of cells and measured at Day 60, or Day 40, where indicated, where the horizontal and vertical striped bars indicate cells differentiated using Protocol A and the cross hatched and solid bars indicate cells differentiated using Protocol C.2. The horizontal striped and cross hatched bars indicate that primed state stem cells were used and the vertical striped and solid bars indicate where naïve stem cells were used. The more than 40 experiments performed using Protocol A compared to Protocol C.2 (FIG. 8, FIG. 9 and FIG. 10) show that cells differentiated to dopaminergic neurons using Protocol C.2 produced cells that secreted 10-times more dopamine on average than those produced using Protocol A. Further, cells differentiated from NME7AB naïve cells reproducibly produced the most dopamine.

We next sought to further investigate the effect of various forms of vitamin B6 on stem cell differentiation to dopaminergic neurons. Recall that in the previous set of experiments, either primed state stem cells or naïve state stem cells were differentiated to become dopaminergic neurons according to either Protocol A or Protocol C.2, where at about Day 20, the neural base media was exchanged such that it no longer contained pyridoxal but instead contained pyridoxine plus retinol and retinyl acetate.

In this next set of experiments, we followed Protocol A, except that around Day 20, the neural base media will be exchanged for one that contains approximately 1.2 uM retinol and 0.17 uM retinyl acetate and various other forms of vitamin B6 were then added (FIG. 1, Example 2). Resultant cells were analyzed for cell morphology, yield of TH and DAT positive cells relative to Tuj1 positivity and the number and length of neural projections as an indicator of engraftment potential.

A subset of B vitamins, B1 (thiamine), B6 (pyridoxine) and B12 (cobalamin) are termed neurotropic B vitamins. Levels of B6 are increased in gestational brain development. Pyrodoxine is the dietary form of B6. The PLP form of vitamin B6 (pyridoxal phosphate) is the biologically active form of vitamin B6, which is required for the synthesis of neurotransmitters such as for the synthesis of dopamine from L-Dopa. In media, pyridoxine may get metabolized to form pyridoxal-5'-phosphate. B12 has been reported to play a role in the synthesis of myelin.

We discovered that the addition of certain forms of vitamin B6 to basic neural differentiation media greatly improve the quality of dopaminergic neurons derived from stem cells, greatly increase the amount of dopamine they secrete and significantly increased engraftment in in vitro wound healing experiments. The timing, concentration and the various forms of vitamin B are key factors in the differentiation and maturation of dopaminergic neurons from human stem cells in vitro.

We assessed the effects of various forms of vitamin B6 on differentiation of dopaminergic neurons from human iPS cells. Because the initial experiments showed that naïve NME7-AB human iPS cells differentiate into dopaminergic neurons better than the hiPSCs that had been grown in FGF2 containing E8 media, these experiments were only carried out on naïve state stem cells and repeated later using primed state stem cells. The differentiation protocol called Protocol A (FIG. 1) was followed until Day 20. From Day 21 onward, to the basal media was added vitamin A in the form of retinol at 1.2 uM and retinyl acetate at 0.17 uM and vitamin C as ascorbic acid-2-phosphate at a final concentration of about 200 nM. The negative control, in which no additional vitamin B is added is shown in FIG. 11A-11K. It is important to note that the neural basal media that was used in all conditions contained 10 uM pyridoxal, so pyridoxal at this low concentration was present from the onset of differentiation.

Figure 17:
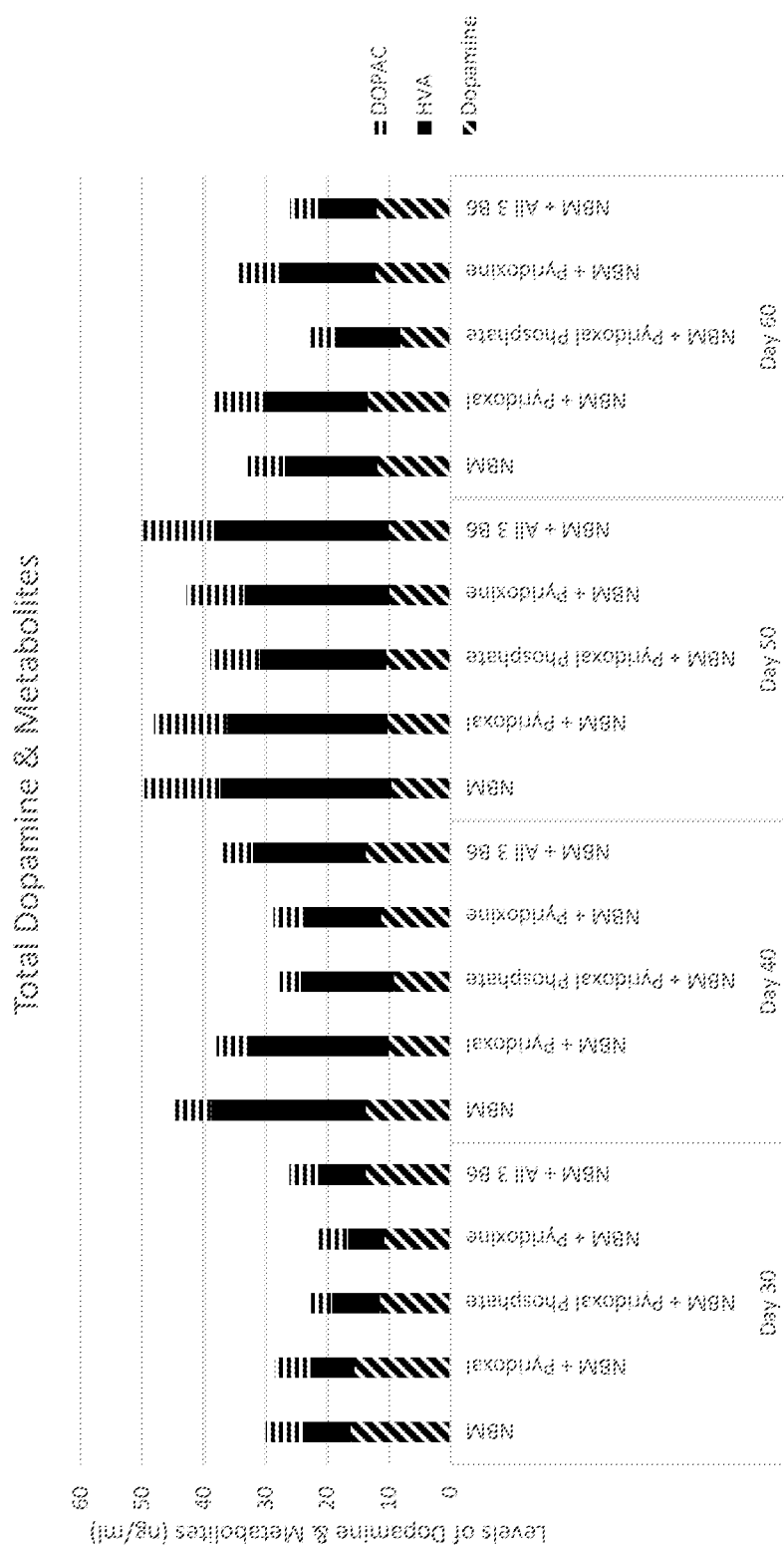
FIG. 17 is a graph of the amount of dopamine and its metabolites, measured by HPLC, present in the conditioned media from 200,000 cells taken at Day 30, Day 40, Day 50 or Day 60. Media was not withdrawn from a single source of cells. Rather separate experiments were allowed to proceed until the day media was withdrawn for analysis. This experiment used Protocol C, where on about Day 20 and forward, retinol and retinyl acetate were added to every condition. The forms of vitamin B that were added to a base neural media were varied. In this experiment, the base media contained about 10 uM pyridoxal. In the condition that has pyridoxine added, the pyridoxal is omitted from the base media.
Figure 18A:
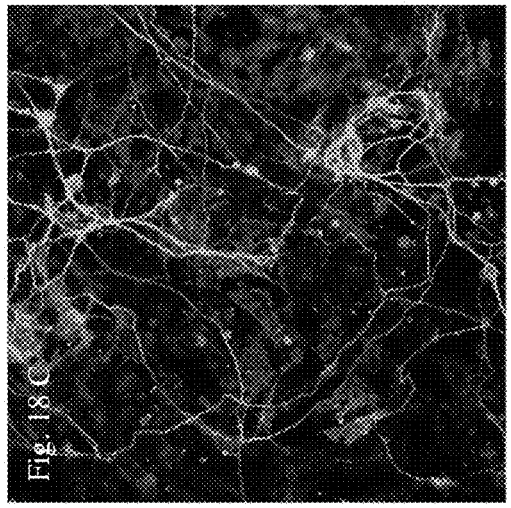
FIG. 18A-18I shows fluorescent photographs taken at 20× magnification on a confocal microscope of human iPS cells at Day 24 of differentiation to dopaminergic neurons. These photographs are of the control experiment, where cells were differentiated according to Protocol A.
Figure 18B:
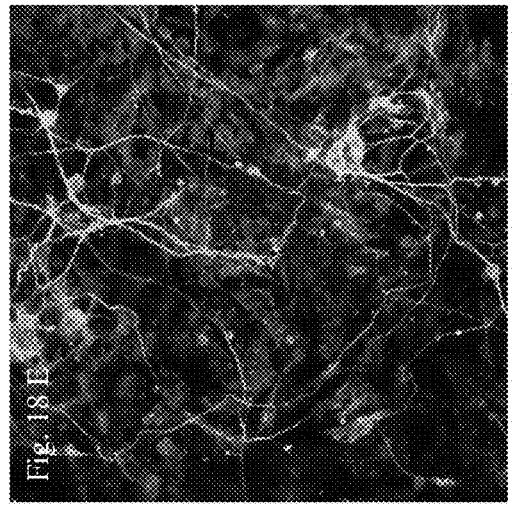
Figure 18C:
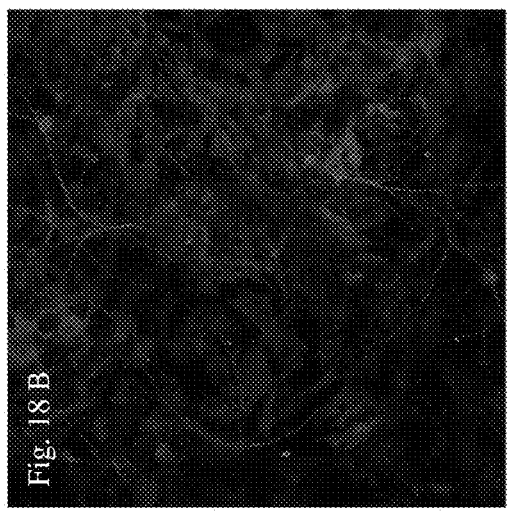
Figure 18D:
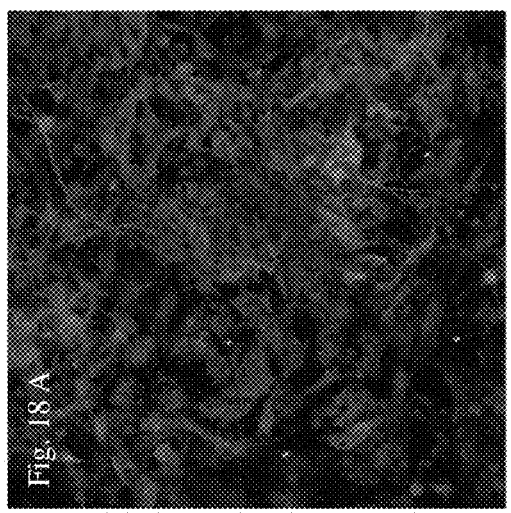
Figure 18E:
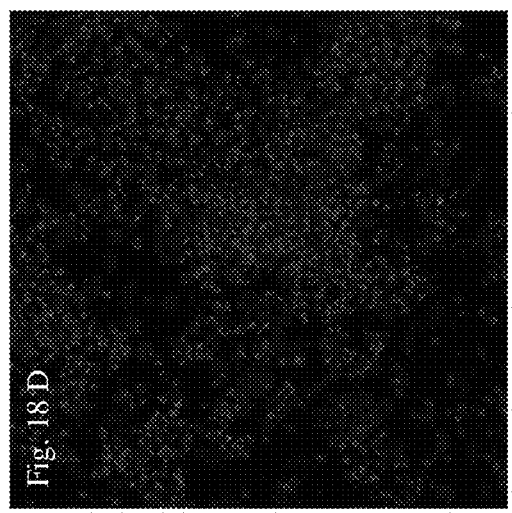
Figure 18F:
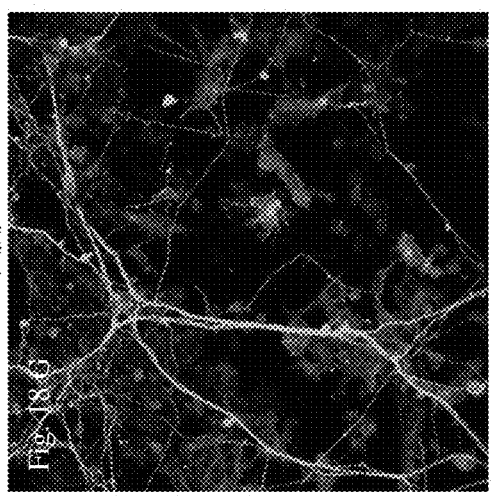
Figure 18G:
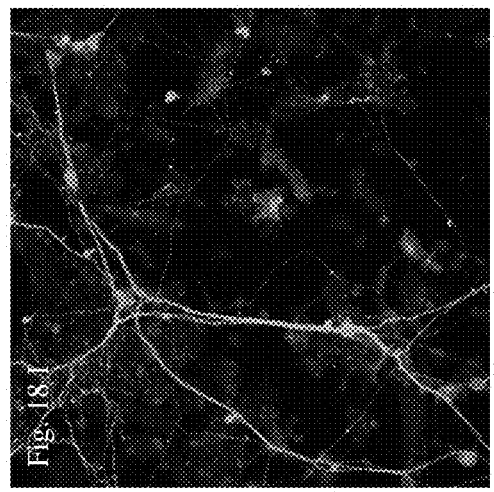
Figure 18H:
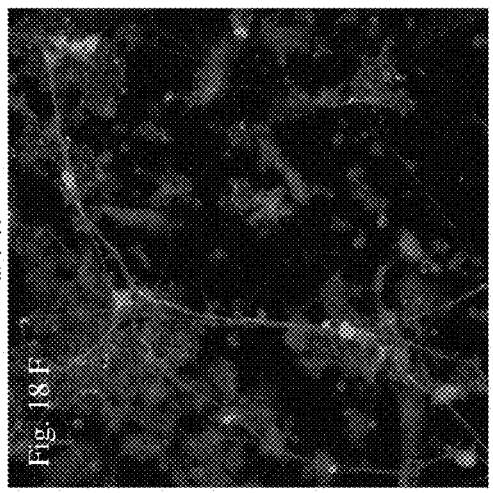
Figure 18I:
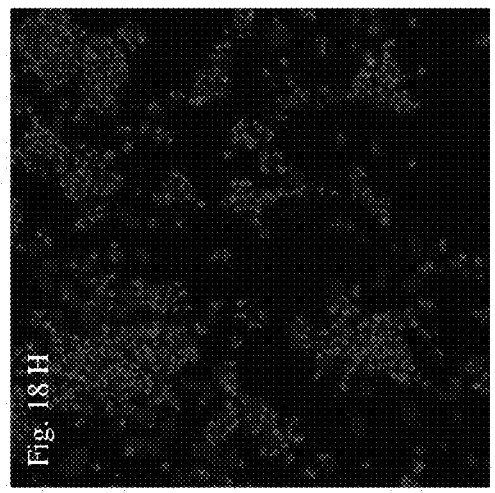
Figures 19A, 19B, 19C, 19D, 19E:
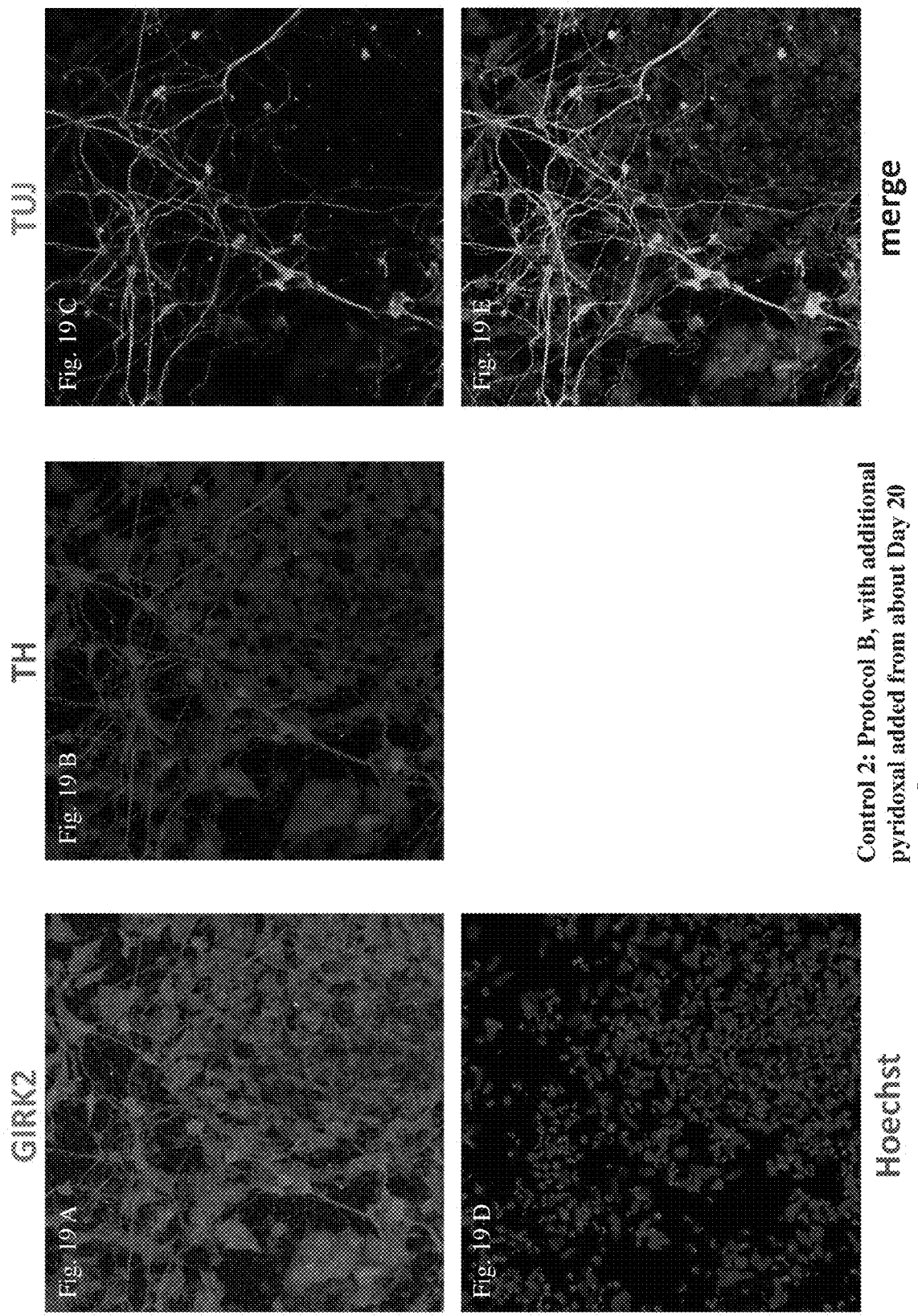
FIG. 19A-19I shows fluorescent photographs taken at 20× magnification on a confocal microscope of human iPS cells at Day 24 of differentiation to dopaminergic neurons. These photographs are of another control experiment, where cells were differentiated according to Protocol A, except that at Day 20, pyridoxal was added to the media at a final concentration of 11 uM; this modified protocol is called Protocol B here. In this way, one can see the added effect of adding various forms of vitamin A.
Figure 19F:
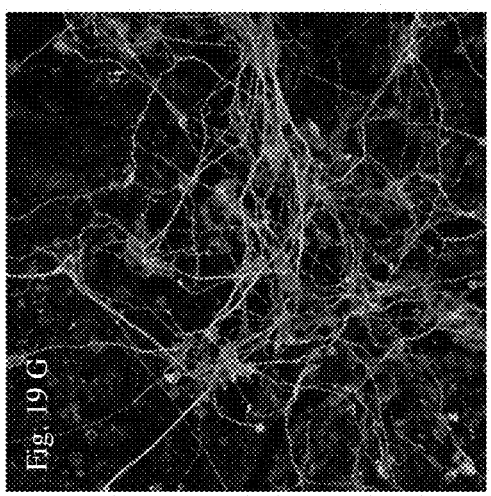
Figure 19G:
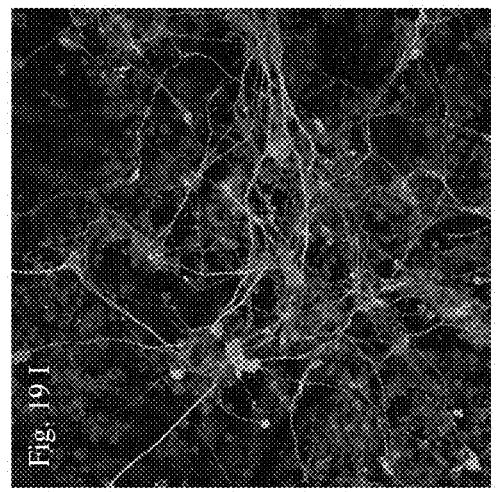
Figure 19H:
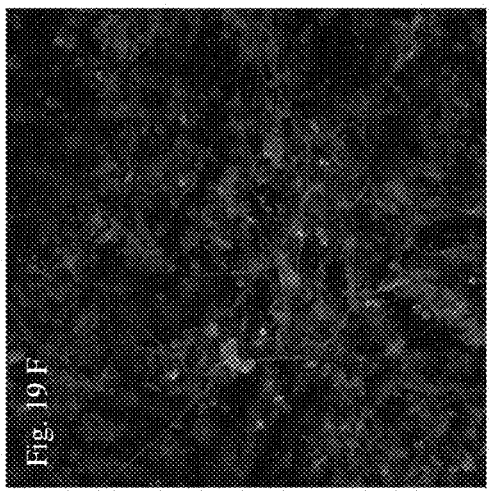
Figure 19I:
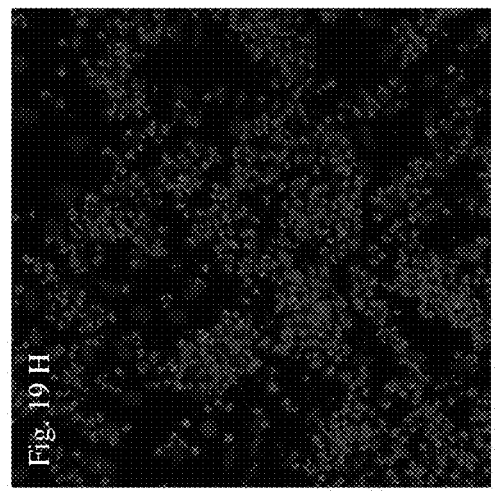
Figure 20A:
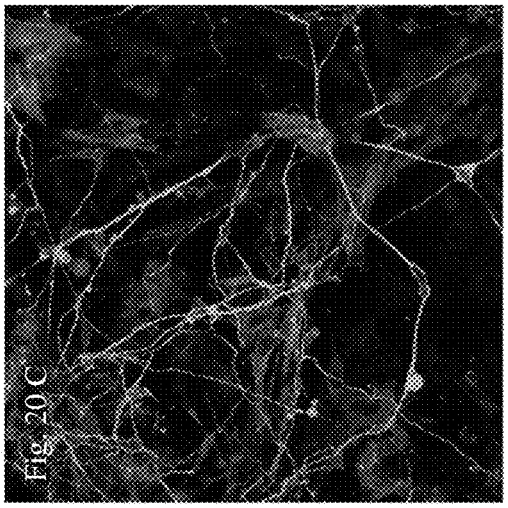
FIG. 20A-20I shows fluorescent photographs taken at 20× magnification on a confocal microscope of human iPS cells at Day 24 of differentiation to dopaminergic neurons, according to Protocol B. In this experiment, in addition to pyridoxal being added to the media from Day 20 onward, two forms of vitamin A were added. Retinol was added to a final concentration of 0.7 uM and retinyl acetate was added to a final concentration of 0.6 uM.
Figure 20B:
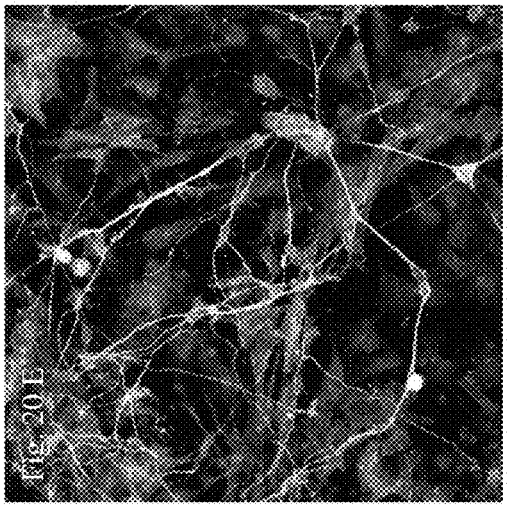
Figure 20C:
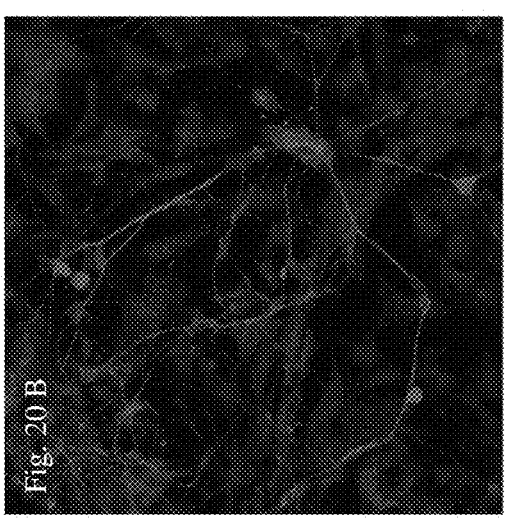
Figure 20D:
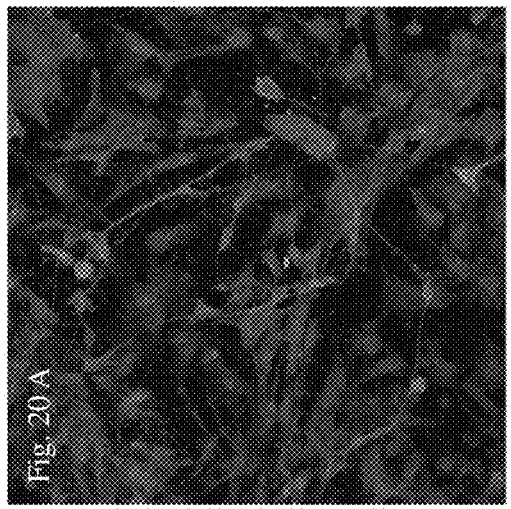
Figure 20E:
Figure 20F:
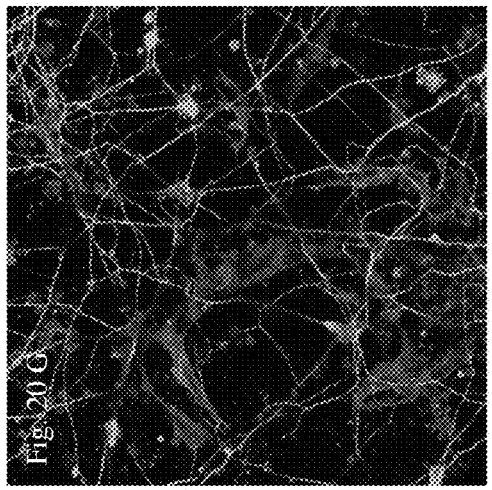
Figure 20G:
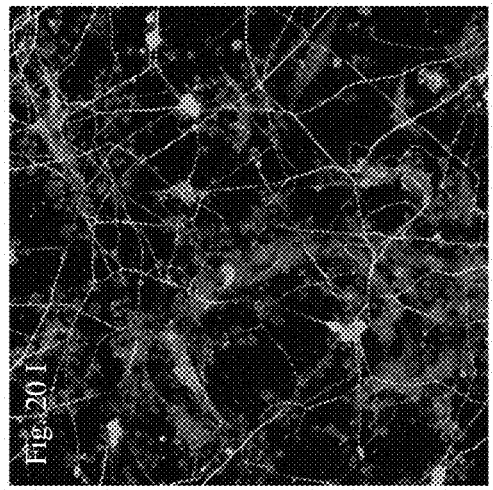
Figure 20H:
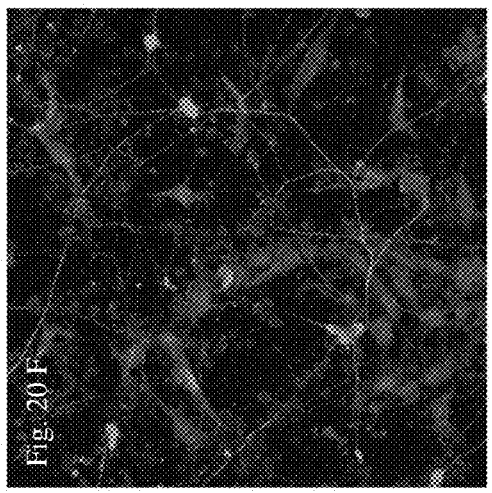
Figure 20I:
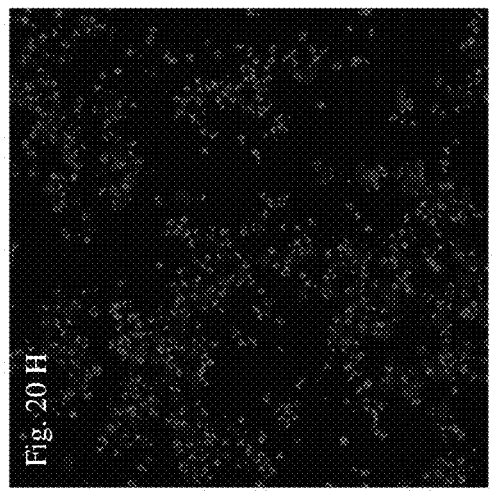
Figure 21F:
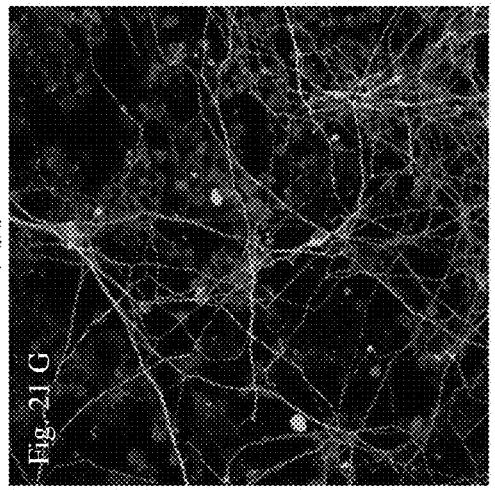
Figure 21G:
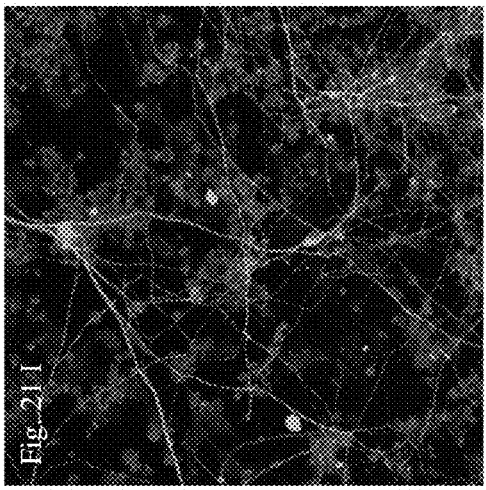
Figure 21H:
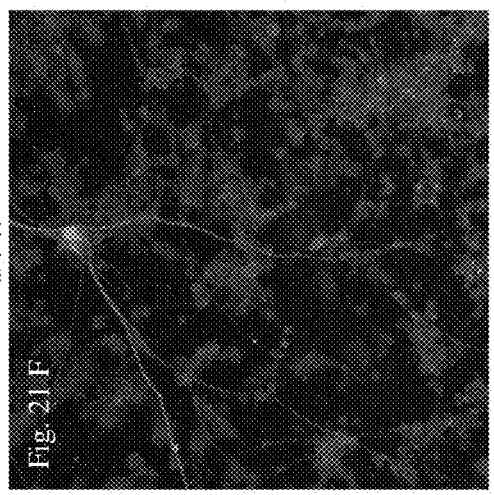
Figure 21I:
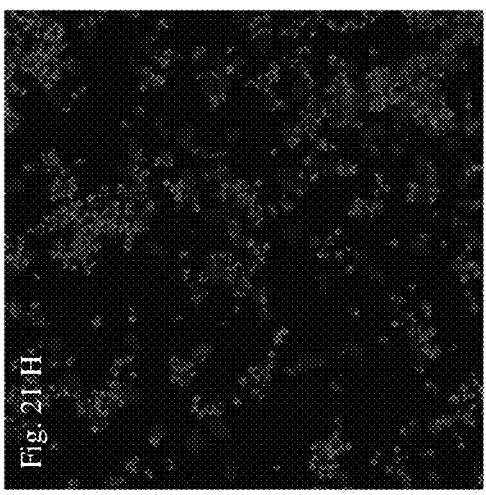
Figure 22F:
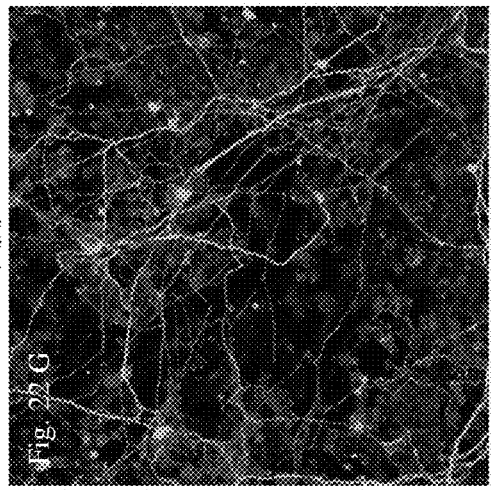
Figure 22G:
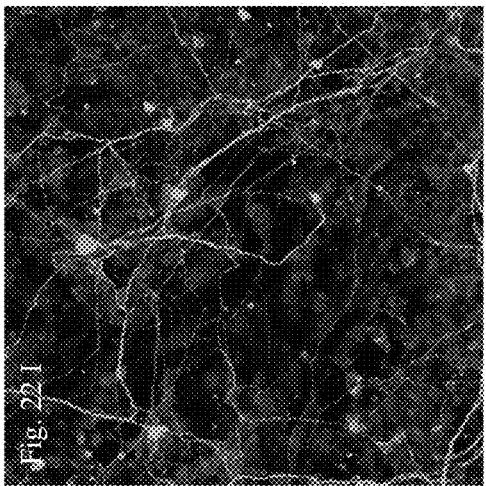
Figure 22H:
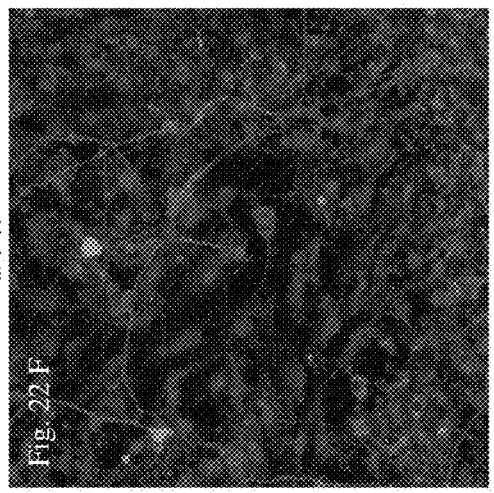
Figure 22I:
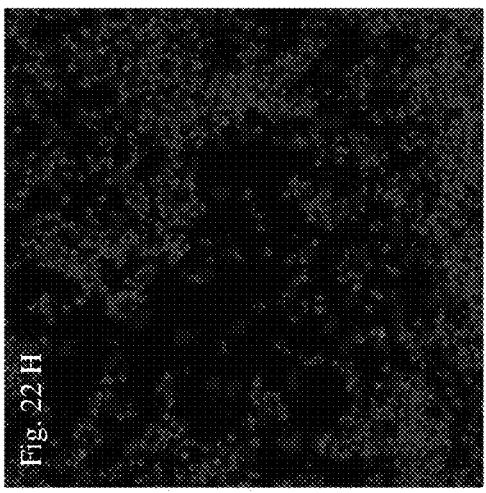

In addition to the vitamins A and C which were constant throughout all conditions, various forms of vitamin B6 were added: 16 uM pyridoxine (FIG. 12A-12K), or 11 uM pyridoxal (FIG. 13A-13K), or 20 uM pyridoxal-5'-phosphate also known as PLP (FIG. 14A-14K), or all of the vitamin Bs. All of the additional B vitamins added to the control media are shown in FIG. 15A-15K. The comparison of the control media to the addition of the various vitamin B6 forms is shown in FIG. 16A-16E. To assess the quality of the resultant dopaminergic neurons we examined: a) the percentage of the GIRK2 positive cells that were also positive for TH, Tyrosine hydroxylase which is an enzyme that mediates the conversion of L-tyrosine to L-3,4-dihydroxyphenylalanine, which is the rate limiting step in dopamine synthesis; this percentage should be high as an indicator of yield of the desired cell type -dopaminergic neurons; b) The percentage of TUJ positive neurons that were also TH positive; TUJ is a pleiotropic marker of neurons; only those that are TH positive are truly dopaminergic neurons; c) the percentage of the TUJ positive cells that are also positive for DAT, the dopamine transporter protein; d) the shape of the cell body should have the characteristic elongated triangular shape of neurons; and e) the length and number of neural projections associated with being TH and DAT positive. For engraftment, the length and number of neural projections is considered to be the most important factor. Examination of the photographs of FIGS. 12-16 show that increasing the amount of various forms of vitamin B around Day 21 of the differentiation protocol greatly enhanced differentiation to dopaminergic neurons based on the morphology and percent yield. Recall that in our control arm, shown in FIG. 16E, 2 forms of vitamins A and C have been added. Referring to FIG. 16A-16E, the percent of the cells, visualized by Hoechst dye, that are TH positive and DAT positive with numerous interconnected and long neural projections show that the addition of the bioactive form of vitamin B6, pyrodoxal-5-phosphate, or the addition of pyridoxal, the immediate precursor of the bioactive form, or the combination of all the vitamin B6 forms starting around Day 21 of the differentiation protocol greatly increase dopamine yield and engraftment potential by generating many long and interconnected neural projections. FIG. 17 is a graph of the amount of dopamine and its metabolites, measured by HPLC, present in the conditioned media from only 200,000 cells taken at Day 30, Day 40, Day 50 or Day 60. Media was not withdrawn from a single source of cells. Rather, separate experiments were allowed to proceed until the day media was withdrawn for analysis. This experiment used Protocol C, where on about Day 20 and forward, retinol and retinyl acetate were added to every condition. The forms of vitamin B that were added to a base neural media were varied. In this experiment, the base media contained about 10 uM pyridoxal. In the condition that has pyridoxine added, Protocol C.2, the pyridoxal is omitted from the base media. It is important to note that in FIG. 17, "NBM" refers a neural base media but vitamin A in the form of retinol and retinyl acetate were also added to it, so that one can compare just the effect of adding more vitamin B in various forms from Day-20 onward. The amount of dopamine and its metabolites secreted into the media were measured by HPLC for 200,000 cells per cm$^2$ Day 30, 40, 50 and Day 60 (FIG. 17).

The graph shows that the peak of dopamine secretion is around Day 50 of the differentiation protocol. As can be seen in the figure, the highest amounts of dopamine come from retinol, retinyl acetate and vitamin C added around Day 20 to neural basal media alone, or with 11 uM pyridoxal added, or with all three B6 forms added together, where pyridoxal is added at 11 uM, 20 uM pyridoxal-5'-phosphate, and 16 uM pyridoxine. We note that the amount of dopamine production and the ability to engraft into an area of a living brain are likely two different measures of a good dopaminergic neuron for implantation. Although the control, neural basal media plus retinol and retinyl acetate produce high amounts of dopamine, they do not generate dopaminergic neurons with the many long interconnected projections that are critical for engraftment.

In one aspect of the invention, pyridoxine or pyridoxine-HCL is added to the differentiation media starting at about Day 16-Day 30 and continued through until implantation or final testing which could be Day 40-Day 60. In another aspect of the invention, pyridoxine or pyridoxine-HCl is added to the differentiation media starting at about Day 20+/−3 and continued through until implantation or final testing which could be Day 40-Day 60. In one aspect, the pyridoxine is added to the differentiation media at Day 20+/−3 to a final concentration of 5.0.uM-25.0 uM. In another aspect, it is added to a final concentration of 10.0 uM-30.0 uM. In another aspect, it is added to a final concentration of 10.0 uM-20.0 uM. In yet another aspect, it is added to a final concentration of 15.0 uM. In another aspect of the invention, pyridoxine is present from the initiation of differentiation at a concentration of 5.0 uM-15.0 uM. In another aspect, pyridoxine is increased to a final concentration of 1.0 uM-30 uM around Day 16-Day 30 and continued through to cell harvest. In another aspect of the invention, pyridoxal is added to the differentiation media around Day 16-Day 30 and continued through until implantation or final testing which could be Day 40-Day 60. In another aspect of the invention, pyridoxal is added to the differentiation media starting at about Day 20+/−3 and continued through until implantation or final testing which could be Day 40-Day 60. In one aspect, pyridoxal is added such that the final concentration in the differentiation media is 10 uM-40 uM. In another aspect, it is added to a final concentration of 10 uM-30.0 uM. In another aspect, it is added to a final concentration of 15 uM-30 uM. In yet another aspect, it is added to a final concentration of 21 uM. In another aspect of the invention, pyridoxal is present from the initiation of differentiation at a concentration of 5.0 uM-15.0 uM. In another aspect pyridoxal is increased to a final concentration of 10 uM-30 uM around Day 16-Day 30 and continued through to cell harvest. In another aspect of the invention, the biologically active form of vitamin B6, pyridoxal-5'-phosphate is added to the differentiation media around Day 16-Day 30 and continued through until implantation or final testing which could be Day 25-Day 60. In another aspect of the invention, pyridoxal-5'-phosphate is added to the differentiation media starting at about Day 20+/−3 and continued through until implantation or final testing which could be Day 30-Day 60. In one aspect, pyridoxal-5'-phosphate is added to a final concentration of 5.0 uM-50.0 uM. In another aspect, it is added to a final concentration of 10.0 uM-30.0 uM. In yet another aspect, it is added to a final concentration of 20.0 uM. In another aspect of the invention, pyridoxal-5'-phosphate is present from the initiation of differentiation at a concentration of 5.0 uM-15.0 uM. In another aspect, pyridoxal-5'-phosphate is present from the initiation of differentiation at a concentration of 5.0 uM-25.0 uM. In another aspect, pyridoxal-5'-phosphate is increased to a final concentration of 10 uM-30 uM around Day 16-Day 30 and continued through to cell harvest. In another aspect, pyridoxal-5'-phosphate is increased to a final concentration of 10 uM-40 uM around Day 16-Day 30 and continued through to cell harvest.

In yet another aspect of the invention, these B vitamins are added together to the differentiation media at around Day 16-Day 30, more preferably at about Day 20+/−3 and continued through until implantation or final testing which could be Day 40-Day 60, wherein the total final concentration of the B vitamins is 5 uM-140 uM. In another aspect of the invention, the total final concentration of the B vitamins is 15 uM-100 uM. In another aspect of the invention, the total final concentration of the B vitamins is 40 uM-70 uM. In another aspect of the invention, the total final concentration of the B vitamins is 50 uM-55 uM. In another aspect of the invention, the total final concentration of the B vitamins is 10 uM-30 uM. In one respect, pyridoxal is present in dopaminergic neuron differentiation media from the onset at about 10 uM, and increased to a final total concentration of 20 uM at Day 20+/−3, along with pyridoxine added at about Day 20+/−3 to a final concentration of 15 uM, and pyridoxal-5'-phosphate added at about Day 20+/−3 to a final concentration of 20 uM.

Vitamin A

The literature has essentially an equal number of publications reporting that vitamin A inhibits neural differentiation and vitamin A promotes neural differentiation [2011 Gudas and Wagner J Cell Physiol 2011 Feb; 226: 322-330; Khillan et al Nutrients 2014 doi: 10.3390/nu6031209; Ole Isacson Molecular and Cellular Neuroscience Vol 45, Issue 3, November 2010; 258-266]. Retinoic acids bind to specific retinoic acid receptors (RARs) in the nucleus and induce expression of genes involved in stem cell differentiation and more particularly, neural differentiation. RARa is the retinoic acid receptor that drives the development of dopaminergic neurons. Therefore, an agonist of RARa, such as BMS753, may be added to the later stage media in place of, or in addition to, various forms of vitamin A.

We discovered that forms of vitamin A are beneficial to the maturation of dopaminergic neurons, however, the timing, concentration and type of vitamin A that are added to base media are significant factors. We modified Protocol A by adding various forms of vitamin A to the basic neural differentiation media starting at about Day 20+/−3 days and continued until cells were harvested at either Day 30, 40, 50 or Day 60. Vitamin A, retinol, its active metabolite retinoic acid (RA), 9cis-RA, all trans RA (atRA), 13cis-RA and/or retinyl acetate were added to the base neural differentiation media. We found that the addition of vitamin A and/or its active metabolites greatly improved the generation of dopaminergic neurons from stem cells, in terms of phenotype, expression of appropriate molecular markers, engraftment and the amount of dopamine produced.

In this set of experiments, naïve state human iPS cells were used. These pluripotent stem cells were cultured in a minimal media with NME7-AB as the only added growth factor (Carter et al 2016). The controls were Protocol A (FIGS. 18A-18I) and, in order to only see the effects of the added vitamin A forms, we employed a modified Protocol A, called Protocol B in which about 10 uM pyridoxal is present in the base media from the onset of differentiation but another 10-11 uM of pyridoxal or pyridoxal-HCL is added starting at day 2-+/−3 days until cell harvest (FIG. 19A-19I).

Figures 23A, 23B, 23C, 23D, 23E:
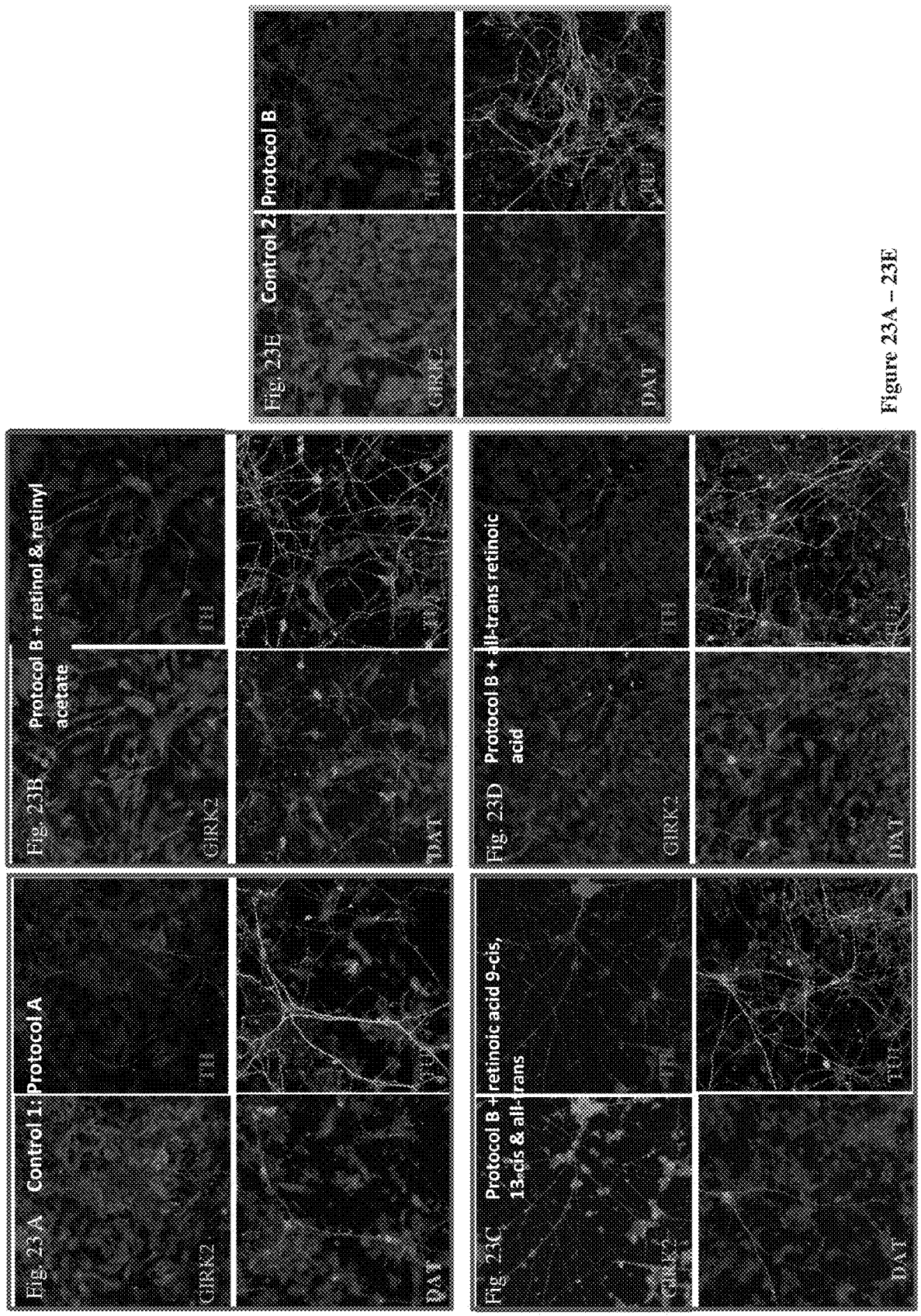
FIG. 23A-23E shows fluorescent photographs taken at 20× magnification on a confocal microscope of human iPS cells at Day 24 of differentiation to dopaminergic neurons.
Figures 24A, 24B, 24C, 24D, 24E:
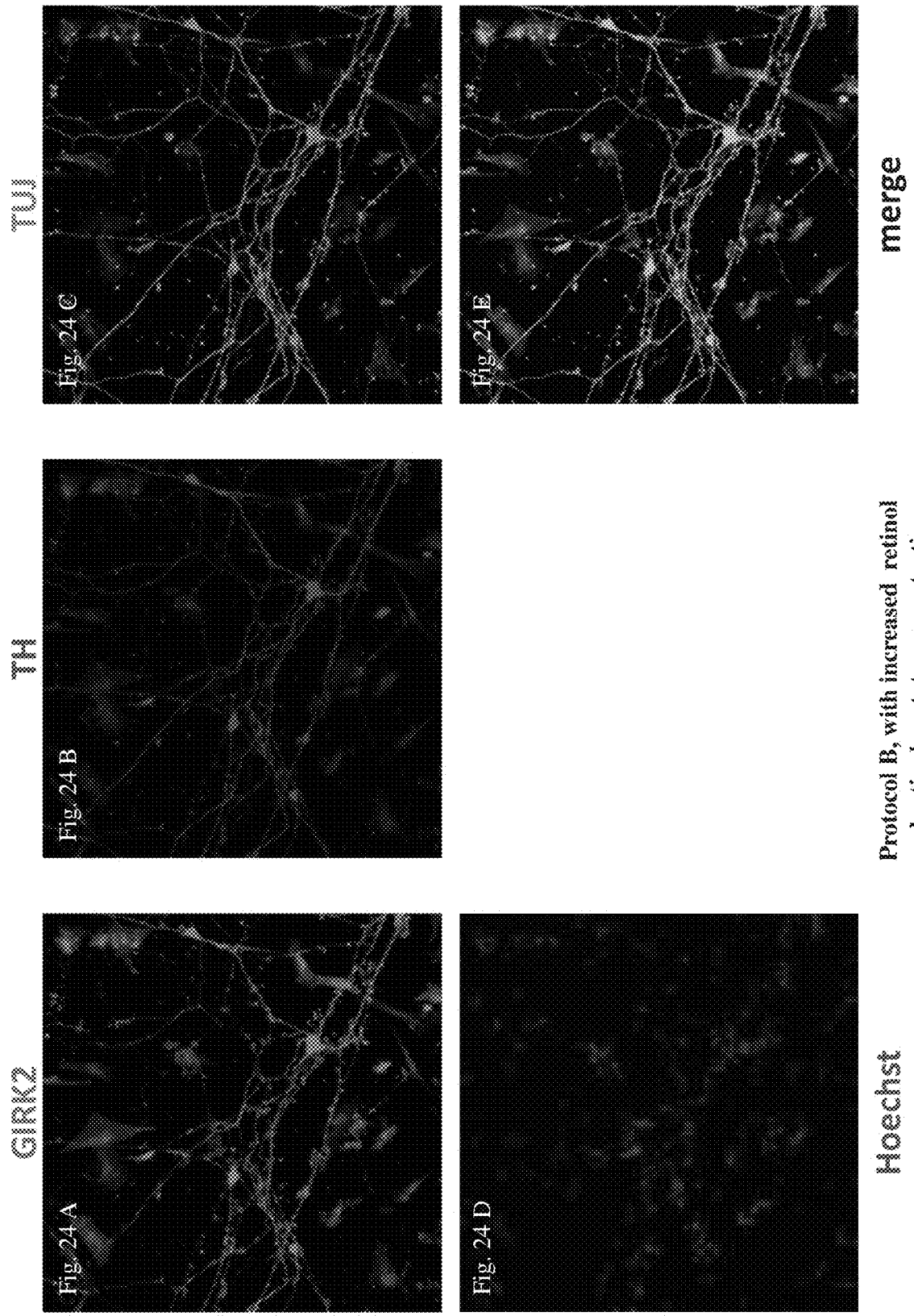
FIG. 24A-24I shows fluorescent photographs taken at 20× magnification on a confocal microscope of human iPS cells at Day 24 of differentiation to dopaminergic neurons, according to Protocol B. In this experiment, in addition to pyridoxal being added to the media from Day 20 onward, two forms of vitamin A were added, wherein the vitamin A had been solubilized in Albumax at 2 mg/mL. Retinol was added to a final concentration of 1.2 uM and retinyl acetate was added to a final concentration of 0.17 uM.
Figure 24F:
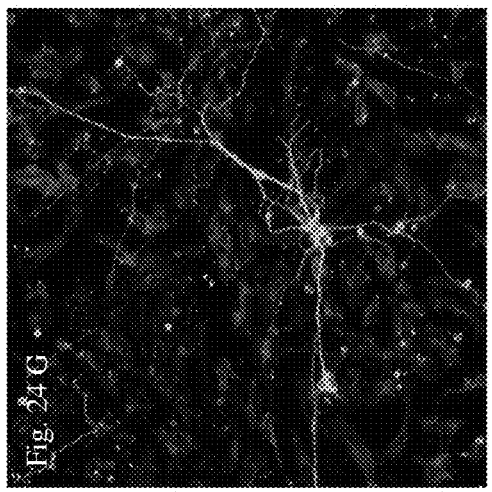
Figure 24G:
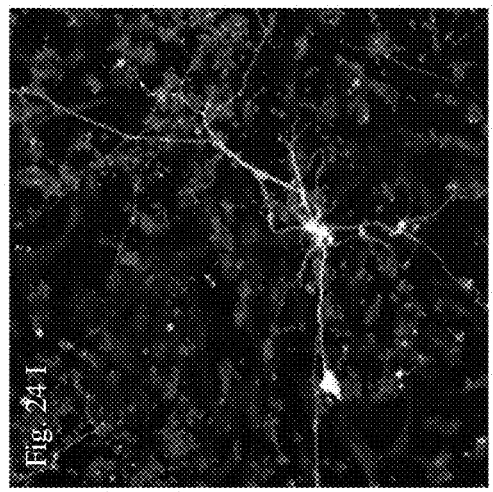
Figure 24H:
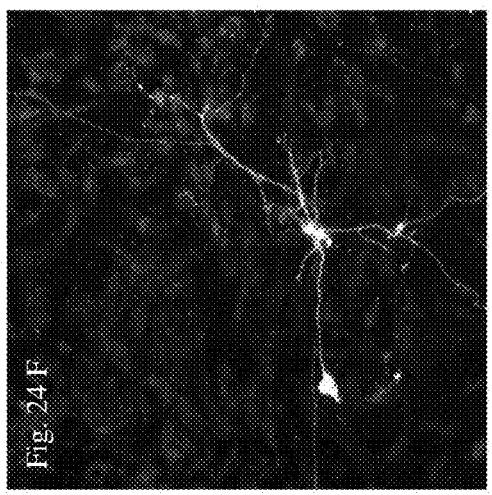
Figure 24I:
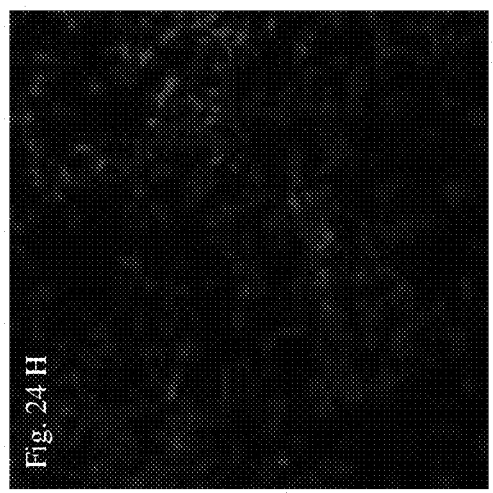
Figure 25A:
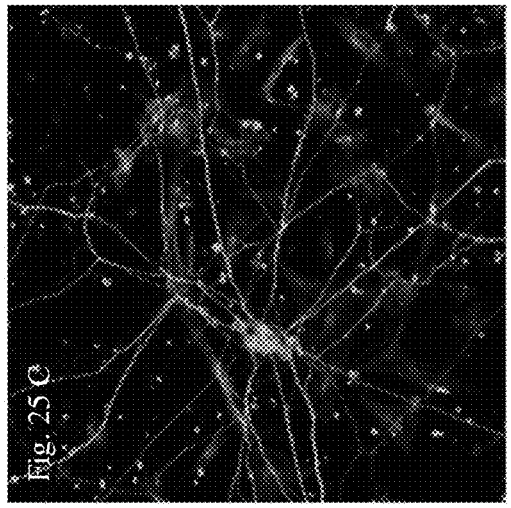
FIG. 25A-25I shows fluorescent photographs taken at 20× magnification on a confocal microscope of human iPS cells at Day 24 of differentiation to dopaminergic neurons, according to Protocol B. In this experiment, in addition to pyridoxal being added to the media from Day 20 onward, two forms of vitamin A were added, plus two forms of vitamin C. The vitamin A had been solubilized in Albumax at 2 mg/mL. Retinol was added to a final concentration of 1.2 uM and retinyl acetate was added to a final concentration of 0.17 uM. Vitamin C was added as 2-phospho-ascorbic acid at 61 uM and L-ascorbic acid at 110 uM.
Figure 25B:
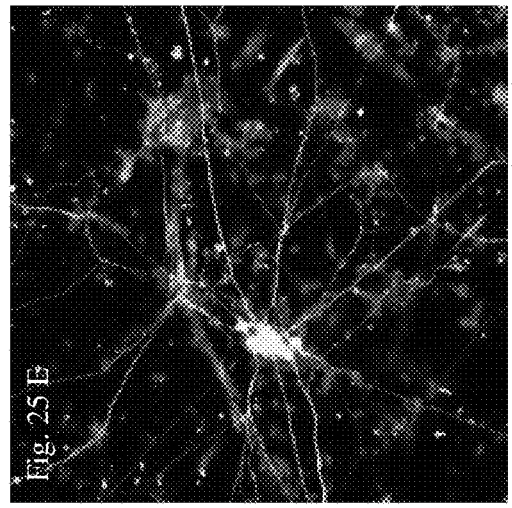
Figure 25C:
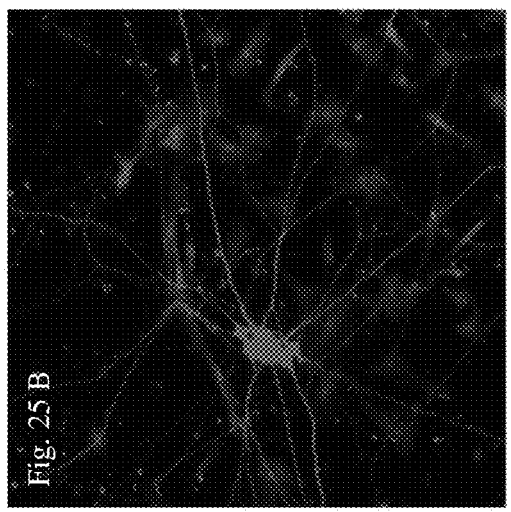
Figure 25D:
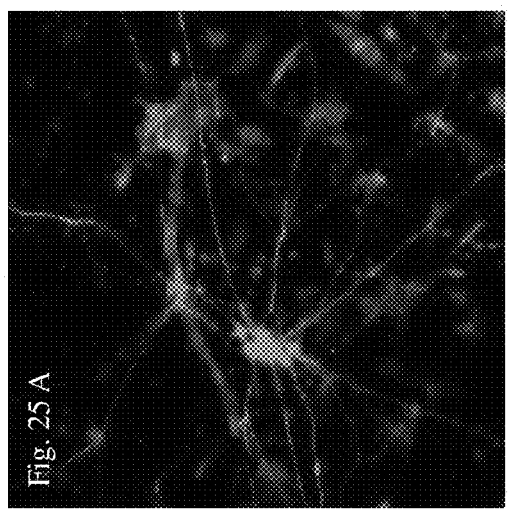
Figure 25E:
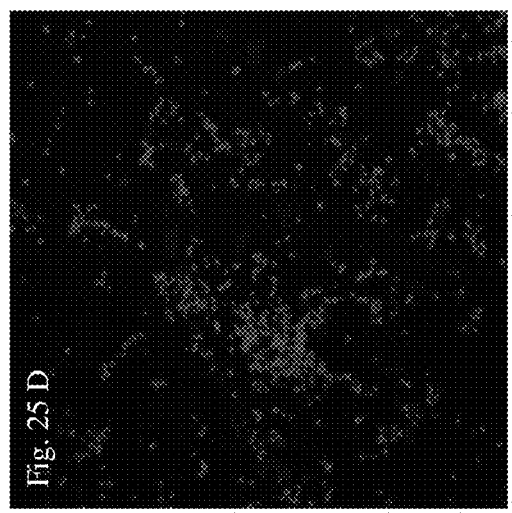
Figure 25F:
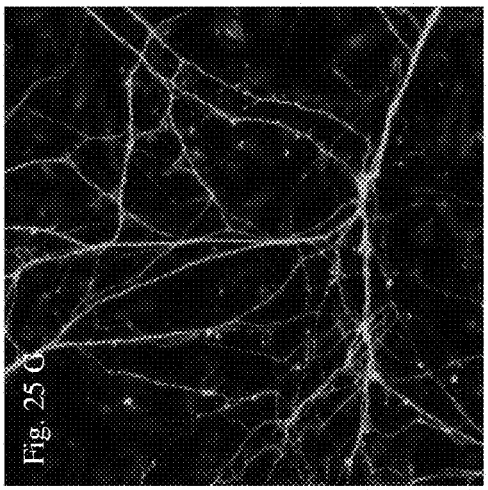
Figure 25G:
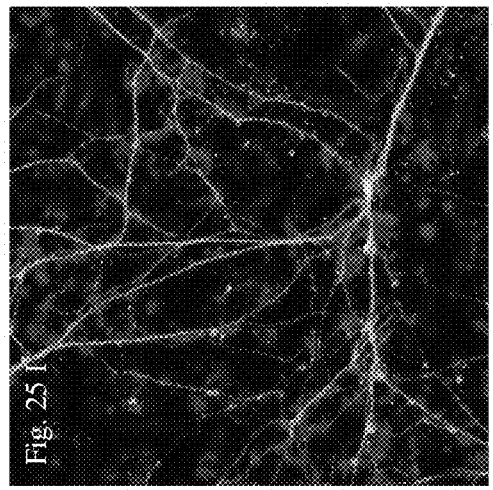
Figure 25H:
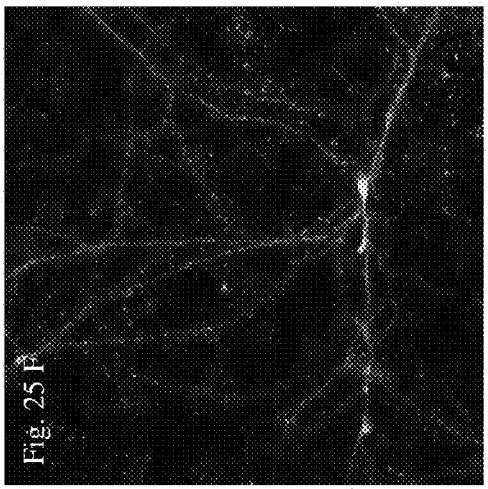
Figure 25I:
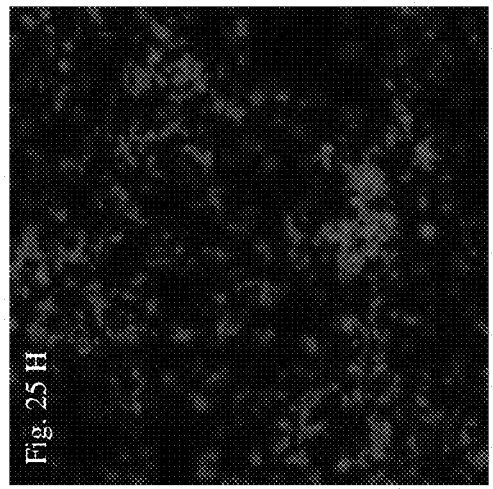
Figure 27F:
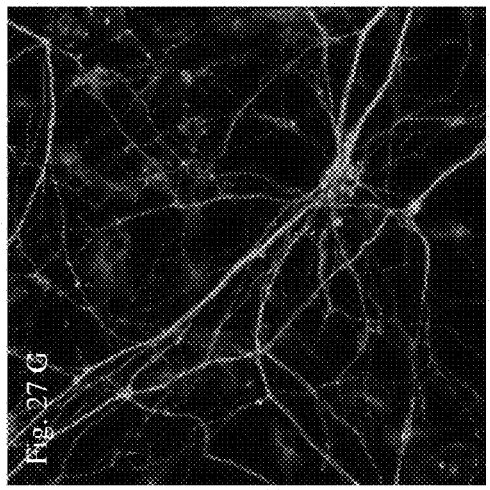
Figure 27G:
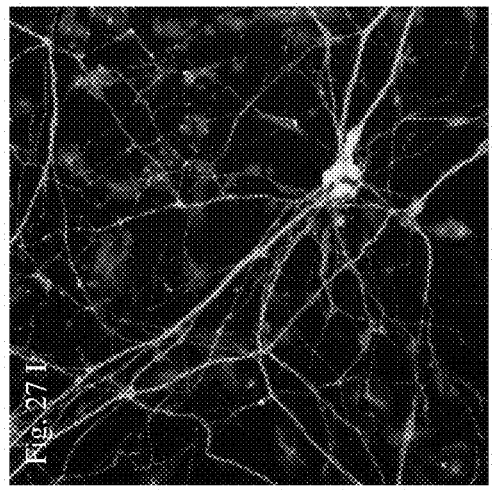
Figure 27H:
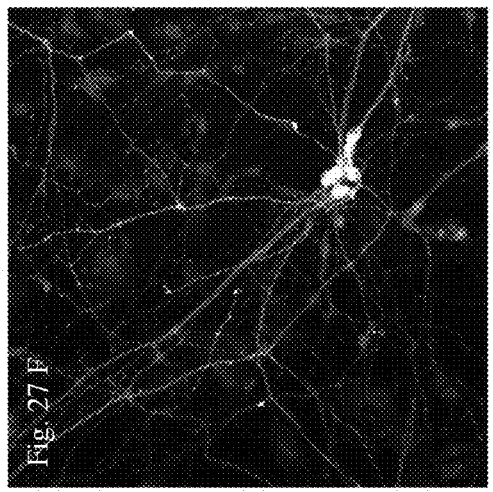
Figure 27I:
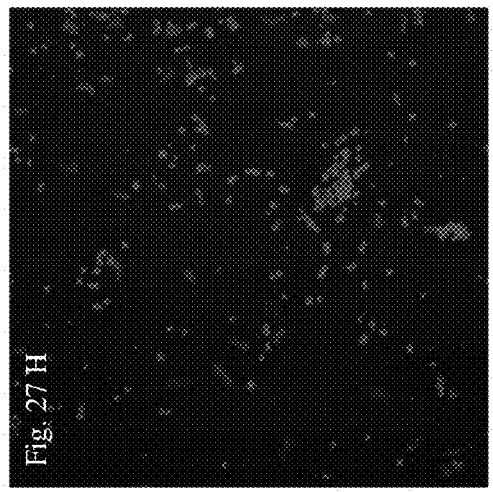

To the differentiating stem cells of Protocol B at about Day 20+/−3 days, vitamin A was added in the form of retinol at a final concentration of 0.7 uM and retinyl acetate at a final concentration of 0.6 uM (FIG. 20A-20I). In another arm of the experiment, the forms of vitamin A that were added around Day 20 were 9-cis, 13-cis and all-trans retinoic acid to a final concentration of 0.446 uM each (FIG. 21A-21I). In another arm of the experiment, only all-trans retinoic acid was added to a final concentration of 1.33 uM (FIG. 22A-22I). FIG. 23A-23E shows the comparison between the two controls, Protocol A, which has no added vitamins B6 or vitamin A added around Day 20 (FIG. 23A) and Protocol B, in which the pyridoxal form of vitamin B6 is increased by adding another 11 uM around Day 20 (FIG. 23E) and the addition of vitamin A in the form of retinol and retinyl acetate (FIG. 23B), or the addition of vitamin A in the form of 9-cis, 13-cis and all-trans retinoic acid (FIG. 23C), or the addition of vitamin A in the form of all-trans retinoic acid (FIG. 23D). As can be seen in the figures, the addition of retinol and retinyl acetate (FIG. 23B) or the addition of 9-cis, 13-cis and all-trans retinoic acid (FIG. 23C) each increased the number, length and inter-connectivity of the neural projections compared to the controls (FIG. 23A and FIG. 23E). However, the morphology of the neural cell bodies stained with GIRK2, combined with the higher percentage of the TUJ positive cells that are also TH positive and DAT positive, indicates that the addition of retinol and retinyl acetate would result in higher engraftment rates.

In one aspect of the invention, retinol, retinyl acetate and/or retinoic acid are added to differentiation media starting about Day 16-Day 30 and continued through until implantation or final testing which could be Day 40-Day 60. In another aspect of the invention, they are added to differentiation media starting about Day 20+/−3 and continued through until implantation or final testing which could be Day 40-Day 60. In one aspect, the vitamin A and/or its derivatives are added to a base media to a final combined concentration of 0.5 uM-5.0 uM. In another aspect, the vitamin A and/or its derivatives are added to a base media to a final combined concentration of 1.0 uM-3.0 uM. In another aspect, retinol is added to the base media at a final concentration of 0.5 uM-5.0 uM. In yet another aspect, retinol is added to the base media at a final concentration of 1.0 uM-2.0 uM and retinyl acetate is also added at a final concentration of 0.1 uM-1.0 uM. In still another aspect, retinol is added to the base media at a final concentration of 1.0 uM-3.0 uM and retinyl acetate is also added at a final concentration of 0.1 uM-1.2 uM. The base media to which the vitamin A and/or its derivatives are added can be a neural differentiation base media, including but not limited to Neural Basal Media (ThermoFisher) and NeuroCult (StemCell Technologies).

Because vitamin A is fat soluble, optionally, lipids or albumin may be added to the base media when vitamin A or its derivatives are added. The base neural media we used contained some BSA, however for human use we sought a non-bovine alternative to BSA. Also, the additional vitamin A would be expected to require additional lipids to aid in solubility. In this set of experiments, vitamin A was first solubilized in Albumax and then added to the differentiation media as described in Protocol B, starting around Day 20+/−3 days. Recall that Protocol B includes the addition of another 11 uM pyridoxal starting at around Day 20+/−3 days. FIG. 24A-24I shows confocal microscope images of resultant cells at Day 24 wherein vitamin A in the form of retinol (1.2 uM) and retinyl acetate (0.17 uM), solubilized in 2 mg/mL of Albumax, were added to media starting around Day 20. FIG. 25A-25I shows confocal microscope images of resultant cells when vitamin C in the form of 2-phospho-ascorbic acid, to a final concentration of 61 uM, and L-ascorbic acid, to a final concentration of 110 uM, are added into the differentiation media at about Day 20 in addition to the aforementioned retinol and retinyl acetate. In another arm of the experiment, to the media of Protocol B around Day 20 was added vitamin A in the form of all-trans retinoic acid to a final concentration of 1.33 uM, solubilized in Albumax (FIG. 26A-FIG. 26I). FIG. 27A-27I shows confocal microscope images of resultant cells when vitamin C in the form of 2-phospho-ascorbic acid, to a final concentration of 61 uM, and L-ascorbic acid, to a final concentration of 110 uM, are added into the differentiation media at about Day 20 in addition to the aforementioned all-trans retinoic acid.

In one aspect of the invention, vitamin C is added to the differentiation media around Day 16-Day 30 of differentiation. In another aspect, vitamin C is added to the differentiation media around Day 20. In one aspect, vitamin C is added to a final concentration of 200 nM-110 uM. In another aspect, vitamin C is added to a final concentration of 1 uM-100 uM. In yet another aspect, vitamin C is added to a final concentration of 50 uM-75 uM. In one aspect, the vitamin C is in the form of 2-phospho-ascorbic acid. In another aspect, it is in the form of L-ascorbic acid. In yet another aspect, both forms of vitamin C are added. In another aspect of the invention, vitamin C is present in the differentiation media from the beginning of differentiation at a final concentration of 100 nM-500 nM. In another aspect of the invention, vitamin C is present from the onset of differentiation at a concentration of 100 nM-500 nM and increased to 50 uM-70 uM around Day 16-Day 30, or from around Day 20.

Figures 5A, 5B, 5C, 5D, 5E, 5F:
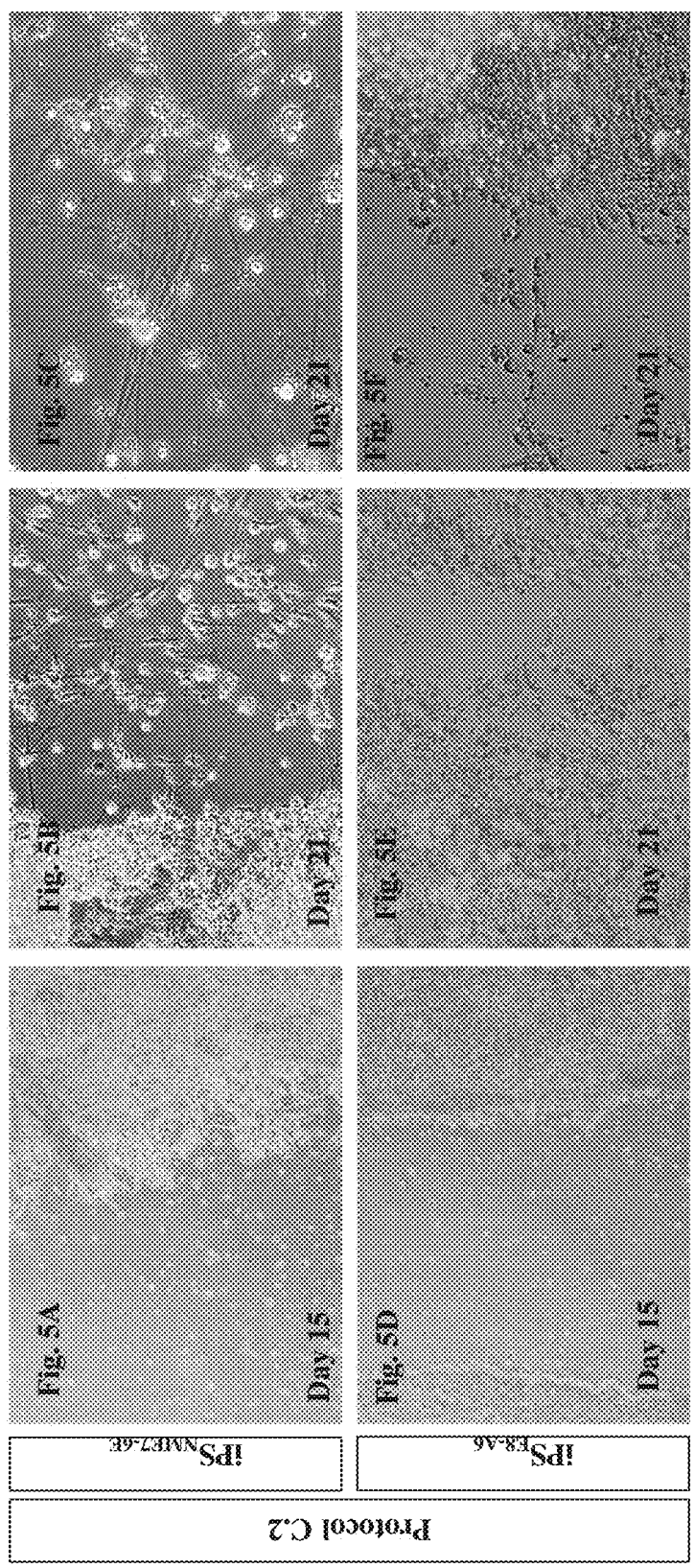
FIG. 5A-5F show fluorescent photographs of a scratch assay, also known as a scar or wound healing assay, that assesses the ability of neurons to engraft. The starting stem cells were either naïve stem cells that had been cultured in $NME7_{AB}$ media, "$iPS_{NME7-6E}$" or primed state stem cells that had been cultured in E8 media, "$iPS_{E8-A6}$". The cells shown were differentiated to dopaminergic neurons according to Protocol C.2 and grown to confluence, which was Day 13 or Day 15. A mechanical scratch was made across the field of cells to create a gap. The rate at which neurite outgrowths bridge that gap is monitored and correlated to engraftment potential. The green fluorescence is a measure of dopamine uptake, from a labeled dopamine.

FIG. 5 shows photographs of a wound healing assay, also called a scratch test, that is considered an in vitro surrogate for in vivo engraftment. The stem cells were differentiated to become dopaminergic neurons according to Protocol C.2. In one case, the starting stem cells were in the naïve state, having been grown in NME7-AB naïve media without any FGF2 or other growth factors (FIG. 5A-FIG. 5C). In another case, the starting stem cells were in the primed state, having been grown in FGF2 containing E8 media (FIG. 5D-FIG. 5F). At Day 21, six (6) days after the scratch was made, the resultant cells were analyzed in the number of neural projections and the length of the neural projections. At Day 21, the neurons derived from the naïve state stem cells had generated 10-12 times more projections than the primed state stem cells, which is an increase of 1000% to 1200%. The length of those projections was 5-7 times longer than those generated in the primed state stem cells, which is a 500% to 700% increase. Therefore, the improvement in simulated engraftment, due only to changing to naïve state stem cells is from 500% to 1200%.

Figures 4A, 4B, 4C, 4D, 4E, 4F, 4G, 4H:
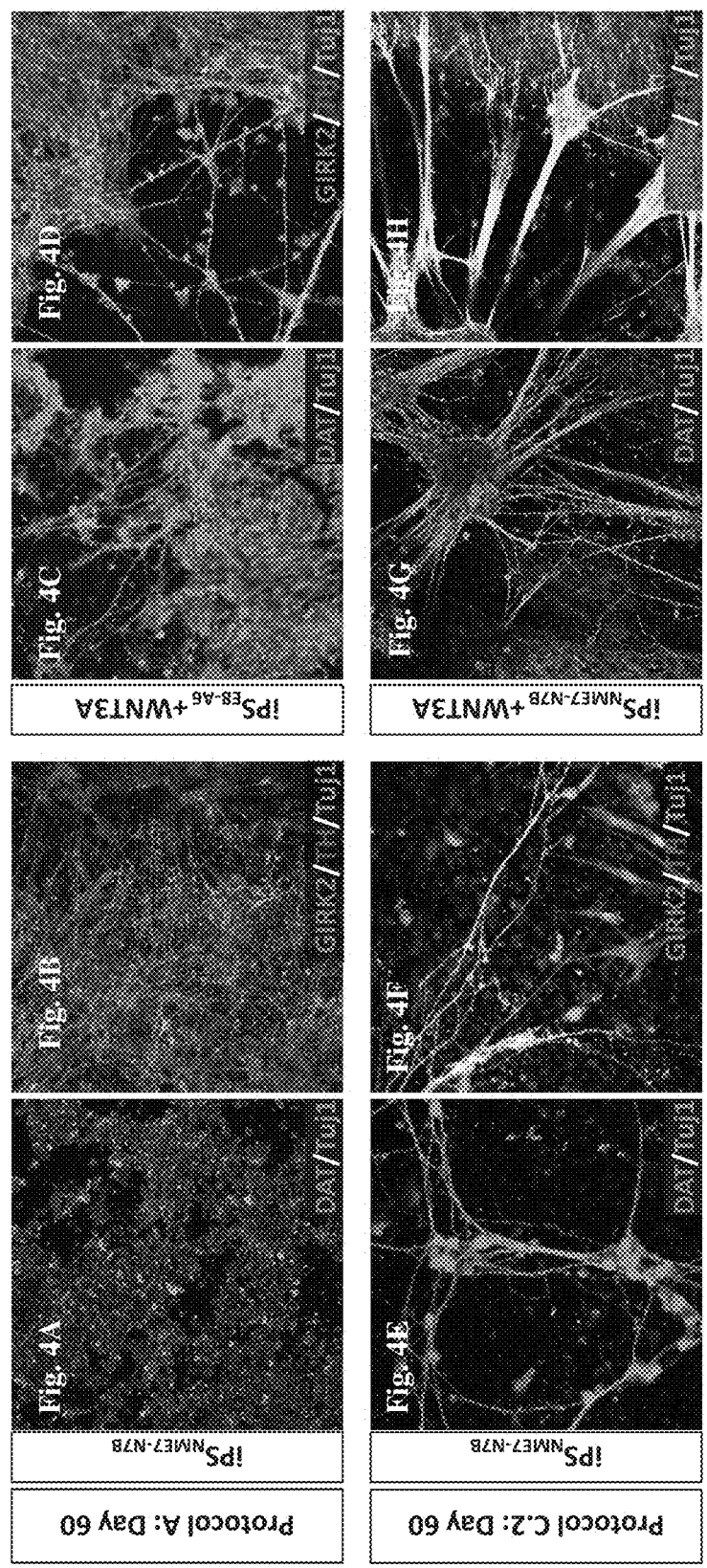
FIG. 4A-4H show fluorescent photographs taken on Day 60 of pluripotent stem cells that were differentiated according to either Protocol A or Protocol C.2. Some of the photographs show cells that were differentiated according to Protocol C.2 but where WNT3A was added to the pluripotent stem cell media, at 100 ng/mL, for 48 hours before the initiation of differentiation.

Improvement to the state of the art is also measured in terms of yield and purity of the resultant population. Recall that conventionally known method for obtaining stem cell derived dopaminergic neurons for the treatment of Parkinson's disease requires sorting cells at Day 14 in order to get a semi-pure population. Such conventional methods indicate that the purified population engrafted into rat brain 10-times better than the impure population. FIG. 4 compares the yield and purity of naïve stem cells differentiated to become dopaminergic neurons using Protocol A versus Protocol C.2. The percentage of the cells in a population that are positive for the four (4) key markers, GIRK2, TH, DAT and Tuj1, and display neural morphology determines the percent purity of the population. The Hoechst dye stains the nuclei of all the cells and Tuj1 is a general stain for many types of neurons, but only those that are positive for Tuj1, GIRK2 (marker of A9 neurons), TH (catalyzes reaction to generate dopamine) and DAT (dopamine transporter protein) are actually dopaminergic neurons. Of the cells that were differentiated according to Protocol A, only about 5% are positive for both GIRK2 and TH, as the overlay of red plus green is yellow (FIG. 4B). In contrast, cells differentiated according to Protocol C.2 have neural morphology and 80%-90% of the Tuj1 positive cells also DAT positive (FIG. 4E) and about 70% both GIRK2 and TH positive (FIG. 4F). Protocol C.2 induced a more than 10-fold (1000%) increase in yield and purity of the dopaminergic neurons.

In another experiment, naïve stem cells were differentiated according to Protocol A (FIG. 18A-FIG. 18I). Here the percentage of cells that are positive for GIRK2, TH, DAT and Tuj1 and that have neural morphology was less than 35%. FIG. 24A-FIG. 24I shows the same starting cells differentiated according to Protocol C, with additional pyridoxal added at Day 21, plus retinol and retinyl acetate. The percentage of the cells that were positive for GIRK2, TH, DAT and Tuj1 was 90%-100%. FIG. 25 shows photographs of the same starting cells differentiated according to Protocol D, which differs from the protocol shown in FIG. 24 in that vitamin C is also added from Day 21 onward in the form of 2-phospho ascorbic acid and L-ascorbic acid. As can be seen in FIG. 25A-FIG. 25I, virtually 100% of the cells have neural morphology and are positive for GIRK2, TH, DAT and Tuj1. Therefore, the percent improvement between Protocol A and the protocol described in the description of FIG. 24 is 250%. The percent improvement between Protocol A and Protocol D (FIG. 25) is 290%.

The other characteristic of dopaminergic neurons that is critical to their utility as a therapeutic for the treatment of Parkinson's disease is their ability to secrete dopamine. Direct comparisons of the amount of dopamine and its metabolites that are produced were quantified between: 1) naïve stem cells versus primed state stem cells; and 2) Protocol A, state of the art and protocol of the invention, Protocol C.2 in which at about Day 24 and onward of Protocol A, the pyridoxal in the base media is exchanged for pyridoxine and vitamin A is added in the form of retinol and retinyl acetate. Graphs of the amount of dopamine and its metabolites that are secreted into the conditioned media at specific days after onset of differentiation, which were measured by HPLC (Vanderbilt University) are shown in FIG. 6 and FIG. 7. First using Protocol A and starting with primed state stem cells, plated at a density of 400,000 cells per $cm^2$, 1.34 ng/mL of dopamine and its metabolites were measured at Day 40 and 13.4 ng/mL at Day 60 (FIG. 6A). Using Protocol A with naïve state stem cells, 1.3 ng/mL were measured at Day 40 and 5.85 ng/mL were measured at Day 60 (FIG. 6B). In contrast, using Protocol C.2 with primed state stem cells, 33.4 ng/mL of dopamine and its metabolites were measured at Day 40 and 15.6 ng/mL were measured at Day 60 (FIG. 6C). Using Protocol C.2 with naïve state stem cells, 43.0 ng/mL of dopamine and its metabolites were measured at Day 40 and 54.1 ng/mL were measured at Day 60 (FIG. 6D). The increase at Day 40 in the secretion of dopamine and its metabolites using Protocol C.2 versus Protocol A is 25-fold, or 2500%, when using primed state stem cells and 33-fold, or 3300%, when using naïve state stem cells. In FIG. 7, the amount of dopamine secreted from a variable number of cells at Day 60, or Day 40, where indicated is graphed. Using naïve state stem cells, plated at a density of 800,000 cells per $cm^2$, at Day 60, the cells differentiated according to Protocol C.2 produced about 10-fold more dopamine (54 ng/mL versus 5.8 ng/mL) than the same cells differentiated according to Protocol A. When only half that number of cells were plated, 400,000 cells per $cm^2$, cells differentiated with Protocol C.2 produced about 2.0-2.6 times more dopamine than the same cells differentiated using Protocol A. Comparing the amount of dopamine produced according to current state of the art, primed state cells and Protocol A (3 ng/mL from 800K cells at Day 60), versus compositions and methods of the invention, naïve state stem cells according to Protocol C.2 (54 ng/mL from 800K cells at Day 60), naïve stem cells and Protocol C.2 produced 18-times more dopamine, 1800%, than the state of the art.

In one aspect of the invention, Protocol B is modified such that starting at about day 20+/−3 days of the differentiation protocol, the differentiation media is supplemented with retinol, which is added to a final concentration of 0.5 uM-2.0 uM and retinyl acetate is added to a final concentration of 0.1-1.5 uM. In another aspect of the invention, the retinol is added to a final concentration of 0.7-1.2 uM and the retinyl acetate is added to a final concentration of 0.17-0.6 uM. In yet another aspect of the invention, a combination of retinol and retinyl acetate is added such that the combined final concentration is 1.0 uM-2.5 uM. In yet another aspect of the invention the combined final concentration is 1.33 uM.

In one aspect, bovine serum albumin is added. In another aspect, human serum albumin is added. In yet another aspect, a lipid rich human serum albumin is added. In still another aspect, Albumax, a lipid rich bovine albumin or a similar lipid rich human albumin is added. The lipid rich albumin may be added to a final molar concentration of 10.0 uM-40.0 uM. The final molar concentration may be 10.0 uM-15.0 uM. In one aspect, vitamin A and/or its derivatives is dissolved in an alcohol/water mixture and evaporated under vacuum to form a thin film. The thin film is then mixed with a solution of BSA or HSA at 37° C. for 30 minutes to dissolve the lipid.

Vitamin C is expressed at high levels in the fetal brain during late stages of neural development. Vitamin C has been reported to be involved in the upregulation of Nurr1, which is critical for midbrain neural differentiation and could be a key factor in the maturation of dopaminergic neurons. In one aspect of the invention, vitamin C 2-phospho-L-ascorbic acid trisodium salt is added to the differentiation media around Day 16-Day 30 and continued through until implantation or final testing which could be Day 40-Day 60. In another aspect of the invention, vitamin C 2-phospho-L-ascorbic acid trisodium salt is added to the differentiation media at Day 20+/−3 and continued through until implantation or final testing which could be Day 40-Day 60. In one aspect the vitamin C 2-phospho-L-ascorbic acid trisodium salt is added to the differentiation media to a final concentration of 40.0 uM-100.0 uM. In another aspect, it is added to a final concentration of 50.0 uM-70.0 uM. In yet another aspect, it is added to a final concentration of 60.0 uM-65.0 uM. In another aspect of the invention, vitamin C ascorbic acid is added to the differentiation media around Day 16-Day 21 and continued through until implantation or final testing which could be Day 40-Day 60. In yet another aspect of the invention, vitamin C ascorbic acid is added to the differentiation media at Day 20+/−3 and continued through until implantation or final testing which could be Day 40-Day 60. In one aspect the ascorbic acid is added to the differentiation media to a final concentration of 5.0 uM-20.0 uM. In another aspect, it is added to a final concentration of 10.0 uM-15.0 uM. In yet another aspect, it is added to a final concentration of 12.0 uM-14.0 uM.

In one aspect of the invention, vitamin C in the form of 2-phospho-ascorbic acid is added to the differentiation media around Day 20 to a final concentration of 25 uM-100 uM. In another aspect of the invention, it is added to a final concentration of 40-75 uM. In a preferred embodiment, it is added to a final concentration of 61 uM. In one aspect of the invention, vitamin C in the form of L-ascorbic acid is added to the differentiation media around Day 20 to a final concentration of 1 uM-120 uM. In another aspect of the invention, it is added to a final concentration of 5-100 uM. In a preferred embodiment, it is added to a final concentration of 11 uM. In a preferred embodiment, one or more forms of vitamin C are added to the media of Protocol B at about Day 20+/−3 days to a final concentration of 50-75 uM. In a more preferred embodiment, the two forms of vitamin C are 2-phospho ascorbic acid and L-ascorbic acid.

In one aspect of the invention, the aforementioned vitamins are added into a base neural media, at the concentrations given, together with a lipid rich albumin, and stem cells undergoing differentiation to dopaminergic neurons and cultured in this media from about Day 16-Day 30, in particular from Day 20+/−3, until terminal differentiation or implantation which could be between Day 30 and Day 60, post initiation of differentiation.

In addition to our discovery of key vitamins, their metabolites and lipid rich albumin, which when added to differentiating stem cells increase and enhance the differentiation to dopaminergic neurons, we found that the use of naïve state stem cells further increases and enhances differentiation to dopaminergic neurons.

In a preferred embodiment, stem cells are differentiated to dopaminergic neurons according to Protocol C.

In a more preferred embodiment, stem cells are differentiated to dopaminergic neurons according to Protocol D, in which stem cells, that are preferably NME7-AB grown naïve stem cells, are in a neural base media that around Day 20+/−3 days, is supplemented by the addition of 11 uM pyridoxal or 20 uM pyridoxal-5'-phosphate, 1.2 uM retinol and 0.17 uM retinyl acetate, solubilized in a lipid rich formulation and 61 uM 2-phospho ascorbic acid and 11 uM L-ascorbic acid.

In yet another aspect of the invention, the protocols of the invention, including Protocol B, Protocol C, Protocol C.2 or Protocol D are applied to pluripotent stem cells that have been cultured in a pluripotent stem cell media that contains NME7-AB.

In yet another aspect of the invention, the protocols of the invention, including Protocol B, Protocol C, Protocol C.2 or Protocol D are applied to pluripotent stem cells that have been cultured in a pluripotent stem cell media that contains WNT3A.

The improvement to the state of the art that is described here, is the addition of various forms of specific vitamins at specific concentrations, and other factors, to a base neural differentiation media. In one aspect of the invention, the addition or increased concentrations of vitamin A, vitamin B and/or vitamin C begins with the onset of differentiation and is continued throughout the differentiation process. In another aspect of the invention, they are added 16-30 days after the initiation of differentiation and continued through to cell harvest. In yet another aspect of the invention, they are added around 18-23 days after initiating differentiation and continued through to cell harvest. In one effective embodiment, the candidate factors were added on Day 20 or 21. These vitamins A, B6 and C, which we found are dopaminergic maturation factors can be added to several different basic neural differentiation media, including but not limited to Neural Basal Media (ThermoFisher), NeuroCult (StemCell Technologies), or other neural differentiation base media.

In some of the examples shown here, the basics of Protocol A (FIG. 1, Example 1), were employed until about Day 20+/−3 days, when specific vitamins were added into the base neural differentiation media. Addition of these factors around Day 20+/−3 greatly increased the yield and functionality of stem cell derived dopaminergic neurons, including increasing engraftment and dopamine secretion, while enabling the in vitro maturation of fully functional dopaminergic neurons.

Method of Treating Neurodegenerative Disorders, Condition or Injury

The in vitro differentiated dopaminergic neurons may be used for treating a neurodegenerative disorder. The compositions and methods demonstrated herein are applicable to the generation of other types of neurons from stem cells. The differentiated dopaminergic neurons may be used to treat any condition that would benefit from successful engraftment of dopaminergic neurons in the central nervous system, such as neurodegenerative disease conditions. Other types of neurons can be generated from stem cells using methods of the invention for treatment of other conditions such as those caused by injuries such as to spinal cord. Neurons such as sensory neurons, motor neurons or interneurons may be generated from stem cells according to methods of the invention. These neurons may be also used to treat peripheral nerve injury, which may include total or partial transection of a nerve from stretching, cutting (laceration), compression, shearing, or crushing. The presently disclosed subject matter provides for methods of treating a neurodegenerative disorder comprising administering an effective amount of the presently disclosed differentiated dopaminergic neurons into a subject suffering from a neurodegenerative disorder.

Non-limiting examples of a neurodegenerative disorders include Parkinson's disease, Huntington's disease, Alzheimer's disease, and multiple sclerosis. Other neurotrophic B vitamins may be added to the protocols described herein. For example, vitamin B12, which aids in the generation of myelin, may be added to the differentiation media when neurons for the treatment of multiple sclerosis are generated.

In particular, the neurodegenerative disease is Parkinson's disease. Primary motor signs of Parkinson's disease include, for example, but not limited to, tremor of the hands, arms, legs, jaw and face, bradykinesia or slowness of movement, rigidity or stiffness of the limbs and trunk and postural instability or impaired balance and coordination.

In certain embodiments, the neurodegenerative disease is a parkinsonism disease, which refers to diseases that are linked to an insufficiency of dopamine in the basal ganglia, which is a part of the brain that controls movement. Symptoms include tremor, bradykinesia (extreme slowness of movement), flexed posture, postural instability, and rigidity. Non-limiting examples of parkinsonism diseases include corticobasal degeneration, Lewy body dementia, multiple systematrophy, and progressive supranuclear palsy.

The presently disclosed differentiated dopaminergic neurons can be administered or provided systemically or directly to a subject for treating or preventing a neurodegenerative disorder. In certain embodiments, the presently disclosed differentiated dopaminergic neurons are directly injected into an organ of interest (e.g., the central nervous system (CNS) or peripheral nervous system (PNS). In certain embodiments, the presently disclosed differentiated dopaminergic neurons are directly injected into the striatum.

The presently disclosed differentiated dopaminergic neurons can be administered in any physiologically acceptable vehicle. Pharmaceutical compositions comprising the presently disclosed differentiated dopaminergic neurons and a pharmaceutically acceptable vehicle are also provided. The presently disclosed differentiated dopaminergic neurons and the pharmaceutical compositions comprising said cells can be administered via localized injection, orthotopic (OT) injection, systemic injection, intravenous injection, or parenteral administration. In certain embodiments, the presently disclosed differentiated dopaminergic neurons are administered to a subject suffering from a neurodegenerative disorder via orthotopic (OT) injection.

The presently disclosed differentiated dopaminergic neurons and the pharmaceutical compositions comprising said cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof. Sterile injectable solutions can be prepared by incorporating the compositions of the presently disclosed subject matter, e.g., a composition comprising the presently disclosed differentiated dopaminergic neurons, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the presently disclosed subject matter, however, any vehicle, diluent, or additive used would have to be compatible with the presently disclosed differentiated dopaminergic neurons.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the presently disclosed differentiated dopaminergic neurons. This will present no problem to those skilled in chemical and pharmaceutical principles, or problems can be readily avoided by reference to standard texts or by simple experiments (not involving undue experimentation), from this disclosure and the documents cited herein.

In certain non-limiting embodiments, the cells and precursors described herein are comprised in a composition that further comprises a biocompatible scaffold or matrix, for example, a biocompatible three-dimensional scaffold that facilitates tissue regeneration when the cells are implanted or grafted to a subject. In certain non-limiting embodiments, the biocompatible scaffold comprises extracellular matrix material, synthetic polymers, cytokines, collagen, polypeptides or proteins, polysaccharides including fibronectin, laminin, keratin, fibrin, fibrinogen, hyaluronic acid, heparin sulfate, chondroitin sulfate, agarose or gelatin, and/or hydrogel. (See, e.g., U.S. Publication Nos. 2015/0159135, 2011/0296542, 2009/0123433, and 2008/0268019, the contents of each of which are incorporated by reference in their entireties). In certain embodiments, the composition further comprises growth factors for promoting maturation of the implanted/grafted cells into midbrain DA cells.

One consideration concerning the therapeutic use of the presently disclosed differentiated dopaminergic neurons is the quantity of cells necessary to achieve an optimal effect. An optimal effect includes, but is not limited to, repopulation of CNS and/or PNS regions of a subject suffering from a neurodegenerative disorder, and/or improved function of the subject's CNS and/or PNS.

In certain embodiments, an effective amount of the presently disclosed differentiated dopaminergic neurons is an amount that is sufficient to repopulate CNS and/or PNS regions of a subject suffering from a neurodegenerative disorder. In certain embodiments, an effective amount of the presently disclosed differentiated dopaminergic neurons is an amount that is sufficient to improve the function of the CNS and/or PNS of a subject suffering from a neurodegenerative disorder, e.g., the improved function can be about 1%, about 5%, about 10%, about 20%, about 30%, about 40%, about 50%, about 60%, about 70%, about 80%, about 90%, about 95%, about 98%, about 99% or about 100% of the function of a normal person's CNS and/or PNS.

The quantity of cells to be administered will vary for the subject being treated. In certain embodiments, from about $1 \times 10^4$ to about $1 \times 10^{10}$, from about $1 \times 10^4$ to about $1 \times 10^5$, from about $1 \times 10^5$ to about $1 \times 10^9$, from about $1 \times 10^5$ to about $1 \times 10^6$, from about $1 \times 10^5$ to about $1 \times 10^7$, from about $1 \times 10^6$ to about $1 \times 10^7$, from about $1 \times 10^6$ to about $1 \times 10^8$, from about 1×10⁷ to about 1×10⁸, from about 1×10⁸ to about 1×10⁹, from about 1×10⁸ to about 1×10¹⁰, or from about 1×10⁹ to about 1×10¹⁰ of the presently disclosed differentiated dopaminergic neurons are administered to a subject. In certain embodiments, from about 1×10⁵ to about 1×10⁷ of the presently disclosed differentiated dopaminergic neurons are administered to a subject suffering from a neurodegenerative disorder. In certain embodiments, from about 1×10⁶ to about 1×10⁷ of the presently disclosed differentiated dopaminergic neurons are administered to a subject suffering from a neurodegenerative disorder. The precise determination of what would be considered an effective dose may be based on factors individual to each subject, including their size, age, sex, weight, and condition of the particular subject. Dosages can be readily ascertained by those skilled in the art from this disclosure and the knowledge in the art.

EXAMPLES

Example 1—Protocol A

In Protocol A, cells were plated onto Geltrex-coated plates in NeuroBasal™ neurobasal media (Thermo Fisher #21103049), B-27™ w/o Vitamin A (Thermo Fisher #12587010), N2 supplement (Stem Cell Technologies #07156), 2 mM Glutamax (Thermo Fisher #35050061), 250 nM LDN193189 (Selleck Chemicals #S7507), 10.8 μM SB431542 (Selleck Chemicals #S1067), 500 ng/ml SHH (R&D Systsems #464-SH-200), 0.7 μM CHIR99021 (R&D Systems #4423), 10 uM Y27632 (Selleck Chemicals #S1049). On days 1 and 3, the media was replaced with fresh NeuroBasal™ neurobasal media containing B-27™ w/o Vitamin A, N2 supplement, 2 mM Glutamax, 250 nM LDN193189, 10.8 μM SB431542, 500 ng/ml SHH, 0.7 μM CHIR99021. On days 4 and 6, the media was replaced with fresh NeuroBasal™ neurobasal media containing B- 27™ w/o Vitamin A, N2 supplement, 2 mM Glutamax, 250 nM LDN193189, 10.8 M SB431542, 500 ng/ml SHH, 7.5 μM CHIR99021. On days 7 and 9, the media was replaced with fresh NeuroBasal™ neurobasal media containing B-27™ w/o Vitamin A, N2 supplement, 2 mM Glutamax, 7.5 μM CHIR99021. On day 10, the media was replaced with fresh NeuroBasal™ neurobasal media containing B-27™ w/o Vitamin A, 2 mM Glutamax, 3μM CHIR99021, 20 ng/mL BDNF (Peprotech #450-02), 200 nM Ascorbic Acid (Sigma Aldrich #A4403), 20 ng/ml GDNF (Peprotech #450-10), 1 ng/mL TGFβ3 (Peprotech #100-36E), 500 nM cAMP (Peprotech #1698950). On day 11, the cells were replated onto 15 μg Poly-L-ornithine (Sigma Aldrich #P4957) /1 μg Laminin (Sigma Aldrich #L2020)/1 μg Fibronectin (Thermo Fisher #33016-015) coated plates in Day 10 media with 10 μM Y27632. On days 12 to 60, the media was changed daily with NeuroBasal™ neurobasal media containing B-27™ w/o Vitamin A, 2 mM Glutamax, 20 ng/ml BDNF, 200 nM Ascorbic Acid, 20 ng/ml GDNF, 1 ng/ml TGFβ3, 500 nM cAMP, 10 μM DAPT (Selleck Chem #S2215).

NeuroBasal™ neurobasal media (Thermo Fisher #21103049) is indicated to contain: amino acids of glycine, L-Alanine, L-Arginine hydrochloride, L-Asparagine-H2O, L-Cysteine, L-Histidine hydrochloride-H2O, L-Isoleucine, L-Leucine, L-Lysine hydrochloride, L-Methionine, L-Phenylalanine, L-Proline, L-Serine, L-Threonine, L-Tryptophan, L-Tyrosine, L-Valine; Vitamins of 0.028571420 mM Choline chloride, 0.008385744 mM D-Calcium pantothenate, 0.009070295 mM Folic Acid, 0.032786883 mM Niacinamide, 0.019607844 mM Pyridoxal hydrochloride, 0.0010638298 mM Riboflavin, 0.011869436 mM Thiamine hydrochloride, 5.0184503E-6 mM Vitamin B12, 0.04 mM i-Inositol; Inorganic salts of Calcium Chloride (CaC12) (anhyd.), Ferric Nitrate (Fe(NO3)3"9H2O), Magnesium Chloride (anhydrous), Potassium Chloride (KCl), Sodium Bicarbonate (NaHCO3), Sodium Chloride (NaCl), Sodium Phosphate monobasic (NaH2PO4-H2O), Zinc sulfate (ZnSO4-7H2O); Other components of D-Glucose (Dextrose), HEPES, Phenol Red, Sodium Pyruvate.

Example 2—Investigating Effects of Adding Vitamin B6 Forms to Protocol a

In this set of experiments, we used a base neural media, starting at approximately Day 20 and onward, contains 10 uM pyridoxal plus 1.2 uM retinol and 0.17 uM retinyl acetate. Increased levels of various B vitamins were added around the time that researchers had found that implantation into host brain increased engraftment, which is around Day 20. On Day 20 +/-3, we added: pyridoxine to a final concentration between 5-25 uM; pyridoxal to a final concentration between 5-20 uM; pyridoxal-5'-phosphate, the bioactive form, to a final concentration between 10-40; or all three B vitamins combined. It was empirically determined that an optimal concentration of pyridoxine was about 10-20 uM. FIG. 12A-FIG. 12K shows the effect of pyridoxine added to a final concentration of 16 uM. It was empirically determined that an optimal concentration of pyridoxal was about 5-20 uM. FIG. 13A-13K shows the effect of pyridoxal added to a final concentration of 11 uM. It was empirically determined that an optimal concentration of pyridoxal-5'-phosphate was about 10-40 uM. FIG. 14A-14K shows the effect of pyridoxal-5'-phosphate added to a final concentration of 20 uM. FIG. 15A-15K shows the effect of all three vitamin B's added together.

Example 3—Protocol B

Based on the results of Example 2, we limited the type and concentration of vitamin B6 added at about Day 20, so that we could next investigate the type and concentrations of vitamin A that may or may not improve the purity/yield, the engraftment or the amount of dopamine secreted by the stem cell-derived dopaminergic neurons.

In Protocol B, cells were plated onto Geltrex-coated plates in NeuroBasal™ neurobasal media, B-27™ w/o Vitamin A, N2 supplement, 2 mM Glutamax, 250 nM LDN193189, 10.8 μM SB431542, 500 ng/ml SHH, 0.7 μM CHIR99021, 10 μM Y27632. On days 1 and 3, the media was replaced with fresh NeuroBasal™ neurobasal media containing B-27™ w/o Vitamin A, N2 supplement, 2 mM Glutamax, 250 nM LDN193189, 10.8 μM SB431542, 500 ng/ml SHH, 0.7 μM CHIR99021. On days 4 and 6, the media was replaced with fresh NeuroBasal™ neurobasal media containing B-27™ w/o Vitamin A, N2 supplement, 2 mM Glutamax, 250 nM LDN193189, 10.8 μM SB431542, 500 ng/ml SHH, 7.5 μM CHIR99021. On days 7 and 9, the media was replaced with fresh NeuroBasal™ neurobasal media containing B-27™ w/o Vitamin A, N2 supplement, 2 mM Glutamax, 7.5 μM CHIR99021. On day 10, the media was replaced with fresh NeuroBasal™ neurobasal media containing B-27™ w/o Vitamin A, 2 mM Glutamax, 3 μM CHIR99021, 20 ng/mL BDNF (Peprotech #450-02), 200 nM Ascorbic Acid (Sigma Aldrich #A4403), 20 ng/ml GDNF (Peprotech #450-10), 1 ng/mL TGFβ3 (Peprotech #100-36E), 500 nM cAMP (Peprotech #1698950). On day 11, the cells were replated onto 15 μg Poly-L-ornithine (Sigma Aldrich #P4957)/10 μg Laminin (Sigma Aldrich #L2020)/1

μg Fibronectin (Thermo Fisher #33016-015) coated plates in Day 10 media with 10 μM Y27632. On days 12 to 20, the media was changed daily with NeuroBasal™ neurobasal media containing B-27™ w/o Vitamin A, 2 mM Glutamax, 20 ng/mL BDNF, 200 nM Ascorbic Acid, 20 ng/ml GDNF, 1 ng/ml TGFβ3, 500 nM cAMP, 10 μM DAPT (Selleck Chem #S2215). On days 21 to 60 or until cell harvest, the media was changed daily with NeuroBasal™ neurobasal media containing B-27™ w/o Vitamin A, 2 mM Glutamax, 20 ng/mL BDNF, 200 nM Ascorbic Acid, 20 ng/mL GDNF, 1 ng/mL TGFβ3, 500 nM cAMP, 10 μM DAPT, plus 11 μM pyridoxal (Sigma Aldrich P1930).

Example 4—Investigating Effects of Adding Various Forms of Vitamin a to Protocol B On or about Day 20 of the differentiation according to Protocol B, various forms of vitamin A were added over a range of concentrations. Retinol was added from Day-20 onward at a concentration range of 0.1-1.5 uM. Retinyl acetate was added from Day-20 onward at a concentration range of 0.1-1.5 uM. Retinoic acid in the forms of 9-cis, 13-cis, and/or all-trans were added such that the final concentration, whether added separately or together was about 1.5-2.0 uM. Results are shown as FIG. 18-FIG. 23. It was empirically determined that an optimal condition for differentiation of dopaminergic neurons was the addition of both retinol and retinyl acetate together at around Day 20 and onward to a final combined concentration of about 2 uM.

Example 5—Investigating Effects of Adding Various Forms of Vitamin a, solubilized in lipid rich formulation, plus or minus vitamin C, to Protocol B Vitamin A is known to be fairly insoluble. We therefore tested the addition of the various forms of vitamin A after it had been solubilized in a lipid rich formulation. We tested solubilizing vitamin A in BSA at 2 mg/mL or in Albumax, which could be substituted by human serum albumin. In addition to adding in various forms of a solubilized vitamin A, we tested the addition of even more vitamin C in the form of 2-phospho-ascorbic acid or L-ascorbic acid. The results of these studies are shown in FIG. 24-FIG. 27.

Example 6—Protocol C

In Protocol C, Protocol A is followed until Day 20+/−3 days, with the exception that at Day 11, the surface onto which the differentiating cells are re-plated comprises 10 ug/mL of Laminin instead of 1 ug/mL. According to Protocol C, around Day 20, the media is supplemented with: vitamin B6 in the form of either pyridoxine at 16 uM, pyridoxal at 11 uM, pyridoxal-5'-phosphate at 20 uM, or all together; and vitamin A in the form of retinol at 0.7-1.2 uM and retinyl acetate 0.17-0.6 uM, or 9-cis retinoic acid, 13-cis retinoic acid and all-trans retinoic acid each at 0.446 uM, or all-trans retinoic acid at 1.33 uM; and vitamin C in the form of 2-phospho-ascorbic acid at 61 uM and L-ascorbic acid at 110 uM.

Example 7—Protocol C.2

In Protocol C.2, Protocol A is followed until Day 20+/−3 days, with the exception that at Day 11, the surface onto which the differentiating cells are re-plated comprises 10 ug/mL of Laminin instead of 1 ug/mL. According to Protocol C.2, around Day 20, the neural base media is exchanged for one that does not contain pyridoxal, but instead contains vitamin B6 in the form of pyridoxine at 16 uM and vitamin A in the form of retinol at 1.2 uM and retinyl acetate 0.17 uM.

Example 8—Protocol D

In Protocol D, Protocol A is followed until Day 20+/−3 days, with the exception that at Day 11, the surface onto which the differentiating cells are re-plated comprises 10 ug/mL of Laminin instead of 1 ug/mL. According to Protocol D, around Day 20 and onward, the media is supplemented with: pyridoxal at 11 uM, retinol at 1.2 uM and retinyl acetate at 0.17 uM, and vitamin C in the form of 2-phospho-ascorbic acid at 61 uM and L-ascorbic acid at 11 uM. See FIG. 3-FIG. 10 for quantification of stem cells differentiated to dopaminergic neurons according to Protocol C.2.

Those skilled in the art will recognize, or be able to ascertain using no more than routine experimentation, many equivalents to the specific embodiments of the invention specifically described herein. Such equivalents are intended to be encompassed in the scope of the claims.

We claim:

1. A method of producing dopaminergic neurons from human stem cells comprising a step of adding or increasing a concentration of vitamins to neurobasal media at approximately Day 20 +/−3 of a protocol for differentiating pluripotent stem cells into dopaminergic neurons,
   wherein the vitamins comprise vitamin A and vitamin B6, and
   wherein the dopaminergic neurons are characterized by producing greater than 30% more dopamine and its metabolites on Day 30 than dopaminergic neurons produced by the same differentiation protocol without added or increased vitamins.

2. The method of claim 1, wherein the differentiation protocol comprises:
   plating the human stem cells in a culture medium comprising LDN193189, SB431542, Sonic Hedgehog, and about 0.7 μM CHIR99021 on Day 0; and
   increasing the concentration of CHIR99021 to about 7.5 μM on about Day 4.

3. The method of claim 1, wherein the vitamin A is in the form of retinal.

4. The method of claim 1, wherein the vitamin A is in the form of retinyl acetate.

5. The method of claim 1, wherein the vitamin A is in the form of 9-cis retinoic acid, 13-cis retinoic acid or all-trans retinoic acid.

6. The method of claim 1, wherein the vitamin A is solubilized in a lipid rich formulation.

7. The method of claim 6, wherein the lipid rich formulation is human serum albumin.

8. The method of claim 6, wherein the lipid rich formulation is a chromatographically purified lipid-rich bovine serum albumin for cell culture with an IgG content of no more than 0.1%.

9. The method of claim 6, wherein the lipid rich formulation is non-human serum albumin.

10. The method of claim 1, wherein the vitamin A is in a final concentration of from 1 μM to 3 μM.

11. The method of claim 1, wherein the vitamin B6 is in the form of pyridoxine.

12. The method of claim 1, wherein the vitamin B6 is in the form of pyridoxal.

13. The method of claim 1, wherein the vitamin B6 is in the form of pyridoxal-5'-phosphate, also known as PLP.

14. The method of claim 1, wherein the vitamin B6 is in a final concentration of from 10 μM to 30 μM.

15. The method of claim 1, wherein the vitamins further comprise vitamin C.

16. The method of claim 15, wherein the vitamin C is in the form of 2-phospho-ascorbic acid.

17. The method of claim 15, wherein the vitamin C is in the form of L-ascorbic acid.

18. The method of claim 15, wherein the vitamin C is in a final concentration of from 200 nM to 110 μM.

19. The method of claim 1, wherein the human stem cells have been cultured in NME7-AB.

20. The method of claim 1, wherein the human stem cells have been cultured in WNT3A.

21. The method of claim 1, wherein the human stem cells are in a naïve state.

22. The method of claim 1, wherein the human stem cells are induced pluripotent stem cells (iPSCs).

23. The method of claim 22, wherein the iPSCs are in a naïve state.

24. The method of claim 1, wherein the human stem cells are embryonic stem cells.

25. The method of claim 1, wherein the method does not comprise cell sorting to isolate the dopaminergic neurons.

26. The method of claim 1, wherein the dopaminergic neurons are characterized by forming greater than 30% more neurites than dopaminergic neurons produced by a differentiation protocol without added or increased vitamins.

27. The method of claim 26, wherein the dopaminergic neurons are characterized by forming greater than 100% more neurites than dopaminergic neurons produced by a differentiation protocol without added or increased vitamins.

28. A method of increasing likelihood of successful grafting of dopaminergic neurons to a subject in need thereof comprising administering to the subject the dopaminergic neurons obtained by the method of claim 1.

29. A method of treating a central nervous system disease in a patient for which engraftment of dopamine producing neural cells is desired, comprising engrafting dopaminergic neurons obtained in the method of claim 1 to a person in need thereof.

30. The method of claim 29, in which the central nervous system disease is Parkinson's Disease, Huntington's Disease, multiple sclerosis or Alzheimer's Disease.

31. A method of producing dopaminergic neurons from human stem cells comprising a step of adding or increasing a concentration of vitamins to neurobasal media at approximately Day 20 +/−3 of a protocol for differentiating pluripotent stem cells into dopaminergic neurons,
wherein the vitamins comprise vitamin A and vitamin B6, and
wherein the dopaminergic neurons are characterized by forming greater than 30% more neurites by Day 21 than dopaminergic neurons produced by the same differentiation protocol without added or increased vitamins.

32. The method of claim 31, wherein the differentiation protocol comprises:
on Day 0, plating the human stems on a culture plate coated with basement membrane in a first culture medium comprising a neurobasal medium, an N2 supplement, LDN193189, SB431542, Sonic Hedgehog, about 0.7 μM CHIR99021, and Y27632;
on Day 1 and Day 3, replacing the culture medium with a second culture medium comprising the neurobasal medium, an N2 supplement, LDN193189, SB431542, Sonic Hedgehog, and about 0.7 μM CHIR99021;
on Day 4 and Day 6, replacing the culture medium with a second culture medium comprising the neurobasal medium, an N2 supplement, LDN193189, SB431542, Sonic Hedgehog, and about 7.5 μM CHIR99021;
on Day 7 and Day 9, replacing the culture medium with a third culture medium comprising the neurobasal medium, the N2 supplement, and about 7.5 μM CHIR99021;
on Day 10, replacing the second culture medium with a fourth culture medium comprising the neurobasal medium, CHIR99021, BDNF, GDNF, ascorbic acid, TGFp3, and cAMP;
on Day 11, plating the cells on a surface coated with polyornithine 1 μg/ml laminin, and fibronectin, in the fourth culture medium,
on Day 12, Day 13, Day 14, Day 15, Day 16, Day 17, Day 18, Day 19, Day 20, and Day 21, replacing the culture medium with a fifth culture medium comprising the neurobasal medium, BDNF, GDNF, ascorbic acid, TGF3, cAMP, and DAPT,
wherein the neurobasal medium comprises amino acids vitamins, inorganic salts, and D-Glucose; and
wherein the N2 supplement comprises transferrin, insulin, progesterone, putrescine, and selenite.

33. The method of claim 31, wherein the vitamin A is solubilized in a lipid rich formulation.

34. The method of claim 31, wherein the vitamin B6 is in a final concentration of from 10 μM to 30 μM.

35. The method of claim 31, wherein the pluripotent stem cells have been cultured in NME7-AB.

36. The method of claim 31, wherein the pluripotent stem cells are in a naïve state.

37. The method of claim 31, wherein the dopaminergic neurons are characterized by expressing greater than 30% more dopamine than dopaminergic neurons produced by a differentiation protocol without added or increased vitamin.

* * * * *